(12) United States Patent
Herget et al.

(10) Patent No.: US 12,139,742 B2
(45) Date of Patent: Nov. 12, 2024

(54) DEVICES, SYSTEMS, AND METHODS FOR PREPARING A STANDARDIZED INOCULUM FOR ANTIMICROBIAL SUSCEPTIBILITY TESTING

(71) Applicant: Avails Medical, Inc., Menlo Park, CA (US)

(72) Inventors: Meike Herget, Woodside, CA (US); Creighton T. Buie, Daly City, CA (US); Nitin K. Rajan, Palo Alto, CA (US); Andrew H. THeiss, Mountain View, CA (US); Elizabeth Botbol Ponte, Menlo Park, CA (US); Oren S. Knopfmacher, San Francisco, CA (US); Michael D. Laufer, Menlo Park, CA (US); Eszter Deak, San Jose, CA (US); Suzanne Putney, San Francisco, CA (US)

(73) Assignee: Avails Medical, Inc., Menlo Park, CA (US)

( * ) Notice: Subject to any disclaimer, the term of this patent is extended or adjusted under 35 U.S.C. 154(b) by 680 days.

(21) Appl. No.: 17/443,990

(22) Filed: Jul. 29, 2021

(65) Prior Publication Data

US 2021/0371896 A1 Dec. 2, 2021

Related U.S. Application Data

(63) Continuation-in-part of application No. PCT/US2021/032237, filed on May 13, 2021.

(60) Provisional application No. 63/058,264, filed on Jul. 29, 2020, provisional application No. 63/025,575, filed on May 15, 2020.

(51) Int. Cl.
| | |
|---|---|
| *C12Q 1/24* | (2006.01) |
| *B01L 3/00* | (2006.01) |
| *G01N 27/00* | (2006.01) |
| *G01N 33/487* | (2006.01) |
| *G01N 33/49* | (2006.01) |
| *G01N 35/00* | (2006.01) |
| *G01N 35/10* | (2006.01) |

(52) U.S. Cl.
CPC ............... *C12Q 1/24* (2013.01); *B01L 3/508* (2013.01); *G01N 27/00* (2013.01); *G01N 33/48707* (2013.01); *G01N 33/49* (2013.01); *G01N 35/00693* (2013.01); *G01N 35/1009* (2013.01); *B01L 2300/02* (2013.01); *B01L 2300/042* (2013.01); *B01L 2300/046* (2013.01)

(58) Field of Classification Search
CPC ......... A42B 3/046; A42B 3/0486; A42B 3/30; A42B 3/00; A42B 3/322; G08B 21/02; G08G 1/096741; G08G 1/09675; G08G 1/096775; G08G 1/096725; G08G 1/166; A41D 13/018; A41D 13/05; A41B 3/00; B60W 30/08; B60W 30/09; B60W 50/14; B60T 2201/024
See application file for complete search history.

(56) References Cited

U.S. PATENT DOCUMENTS

| | | |
|---|---|---|
| 5,338,435 A | 8/1994 | Betts et al. |
| 7,022,517 B1 | 4/2006 | McDevitt et al. |
| 8,128,989 B1 | 3/2012 | Millar et al. |
| 10,161,897 B2 | 12/2018 | Wu |
| 2010/0292611 A1 | 11/2010 | Lum et al. |

FOREIGN PATENT DOCUMENTS

| | | | |
|---|---|---|---|
| CN | 214011281 | 8/2021 | |
| JP | H06-288962 | 10/1994 | |
| WO | WO-2019246208 A1 * | 12/2019 | ............ B01L 3/5023 |
| WO | WO 2021/231718 | 11/2021 | |

OTHER PUBLICATIONS

Mathes et al, The pharmaceutical vial capping process: Container closure systems, capping equipment, regulatory frame work and seal quality tests, European Journal of Pharmaceutics, 2016, pp. 54-64 (Year: 2016).*

* cited by examiner

*Primary Examiner* — Narayan K Bhat
(74) *Attorney, Agent, or Firm* — Levine Bagade Han LLP

(57) ABSTRACT

Various apparatus, systems, and methods for measuring a solution characteristic of a sample comprising microorganisms are disclosed. The measured solution characteristic can be used to generate a standardized inoculum. In one embodiment, a sensor apparatus is disclosed comprising a sample container having a chamber lateral wall surrounding a chamber cavity configured receive the sample, a reference sensor fabricated as a container cap and comprising a reference electrode material and, and an active sensor made of a substrate covered in part by an active electrode layer. The active sensor can be coupled to at least part of the chamber lateral wall at a window opening defined along the chamber lateral wall. The solution characteristic can be measured using a reader configured to electrically couple to the sensor apparatus and measure the solution characteristic based on a potential difference between the active sensor and the active sensor.

13 Claims, 24 Drawing Sheets

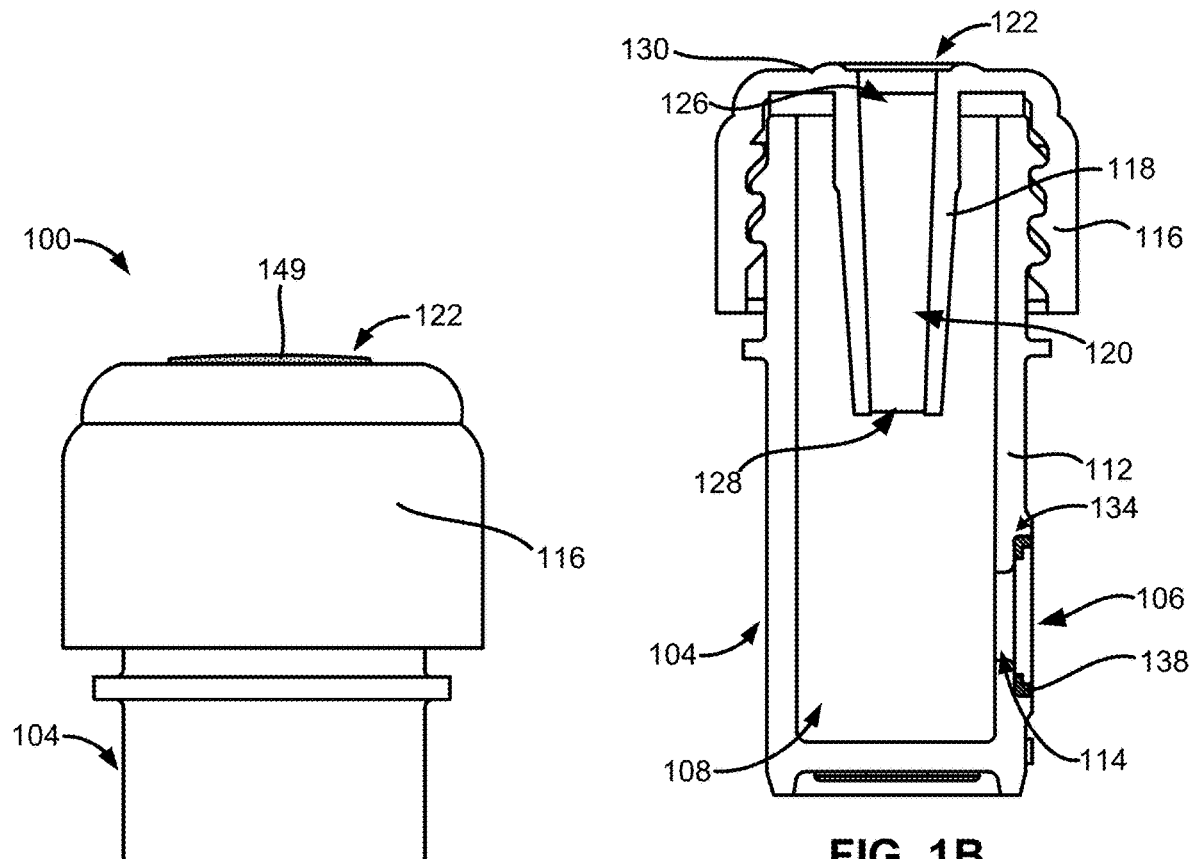
FIG. 1A
FIG. 1B
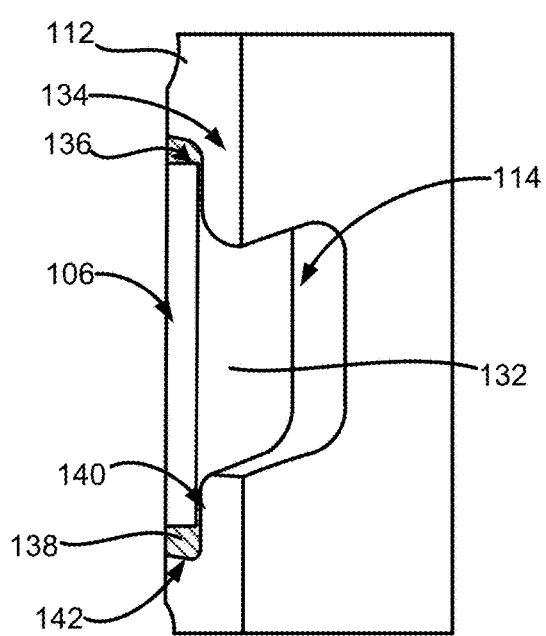
FIG. 1C

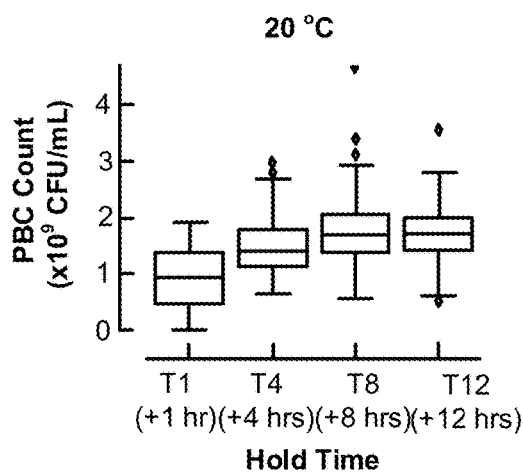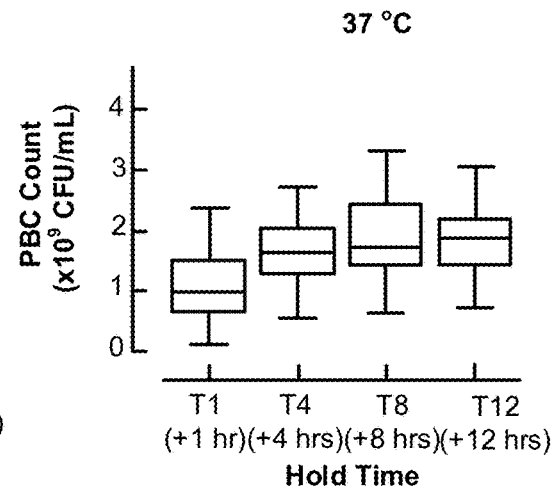
FIG. 22A    FIG. 22B
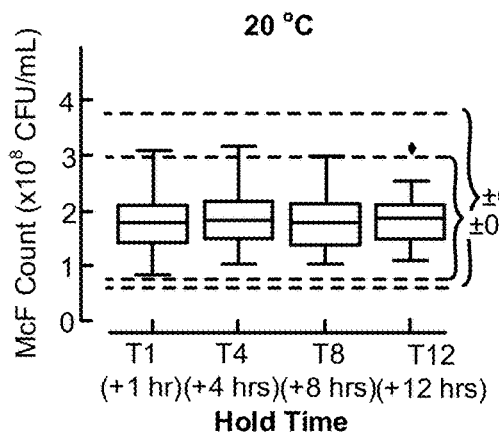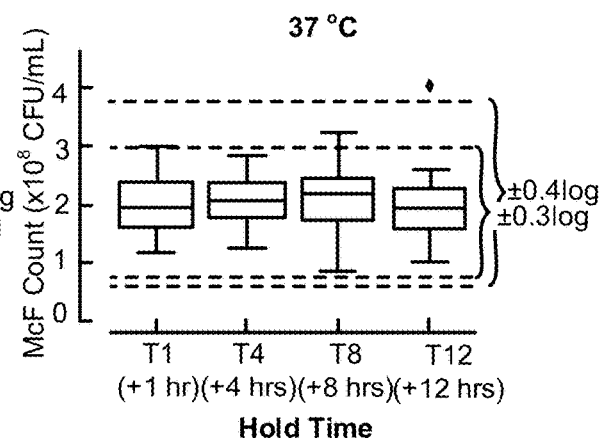
FIG. 22C    FIG. 22D

DEVICES, SYSTEMS, AND METHODS FOR PREPARING A STANDARDIZED INOCULUM FOR ANTIMICROBIAL SUSCEPTIBILITY TESTING

CROSS-REFERENCE TO RELATED APPLICATIONS

This application is a continuation-in-part (CIP) of International Patent Application No. PCT/US2021/032237, filed on May 13, 2021, which claims the benefit of U.S. Provisional Application No. 63/025,575 filed on May 15, 2020, the content of which is incorporated herein by reference in its entirety. This application also claims the benefit of U.S. Provisional Application No. 63/058,264 filed on Jul. 29, 2020, the content of which is incorporated herein by reference in its entirety.

TECHNICAL FIELD

The present disclosure relates generally to diagnostic devices and, more specifically, to devices, systems, and methods for preparing a standardized inoculum from a source sample for downstream testing.

BACKGROUND

Infections caused by anti-infective resistant infectious agents or microbes are a significant problem for healthcare professionals in hospitals, nursing homes, and other healthcare environments. For example, such infections can lead to a potentially life-threatening complication known as sepsis where chemicals released into the bloodstream by an infectious agent can trigger a dangerous whole-body inflammatory response as well as a vasoactive response causing fever, low blood pressure, and possibly death. A key predictor for morbidity and mortality for patients with a bloodstream infection is time to appropriate antimicrobial therapy. Accelerating antimicrobial susceptibility testing (AST) from biological samples such as positive blood cultures (PBCs) is, therefore, key to improving patient outcomes.

A preferred course of action when faced with such an infection is for a clinician to use anti-infective compounds (e.g., antibiotics) judiciously, preferably only those necessary to alleviate the infection. However, what occurs most frequently today is that until the organism is identified and tested for drug sensitivity, broad-spectrum anti-infectives, often multiple drugs, are given to the patient to ensure adequacy of treatment. This tends to result in multiple drug-resistant infectious agents. Ideally, the sensitivity of the infectious agent would be detected soon after its presence is identified.

In order to determine the susceptibility of such infectious agents to anti-infectives, samples comprising such infectious agents must be quantified and a standardized inoculum must be prepared from a sample such as a PBC. Traditionally, a standardized inoculum, such as a 0.5 McFarland suspension, is prepared by first subculturing a PBC on an agar plate and incubating the plate until there is sufficient growth to make the suspension from distinct bacterial colonies. A 0.5 McFarland is a turbidity standard equivalent to a bacterial suspension containing between $1*10^8$ colony forming units per mL (CFU/mL) to $2*10^8$ CFU/mL. This often requires between 18 and 24 hours of incubation time. The 0.5 McFarland inoculum is then used directly for AST testing using disk diffusion or diluted further for automated AST platforms.

Measurements to determine whether a sample meets the McFarland standard cannot be performed directly from PBCs due to the interference of blood cells (e.g., red blood cells) with optical measurement equipment. PBCs comprise components that have the potential to interfere with the measurement of the culture sample. While there have been efforts to develop methods to generate standardized inoculum directly from PBC using serum separator tubes, lysis filtration, and/or centrifugation, such methods tend to be manual, time-consuming, and must be extensively validated before they can be adopted by the clinical laboratory.

Moreover, current in vitro diagnostic measurement systems, especially those used to detect infectious agents in biological samples, are often not designed with both high-performance and low-cost considerations in mind. Also, since it is important to prevent cross-contamination of patient samples, a single-use disposable consumable is the preferred design for the sensing component of the diagnostic measurement system. This puts significant emphasis on the cost and manufacturability of a single-use disposable sensing component.

Traditional biosensors are often made using costly glass or silicon substrates that drive up the cost of such sensors and require numerous manufacturing steps to produce. Moreover, the active sensing component of such biosensors may malfunction when the biological sample or other fluid sample makes inadvertent contact with the conductive parts of the active sensing component not intended to contact the sample.

Therefore, a solution is needed that addresses the above shortcomings and limitations. Such a solution should be automated and use a sensing component that is single-use and cost-effective to manufacture. Such a solution should also allow users to accurately and quickly prepare a standardized inoculum directly from a biological sample such as a PBC.

SUMMARY

Disclosed are apparatus, systems, and methods for measuring a solution characteristic (e.g., an ORP or a pH) of a sample comprising microorganisms and for preparing a standardized inoculum from a source sample for downstream testing. In one embodiment, a sensor apparatus for measuring a solution characteristic of a sample is disclosed. The sensor apparatus can comprise a sample container. The sample container can comprise a chamber lateral wall surrounding a chamber cavity configured to receive the sample. The sensor apparatus can also comprise a reference sensor comprising a reference electrode material and a wick in fluid communication with the chamber cavity within the sample container. At least some of the sample can be drawn up by the wick in a direction of the reference electrode material.

The sensor apparatus can also comprise an active sensor made of a conductive substrate covered in part by an active electrode layer. The active sensor can be coupled to at least part of the chamber lateral wall at a window opening defined along the chamber lateral wall. In some embodiments, no part of the active sensor extends into the chamber cavity. The active electrode layer can face the chamber cavity to allow the sample within the chamber cavity to be in fluid contact with the active electrode layer through at least part of the chamber lateral wall surrounding the window opening. The solution characteristic of the sample can be determined based on a potential difference measured between the active sensor and the reference sensor when the reference sensor and the active sensor are electrically coupled to a reader apparatus.

The solution characteristic measured can be an oxidation reduction potential. The solution characteristic measured can be pH. The active electrode layer can comprise at least one of a platinum oxide layer (formed on a platinum layer) and a tantalum oxide layer. The conductive substrate can be stainless steel. The active electrode layer can have an active electrode layer thickness of between about 50 nm and 500 nm. The active sensor can further comprise an adhesion layer between the conductive substrate and the active electrode layer. The adhesion layer can have a thickness of between 5 nm and 50 nm. A ratio of the adhesion layer thickness to the active electrode layer thickness can be between about 1:10 and 1:20. The adhesion layer can be a chromium layer, a gold layer, or a nickel layer.

The active layer can have an active electrode layer thickness of 400 nm. The active sensor can be insert-molded into the chamber lateral wall while the sample container is formed by injection molding. The active sensor can be press-molded into the chamber lateral wall after the sample container is formed by injection molding. The chamber lateral wall can comprise a recessed portion surrounding the window opening. The recessed portion can be defined along an exterior side of the chamber lateral wall. The active sensor can be adhered to at least part of the chamber lateral wall within the recessed portion via an adhesive.

The active sensor can comprise an active electrode side, a conductive substrate side opposite the active electrode side, and lateral sides. The lateral sides can be covered by at least one of the chamber lateral wall and an adhesive to prevent the lateral sides from contacting the sample. The sample container can be made in part of at least one of polyoxymethylene, polyamide, polyethylene, acrylonitrile butadiene styrene, polycarbonate, and polypropylene. The reference electrode material can be a cured or hardened electrically-conductive ink deposited or otherwise applied on a wick proximal end of the wick.

In some embodiments, the active sensor can be made of a non-conductive printed circuit board (PCB) substrate covered in part by an electrode layer. The active electrode layer can be electrically coupled to conductive contacts of the PCB substrate by a conductive via extending through the PCB substrate. The PCB substrate can be a flexible PCB substrate.

The PCB substrate can be made in part of polyimide, an FR-4 composite material, copper, or the like. The solution characteristic measured can be an oxidation reduction potential. The active electrode layer can be a platinum layer or a gold layer. The active electrode layer can have an active electrode layer thickness of at least 50 nm. In certain embodiments, the active electrode layer can have an active electrode layer thickness of at least 400 nm.

In some embodiments, the active sensor can be made of a non-conductive polymeric substrate comprising a through-hole. One side of the polymeric substrate and one end of the through-hole can be covered by a conductive layer. The active electrode layer can be electrically coupled to the conductive layer via a conductive coating covering lateral sides of the through-hole.

The active electrode layer can be a platinum layer or a gold layer. The active electrode layer can have an active electrode layer thickness of at least 50 nm. In certain embodiments, the active electrode layer can have an active electrode layer thickness of at least 400 nm.

The active sensor can be a rectangular piece having a width dimension of between about 100 μm and 6.0 mm and a length dimension of between about 100 μm and 6.0 mm. The through-hole can have a diameter between about 10 μm to 100 μm. The conductive coating covering the lateral sides of the through-hole can be a coating of platinum, gold, or the like.

In some embodiments, the active sensor can be made of a conductive dowel covered in part by an active electrode layer. The active sensor can be coupled to at least part of the chamber lateral wall at a window opening defined along the chamber lateral wall. The part of the conductive dowel covered by the active electrode layer can extend into the chamber cavity to allow the sample within the chamber cavity to be in fluid contact with the active electrode layer. An end of the conductive dowel not extending into the chamber cavity can extend out of the chamber lateral wall. The conductive dowel can be made in part of stainless steel and can be shaped substantially as a cylinder having rounded edges.

Also disclosed is a method of measuring a solution characteristic of a sample. The method can comprise cleaning a conductive substrate with an acid and base treatment, depositing an adhesion layer on one side of the conductive substrate, and depositing an active electrode layer on the adhesion layer. The method can also comprise singulating the conductive substrate covered by the adhesion layer and the active electrode layer to yield an active sensor sized to cover a window opening defined along a chamber lateral wall of a sample container. The method can also comprise coupling the active sensor to at least part of the chamber lateral wall such that no part of the active sensor extends into a chamber cavity within the sample container and the active electrode layer faces the chamber cavity to allow any sample within the chamber cavity to be in fluid contact with the active electrode layer through at least part of the chamber lateral wall surrounding the window opening.

The method can also comprise treating the conductive substrate with nitric acid followed by treating the conductive substrate with ammonium hydroxide, isopropyl alcohol, or acetone. The method can also comprise laser cutting, metal shearing, hot wire cutting, dye cutting, stamping, or sawing the conductive substrate.

The method can also comprise applying a bead of adhesive to a part of the chamber lateral wall within a recessed portion defined along the chamber lateral wall surrounding the window opening. The method can also comprise pressing the active sensor onto the bead of adhesive within the recessed portion and curing the adhesive.

The method can also comprise insert-molding the active sensor into the chamber lateral wall while the sample container is formed by injection molding. The method can also comprise focally melting a part of the chamber lateral wall surrounding the window opening, pressing the active sensor onto the melted part of the chamber lateral wall, and allowing the melted part of the chamber lateral wall to cool to affix the active sensor to the chamber lateral wall.

The method can also comprise depositing an active electrode material making up the active electrode layer until a thickness of the active electrode layer is at least 50 nm. In some embodiments, the method can comprise depositing an active electrode material making up the active electrode layer until a thickness of the active electrode layer is at least 400 nm. In some embodiments, the active electrode material can be platinum when the solution characteristic measured is an oxidation reduction potential (ORP) of the sample. The active electrode material can be deposited using sputter deposition, evaporation deposition, electrodeposition, or ink screen-printing.

The method can also comprise depositing an adhesion material making up the adhesion layer using sputter deposition. The adhesion layer can be deposited in a vacuum chamber and the active electrode layer can be deposited subsequent to the adhesion layer in the same vacuum chamber.

The active electrode material can be a metal oxide when the solution characteristic measured is a pH of the sample. In some embodiments, the metal oxide can be platinum oxide and the platinum oxide can cover a platinum layer deposited on the adhesion layer.

In some embodiments, a method of making a sensor apparatus for measuring a solution characteristic of a sample can comprise providing a non-conductive printed circuit board (PCB) substrate and depositing an active electrode layer on one side of the PCB substrate. The active electrode layer, after the deposition step, can be electrically coupled to conductive contacts of the PCB substrate by conductive vias extending through the PCB substrate. The method can also comprise singulating the PCB substrate covered by the active electrode layer to yield an active sensor sized to cover a window opening defined along a chamber lateral wall of a sample container. The active sensor can comprise at least one conductive via extending through the PCB substrate. The method can also comprise coupling the active sensor to at least part of the chamber lateral wall such that no part of the active sensor extends into a chamber cavity within the sample container and the active electrode layer faces the chamber cavity to allow any sample within the chamber cavity to be in fluid contact with the active electrode layer through at least part of the chamber lateral wall surrounding the window opening.

The method can also comprise depositing an active electrode material making up the active electrode layer using sputter deposition, evaporation deposition, and electrodeposition. An active electrode material can be deposited until a thickness of the active electrode layer is at least 50 nm. In certain embodiments, the active electrode material can be deposited until a thickness of the active electrode layer is at least 400 nm. The active electrode material can be platinum or gold when the solution characteristic measured is an oxidation reduction potential (ORP) of the sample. The conductive contacts can be made in part of gold.

In some embodiments, another method of making a sensor apparatus can comprise providing a non-conductive polymeric substrate comprising a plurality of through-holes and depositing a conductive layer on one side of the polymeric substrate. The method can also comprise depositing an active electrode layer on the other side of the polymeric substrate. One end of each of the through-holes can be covered by the active electrode layer and the other end of each of the through-holes can be covered by the conductive layer. The active electrode layer, after the deposition steps, can be electrically coupled to the conductive layer via a conductive coating covering lateral sides of the through-holes. The method can also comprise singulating the polymeric substrate covered by the active electrode layer and the conductive layer to yield an active sensor sized to cover a window opening defined along a chamber lateral wall of a sample container. The active sensor can comprise at least one through-hole covered by the active electrode layer and the conductive layer.

The method can also comprise coupling the active sensor to at least part of the chamber lateral wall such that no part of the active sensor extends into a chamber cavity within the sample container and the active electrode layer faces the chamber cavity to allow any sample within the chamber cavity to be in fluid contact with the active electrode layer through at least part of the chamber lateral wall surrounding the window opening. Depositing the conductive layer can comprise depositing a conductive material on the other side of the polymeric substrate. In some embodiments, the conductive material can be gold.

Also disclosed is a system and method of preparing a standardized inoculum for downstream testing. The method can comprise diluting an aliquot of a source sample comprising an infectious agent to yield a diluted sample.

The source sample can be a bacterial culture or a re-suspended bacterial culture derived from a bodily fluid or swab obtained from a subject that has tested positive for bacterial growth. In some embodiments, the bodily fluid can be blood and the source sample can comprise blood cells (e.g., red blood cells). The source sample can be a bacterial culture or a re-suspended bacterial culture derived from the blood of the subject that tested positive for bacterial growth between 1 hour and 12 hours prior.

The step of diluting the aliquot of the source sample can further comprise diluting the aliquot of the sample using growth media by a dilution factor of between about 1:1 to about 1:10. The dilution factor can also be between about 1:10 to about 1:100. For example, the dilution factor can be about 1:30.

The method can further comprise detaching a container cap of a sensor apparatus from a sample container of the sensor apparatus and introducing the diluted sample into a chamber cavity of the sample container. At least part of the container cap can serve as a reference sensor. In some embodiments, the method can also comprise cleaning the sample container using an alcohol-based disinfectant solution with sonication prior to introducing the diluted sample into the sample container.

The method can also comprise coupling the container cap to the sample container and placing the sensor apparatus into a reader or reader apparatus. Certain readout components of the reader apparatus can be in electrical contact with the active sensor and the reference sensor when the sensor apparatus is placed within the reader apparatus.

The method can further comprise receiving a user input at the reader apparatus identifying a species of the infectious agent within the source sample and the reader apparatus can then retrieve a species-specific look-up table from a database based on the species identified. The species-specific look-up table can be used to set certain threshold amounts related to the solution characteristic of the diluted sample within the sensor apparatus based on a desired concentration of the standardized inoculum.

In some embodiments, the species-specific look-up table can be generated from multiple strain-specific look-up tables representing data obtained from multiple reference samples monitored over time. The multiple reference samples can comprise reference infectious agents of different strains. The reference infectious agents can be of the same species as the infectious agent within the source sample.

The method can further comprise monitoring a change in a solution characteristic of the diluted sample using the reader apparatus. The method can also comprise incubating the diluted sample partly using a heating block within the reader during the monitoring step.

The method can also comprise generating an alert or notification, via the reader apparatus or a computing device in communication with the reader apparatus, when the solution characteristic changes by a threshold amount to indicate successful preparation of the standardized inoculum from the diluted sample. The method can further comprise cooling the standardized inoculum within the sample container to a cooling temperature using a cooling component within the reader apparatus.

In some embodiments, the standardized inoculum can be a 0.5 McFarland inoculum comprising between about $1*10^8$ to about $2*10^8$ colony forming units per milliliters (CFU/mL) of bacteria. The reader apparatus can receive a user input applied to the reader apparatus to set the desired concentration or cell density (e.g., 0.5 McFarland) of the standardized inoculum during or prior to the monitoring step. The amount of time elapsed between the dilution step and the alert or notification generation step can be between about 60 minutes and 120 minutes.

Disclosed is also a system for preparing a standardized inoculum for downstream testing. The system can comprise a sensor apparatus comprising a sample container comprising a chamber cavity configured to receive a diluted sample comprising an infectious agent. The chamber cavity can be surrounded by a chamber lateral wall. The sample container can comprise an active sensor coupled to at least part of the chamber lateral wall at a window opening defined along the chamber lateral wall.

In certain embodiments, no part of the active sensor extends into the chamber cavity. The sample container can be configured to allow the diluted sample within the chamber cavity to be in fluid contact with the active sensor through at least part of the chamber lateral wall surrounding the window opening.

The active sensor can be hermetically sealed using film assisted molding except for a portion of an active electrode layer of the active sensor left exposed. The portion of the active electrode layer left exposed can be positioned to face the chamber cavity to allow the diluted sample within the chamber cavity to be in fluid contact with the portion of the active electrode layer left exposed.

In some embodiments, the active sensor can be covered in part by an active electrode layer. When the solution characteristic monitored is an oxidation reduction potential, the active electrode layer can be a platinum layer. Alternatively, when the solution characteristic monitored is pH, the active electrode layer can be a pH-sensitive layer.

The system can further comprise a container cap configured to be attached or otherwise coupled to the sample container when the chamber cavity is filled with the diluted sample. At least part of the container cap can serve as a reference sensor.

The reference sensor can comprise a reference electrode material and a wick extending through the container cap and into the chamber cavity. At least some of the diluted sample can be drawn by the wick in a direction of the reference electrode material.

The system can also comprise a reader or reader apparatus configured to receive the sensor apparatus when the container cap is coupled to the filled sample container. The reader apparatus can be configured to be in electrical contact with the active sensor and the reference sensor when the sensor apparatus is placed within the reader.

The reader apparatus can comprise one or more processors and a memory. The one or more processors can be programmed to execute instructions stored in the memory to monitor a change in a solution characteristic of the diluted sample and generate an alert or notification, via a display of the reader or a computing device in communication with the reader, when the solution characteristic changes by a threshold amount to indicate successful preparation of the standardized inoculum from the diluted sample.

The reader apparatus can also comprise a heating block configured to incubate the diluted sample while the solution characteristic of the diluted sample is being monitored. The reader apparatus can further comprise a cooling component configured to cool the standardized inoculum within the sample container to a cooling temperature.

BRIEF DESCRIPTION OF THE DRAWINGS

FIG. 1A illustrates a front view of one embodiment of a sensor apparatus for measuring a solution characteristic of a sample.

FIG. 1B illustrates a cross-sectional side view of part of the sensor apparatus.

FIG. 1C illustrates a perspective close-up view of an active sensor of the sensor apparatus adhered to a chamber lateral wall of the sensor apparatus.

FIGS. 22A and 22B illustrate the results of periodic colony counts conducted on PBCs incubated at 20° C. and 37° C., respectively.

FIGS. 22C and 22D illustrate concentration ranges of standardized inocula prepared from the PBCs indicated in FIGS. 22A and 22B.

DETAILED DESCRIPTION

Figure 1D:
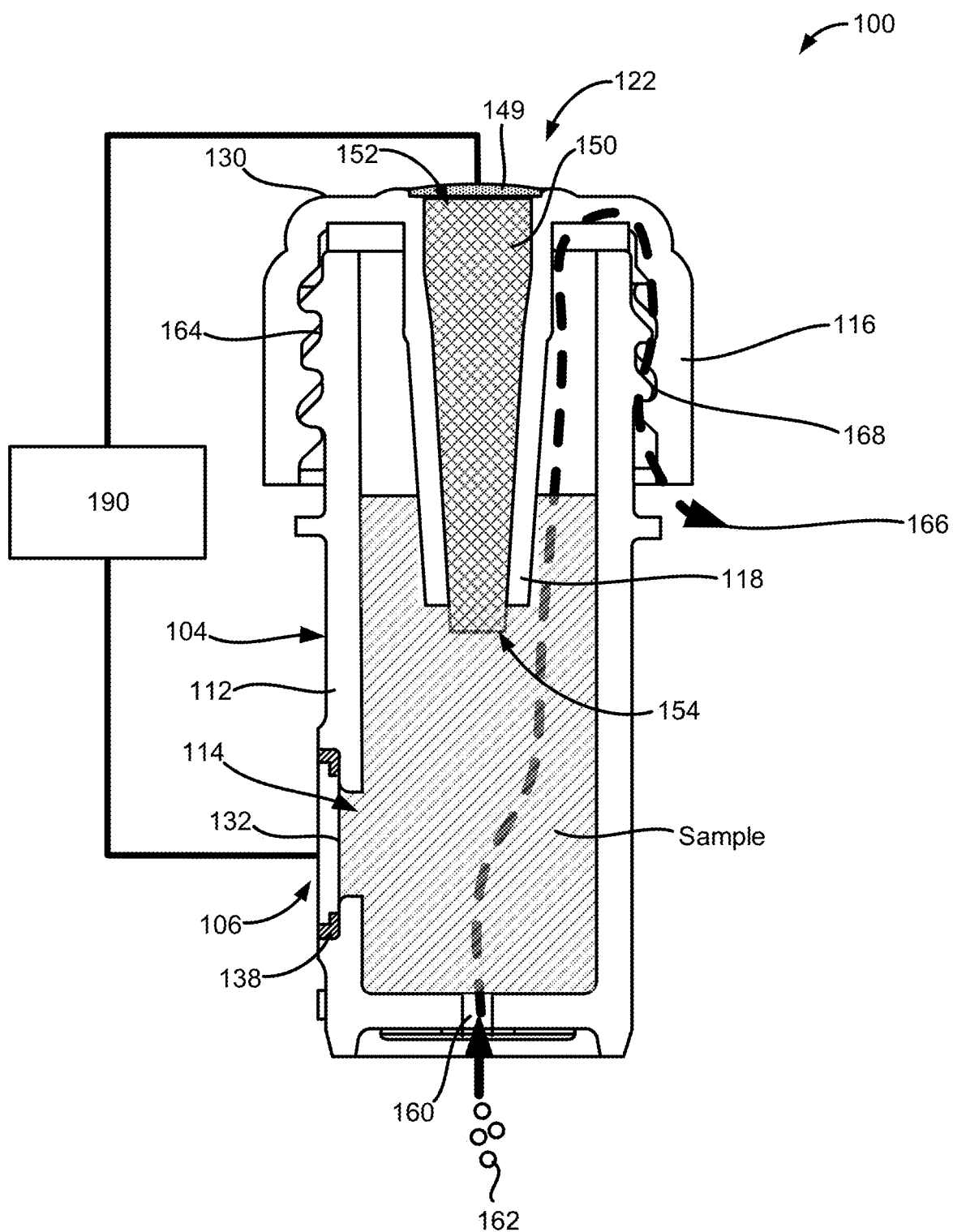
FIG. 1D illustrates a sectional view of a sample-filled sensor apparatus.

Variations of the devices, systems, and methods described herein are best understood from the detailed description when read in conjunction with the accompanying drawings. It is emphasized that, according to common practice, the various features of the drawings may not be to scale. The dimensions of certain features have been expanded or reduced for clarity and not all features may be visible or labeled in every drawing. The drawings are taken for illustrative purposes only and are not intended to define or limit the scope of the claims to that which is shown.

FIGS. 1A-1D illustrate embodiments of a sensor apparatus 100 for measuring a solution characteristic of a sample. In some embodiments, the solution characteristic measured can be an oxidation reduction potential (ORP) of the sample. In other embodiments, the solution characteristic measured can be a pH of the sample.

In some embodiments, the sample can be obtained from a patient or subject. In other embodiments, the sample can be a biological sample, an environmental sample, or a food sample.

When the sample is obtained from a patient or subject, the sample can comprise at least one of a bodily fluid of the patient or subject and a swab obtained from the patient or subject.

In some embodiments, the patient or subject can be a human patient or subject. In other embodiments, the patient or subject can be a non-human animal patient or subject.

In some embodiments, the bodily fluid can comprise blood, urine, serum, plasma, saliva, sputum, semen, breast milk, joint fluid, spinal fluid such as cerebrospinal fluid, wound material, mucus, fluid accompanying stool, vaginal secretions, synovial fluid, pleural fluid, peritoneal fluid, pericardial fluid, amniotic fluid, or a combination thereof.

In these and other embodiments, the swab obtained from the patient or subject can comprise a wound swab, a rectal swab, a vaginal swab, re-suspended instances of the aforementioned swabs, or a combination thereof.

In all such embodiments, the sample can comprise a number of microorganisms or infectious agents. The apparatus, systems, and methods disclosed herein can be used to assay the sample for microbial growth or lack thereof as part of a microbial quantification procedure or an antimicrobial susceptibility testing (AST) procedure.

In certain embodiments, the sample can comprise or refer to a bacterial culture derived from at least one of a sample obtained from a patient or subject, a biological sample, an environmental sample, and a food sample. For example, the sample can comprise or refer to a bacterial culture or a re-suspended bacterial culture derived from a bodily fluid or swab obtained from a patient or subject. As a more specific example, the sample can comprise a bacterial culture or a re-suspended bacterial culture derived from a bodily fluid or swab obtained from a patient or subject that has tested positive for microorganism growth.

More specifically, the sample can comprise a bacterial culture derived from blood obtained from a patient or subject that has tested positive for microorganism growth. In some embodiments, the sample can be or refer to a positive blood culture. For purposes of this disclosure, a positive blood culture can be a bacterial culture derived from blood drawn from a patient or subject that has tested positive for bacterial growth. For example, a patient can show symptoms of sepsis (e.g., high fever, chills, etc.) and blood (e.g., 5 mL to 10 mL) can be drawn from the patient and transferred into a commercial blood culturing container or vessel that contain bacterial growth media (e.g., 30 mL to 40 mL of growth media). The blood culturing container or vessel can then be incubated at 35° C.±2° C. to allow the bacteria to proliferate. If the patient's blood is contaminated with bacteria, the bacteria will replicate within the container or vessel. A blood culturing system or apparatus can then be used to monitor for bacterial growth (such as by monitoring bacterial $CO_2$ production within the container or vessel) and the system or apparatus can determine the sample as testing "positive" for bacterial growth when a critical $CO_2$ threshold has been met.

Depending on the pathogen type and growth rate, the blood culture can turn positive between 7 hours and 3 days. Such a "positive blood culture" can then be used for further downstream testing such as using any of the apparatus, systems, and methods disclosed herein.

In additional embodiments, the sample can comprise an environmental sample obtained from a stream, river, lake, ocean, contamination site, quarantine zone, an emergency area, or a combination thereof. In other embodiments, the sample can comprise a food sample obtained from a food preparation facility, a dining establishment, a waste facility, or a combination thereof.

In some embodiments, an aqueous growth media can be added to the sample prior to being introduced into a sample container 104 of the sensor apparatus 100. In other embodiments, the aqueous growth media can be added to the sample once the sample has been injected, delivered, poured, or otherwise introduced into the sample container 104.

In one embodiment, the aqueous growth media can be a glucose supplemented Mueller Hinton broth (MHG). In other embodiments, the aqueous growth media can be a solution containing bacto-tryptone, tryptic soy digest, yeast extract, beef extract, cation-adjusted Mueller Hinton Broth (CAMHB), starch, acid hydrolysate of casein, calcium chloride, magnesium chloride, sodium chloride, blood or lysed blood including lysed horse blood (LHB), CAMHB-LHB, glucose or other carbohydrates, or a combination thereof.

The microorganisms or infectious agents that can be assayed using the apparatus, methods, and systems disclosed herein can be any metabolizing single- or multi-cellular organism including bacteria and fungi. In certain embodiments, the microorganisms or infectious agents can be bacteria including, but not limited to, *Acinetobacter, Acetobacter, Actinomyces, Aerococcus, Aeromonas, Agrobacterium, Anaplasma, Azorhizobium, Azotobacter, Bacillus, Bacteroides, Bartonella, Bordetella, Borrelia, Brucella, Burkholderia, Calymmatobacterium, Campylobacter, Chlamydia, Chlamydophila, Citrobacter, Clostridium, Corynebacterium, Coxiella, Ehrlichia, Enterobacter, Enterococcus, Escherichia, Francisella, Fusobacterium, Gardnerella, Haemophilus, Helicobacter, Klebsiella, Lactobacillus, Legionella, Listeria, Methanobacterium, Microbacterium, Micrococcus, Morganella, Moraxella, Mycobacterium, Mycoplasma, Neisseria, Pandoraea, Pasteurella, Peptostreptococcus, Porphyromonas, Prevotella, Proteus, Providencia, Pseudomonas, Ralstonia, Raoultella, Rhizobium, Rickettsia, Rochalimaea, Rothia, Salmonella, Serratia, Shewanella, Shigella, Spirillum, Staphylococcus, Strenotrophomonas, Streptococcus, Streptomyces, Treponema, Vibrio, Wolbachia, Yersinia*, or a combination thereof. In other embodiments, the microorganisms or infectious agents can be one or more fungi selected from the genera *Candida* or *Cryptococcus* or mold.

Other specific bacteria that can be assayed using the methods and systems disclosed herein can comprise *Staphylococcus aureus, Staphylococcus lugdunensis*, coagulase-negative *Staphylococcus* species (including but not limited to *Staphylococcus epidermidis, Staphylococcus haemolyticus, Staphylococcus hominis, Staphylococcus capitis*, not differentiated), *Enterococcus faecalis, Enterococcus faecium* (including but not limited to *Enterococcus faecium* and other *Enterococcus* spp., not differentiated, excluding *Enterococcus faecalis*), *Streptococcus pneumoniae, Streptococcus pyogenes, Streptococcus agalactiae, Streptococcus* spp., (including but not limited to *Streptococcus mitis, Streptococcus pyogenes, Streptococcus gallolyticus, Streptococcus agalactiae, Streptococcus pneumoniae*, not differentiated), *Pseudomonas aeruginosa, Acinetobacter baumannii, Klebsiella aerogenes, Klebsiella* spp. (including but not limited to *Klebsiella pneumoniae, Klebsiella oxytoca*, not differentiated), *Escherichia coli, Enterobacter* spp. (including but not limited to *Enterobacter cloacae, Enterobacter aerogenes*, not differentiated), *Proteus* spp. (including but not limited to *Proteus mirabilis, Proteus vulgaris*, not differentiated), *Citrobacter* spp. (including but not limited to *Citrobacter freundii, Citrobacter koseri*, not differentiated), *Serratia marcescens, Candida albicans, Candida glabrata*, and *Candida tropicalis*.

Other more specific bacteria that can be assayed can comprise *Acinetobacter baumannii, Actinobacillus* spp., Actinomycetes, *Actinomyces* spp. (including but not limited to *Actinomyces israelii* and *Actinomyces naeslundii*), *Aeromonas* spp. (including but not limited to *Aeromonas hydrophila, Aeromonas veronii* biovar *sobria* (*Aeromonas sobria*), and *Aeromonas caviae*), *Anaplasma phagocytophilum, Alcaligenes xylosoxidans, Actinobacillus actinomycetemcomitans, Bacillus* spp. (including but not limited to *Bacillus anthracis, Bacillus cereus, Bacillus subtilis, Bacillus thuringiensis*, and *Bacillus stearothermophilus*), *Bacteroides* spp. (including but not limited to *Bacteroides fragilis*), *Bartonella* spp. (including but not limited to *Bartonella bacilliformis* and *Bartonella henselae, Bifidobacterium* spp., *Bordetella* spp. (including but not limited to *Bordetella pertussis, Bordetella parapertussis*, and *Bordetella bronchiseptica*), *Borrelia* spp. (including but not limited to *Borrelia recurrentis*, and *Borrelia burgdorferi*), *Brucella* spp. (including but not limited to *Brucella abortus, Brucella canis, Brucella melintensis* and *Brucella suis*), *Burkholderia* spp. (including but not limited to *Burkholderia pseudomallei* and *Burkholderia cepacia*), *Campylobacter* spp. (including but not limited to *Campylobacter jejuni, Campylobacter coli, Campylobacter lari* and *Campylobacter fetus*), *Capnocytophaga* spp., *Cardiobacterium hominis, Chlamydia trachomatis, Chlamydophila pneumoniae, Chlamydophila psittaci, Citrobacter* spp., *Coxiella burnetii, Corynebacterium* spp. (including but not limited to, *Corynebacterium diphtheriae, Corynebacterium jeikeum* and *Corynebacterium*), *Clostridium* spp. (including but not limited to *Clostridium perfringens, Clostridium difficile, Clostridium botulinum* and *Clostridium tetani*), *Eikenella corrodens, Enterobacter* spp. (including but not limited to *Enterobacter aerogenes, Enterobacter agglomerans, Enterobacter cloacae* and *Escherichia coli*, including opportunistic *Escherichia coli*, including but not limited to enterotoxigenic *E. coli*, enteroinvasive *E. coli*, enteropathogenic *E. coli*, enterohemorrhagic *E. coli*, enteroaggregative *E. coli* and uropathogenic *E. coli*), *Enterococcus* spp. (including but not limited to *Enterococcus faecalis* and *Enterococcus faecium*), *Ehrlichia* spp. (including but not limited to *Ehrlichia chafeensia* and *Ehrlichia canis*), *Erysipelothrix rhusiopathiae, Eubacterium* spp., *Francisella tularensis, Fusobacterium nucleatum, Gardnerella vaginalis, Gemella morbillorum, Haemophilus* spp. (including but not limited to *Haemophilus influenzae, Haemophilus ducreyi, Haemophilus aegyptius, Haemophilus parainfluenzae, Haemophilus haemolyticus* and *Haemophilus parahaemolyticus*), *Helicobacter* spp. (including but not limited to *Helicobacter pylori, Helicobacter cinaedi* and *Helicobacter fennelliae*), *Kingella kingii, Klebsiella* spp. (including but not limited to *Klebsiella pneumoniae, Klebsiella granulomatis* and *Klebsiella oxytoca*), *Lactobacillus* spp., *Listeria monocytogenes, Leptospira interrogans, Legionella pneumophila, Leptospira interrogans, Peptostreptococcus* spp., *Moraxella catarrhalis, Morganella* spp., *Mobiluncus* spp., *Micrococcus* spp., *Mycobacterium* spp.

(including but not limited to *Mycobacterium leprae, Mycobacterium tuberculosis, Mycobacterium intracellulare, Mycobacterium avium, Mycobacterium bovis*, and *Mycobacterium marinum*), *Mycoplasm* spp. (including but not limited to *Mycoplasma pneumoniae, Mycoplasma hominis*, and *Mycoplasma genitalium*), *Nocardia* spp. (including but not limited to *Nocardia asteroides, Nocardia cyriacigeorgica* and *Nocardia brasiliensis*), *Neisseria* spp. (including but not limited to *Neisseria gonorrhoeae* and *Neisseria meningitidis*), *Pasteurella multocida, Plesiomonas shigelloides, Prevotella* spp., *Porphyromonas* spp., *Prevotella melaninogenica, Proteus* spp. (including but not limited to *Proteus vulgaris* and *Proteus mirabilis*), *Providencia* spp. (including but not limited to *Providencia alcalifaciens, Providencia rettgeri* and *Providencia stuartii*), *Pseudomonas aeruginosa, Propionibacterium acnes, Rhodococcus equi, Rickettsia* spp. (including but not limited to *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* spp., *Stenotrophomonas maltophilia, Salmonella* spp. (including but not limited to *Salmonella enterica, Salmonella typhi, Salmonella paratyphi, Salmonella enteritidis, Salmonella cholerasuis* and *Salmonella typhimurium*), *Serratia* spp. (including but not limited to *Serratia marcesans* and *Serratia liquifaciens*), *Shigella* spp. (including but not limited to *Shigella dysenteriae, Shigella flexneri, Shigella boydii* and *Shigella sonnei*), *Staphylococcus* spp. (including but not limited to *Staphylococcus aureus, Staphylococcus epidermidis, Staphylococcus hemolyticus, Staphylococcus saprophyticus*), *Streptococcus* spp. (including but not limited to *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes*, Group A Streptococci, *Streptococcus pyogenes*, Group B Streptococci, *Streptococcus agalactiae*, Group C Streptococci, *Streptococcus anginosus, Streptococcus equismilis*, Group D Streptococci, *Streptococcus bovis*, Group F Streptococci, *Streptococcus anginosus*, and Group G Streptococci), *Spirillum minus, Streptobacillus moniliformi, Treponema* spp. (including but not limited to *Treponema carateum, Treponema petenue, Treponema pallidum* and *Treponema endemicum, Tropheryma whippelii, Ureaplasma urealyticum, Veillonella* spp., *Vibrio* spp. (including but not limited to *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela* and *Vibrio furnisii*), *Yersinia* spp. (including but not limited to *Yersinia enterocolitica, Yersinia pestis*, and *Yersinia pseudotuberculosis*) and *Xanthomonas maltophilia* among others.

Furthermore, other microorganisms or infectious agents that can be assayed using the methods and systems disclosed herein can comprise fungi or mold including, but not limited to, *Candida* spp. (including but not limited to *Candida albicans, Candida glabrata, Candida tropicalis, Candida parapsilosis*, and *Candida krusei*), *Aspergillus* spp. (including but not limited to *Aspergillus fumigatous, Aspergillus flavus, Aspergillus clavatus*), *Cryptococcous* spp. (including but not limited to *Cryptococcus neoformans, Cryptococcus gattii, Cryptococcus laurentii*, and *Cryptococcus albidus*), *Fusarium* spp. (including but not limited to *Fusarium oxysporum, Fusarium solani, Fusarium verticillioides*, and *Fusarium proliferatum*), *Rhizopus oryzae, Penicillium marneffei, Coccidiodes immitis*, and *Blastomyces dermatitidis*.

FIG. 1A illustrates a front view of one embodiment of a sensor apparatus 100 for measuring a solution characteristic of a sample. The sensor apparatus 100 can comprise a sample container 104, a reference sensor 122 fabricated as part of a container cap 116 (see, e.g., FIG. 1D), and an active sensor 106 coupled to at least part of the sample container 104. The container cap 116 can be removably or detachably coupled or fastened to the sample container 104 (e.g., screwed or pressed on to a top of the sample container 104).

The sample container 104 can be made in part of an inert or non-conductive material. In some embodiments, the sample container 104 can comprise or be made in part of a polymeric material, a ceramic material or glass, or a combination thereof. As a more specific example, the sample container 104 can comprise or be made in part of polyvinyl chloride (PVC), poly(methyl methacrylate) (PMMA), polydimethylsiloxane (PDMS), or a combination thereof.

FIG. 1B illustrates a cross-sectional side view of part of the sensor apparatus 100. FIG. 1B illustrates that the sample container 104 can comprise a chamber lateral wall 112 surrounding a chamber cavity 108 configured to receive a sample. The active sensor 106 can be affixed, adhered, or otherwise coupled to the chamber lateral wall 112 of the sample container 104. In other embodiments not shown in the figures, the active sensor 106 can be coupled to or otherwise positioned along a bottom of the sample container 104.

The active sensor 106 can be coupled to at least part of the chamber lateral wall 112 at a window opening 114 defined along the chamber lateral wall 112. The chamber lateral wall 112 can comprise a recessed portion 134 surrounding the window opening 114. The recessed portion 134 can be defined along an exterior side of the chamber lateral wall 112.

Regarding placement of the active sensor 106, the active sensor 106 can be configured such that no part of the active sensor 106 extends into the chamber cavity 108, as seen in FIG. 1C.

As will be discussed in more detail in the following sections, the active sensor 106 can be made of a conductive substrate covered in part by an active electrode layer 132. The active electrode layer 132 of the active sensor 106 can face the chamber cavity 108 to allow the sample within the chamber cavity 108 to be in fluid contact with the active electrode layer 132 through at least part of the chamber lateral wall 112 surrounding the window opening 114.

In some embodiments, the active sensor 106 is hermetically sealed using film assisted molding (FAM) except for a portion of the active electrode layer 132 left exposed. The wire bonds and bond pads of the active sensor 106 can be hermetically sealed using FAM. The portion of the active electrode layer 132 left exposed by the FAM can be configured or positioned to face the chamber cavity 108 to allow the sample within the chamber cavity 108 to be in fluid contact with the portion of the active electrode layer 132 left exposed.

FIG. 1C illustrates a perspective close-up view of the active sensor 106 adhered to the chamber lateral wall 112. In the embodiment shown in FIG. 1C, the active sensor 106 can be adhered to the recessed portion 134 of the chamber lateral wall 112. At least part of an active electrode layer 132 of the active sensor 106 can cover a window opening 114 defined along the chamber lateral wall 112 such that this part of the active electrode layer 132 covering the window opening 114 is positioned to be in fluid communication with the chamber cavity 108 of the sample container 104. When the sample container 104 is filled with a sample, the sample can make fluid contact with the portion of the active electrode layer 132 covering the window opening 114.

FIG. 1C also illustrates that the active sensor 106 can have its lateral sides covered by an adhesive 138. Since the active sensor 106 can comprise multiple layers, the adhesive 138 can protect certain layers of the active sensor 106 from undesired contact with the fluid sample. The adhesive 138 can act as a barrier to prevent the fluid sample from contacting the lateral sides 136 of the active sensor 106. In other embodiments not shown in the figures but contemplated by this disclosure, the recessed portion 134 of the chamber lateral wall 112 can be sized such that the active sensor 106 fits tightly within the recessed portion 134 and the walls of the recessed portion 134 adjoin or bound the lateral sides 136 of the active sensor 106. This can ensure that only the exposed portion of the active electrode layer 132 contacts the fluid sample, resulting in more accurate measurements of the solution characteristics of the fluid sample.

To adhere the active sensor 106 to the sample container 104, a bead of adhesive 138 can be applied to an inner ledge 140 and/or a side border 142 of the recessed portion 134 and the active sensor 106 can then be pressed into the recessed portion 134 with an end-effector of a pick-and-place machine. The active sensor 106 can be pressed or otherwise urged into the recessed portion 134 until an exterior-facing surface of the active sensor 106 is flush with an exterior surface of the chamber lateral wall 112.

The adhesive 138 can then be cured to secure the active sensor 106 in place. In some embodiments, the adhesive 138 can be a medical-grade UV-cured adhesive. For example, the adhesive 138 can be the Dymax® 1405M-T-UR-SC adhesive (curable using LED light at a wavelength of approximately 405 nm). In other embodiments, the adhesive 138 can be any low-outgassing medical-grade adhesive.

As previously discussed, the active sensor 106 can be made of a conductive substrate covered in part by an active electrode layer 132. The active sensor 106 can be positioned such that the active electrode layer 132 faces the chamber cavity 108 to allow the sample within the chamber cavity 108 to be in fluid contact with the active electrode layer 132 through at least part of the chamber lateral wall 112 surrounding the window opening 114. In this embodiment, the active sensor 106 (including the active electrode layer 132) is positioned radially outward from an interior-facing or cavity-facing side of the chamber lateral wall 112 and the lateral sides 136 of the active sensor 106 are not exposed to the fluid sample.

In some embodiments, the solution characteristic measured or monitored can be a pH of the sample. When the solution characteristic measured or monitored is pH, the active electrode layer 132 can be a pH-sensitive material. For example, the pH-sensitive material can be or comprise any of silicon dioxide ($SiO_2$), aluminum oxide ($Al_2O_3$), titanium dioxide ($TiO_2$), tantalum oxide/pentoxide ($Ta_2O_5$), hafnium dioxide ($HfO_2$), iridium dioxide ($IrO_2$), ruthenium dioxide ($RuO_2$), zirconium dioxide ($ZrO_2$), or a combination thereof.

In these and other embodiments, the solution characteristic measured or monitored can be an oxidation reduction potential (ORP) of the sample. When the solution characteristic measured or monitored is the ORP of the sample, the active electrode layer 132 can be a redox-sensitive material. For example, the redox-sensitive material can be or comprise any of platinum (Pt), gold (Au), a redox-sensitive metal oxide, or a combination thereof. More specifically, the redox-sensitive material can be or comprise any of silicon dioxide ($SiO_2$), aluminum oxide ($Al_2O_3$), titanium dioxide ($TiO_2$), tantalum pentoxide ($Ta_2O_5$), hafnium dioxide ($HfO_2$), iridium dioxide ($IrO_2$), ruthenium dioxide ($RuO_2$), zirconium dioxide ($ZrO_2$), or a combination thereof. Fabrication of the active sensor 106 will be discussed in more detail in later sections.

Although not shown in the figures, it is contemplated by this disclosure that the sensor apparatus 100 can be designed such that both the pH and the ORP of a sample are measured simultaneously. For example, the sample container 104 of the sensor apparatus 100 can comprise multiple window openings 114 defined along the chamber lateral walls 112 of the sample container 104. Each of these window openings 114 can then be covered by a different active sensor 106 (for example, one window opening 114 can be covered by an active sensor 106 having an active electrode layer 132 made of a redox-sensitive material and another window opening 114 can be covered by an active sensor 106 having an active electrode layer 132 made of a pH-sensitive material).

The sensor apparatus 100 can have an apparatus height. In some embodiments, the apparatus height can be between about 20.0 mm to about 50.0 mm. In other embodiments, the apparatus height can be between about 25.0 mm to about 35.0 mm. For example, the apparatus height can be about 31.3 mm.

FIG. 1D illustrates that the reference sensor 122 can be fabricated as part of a container cap 116. The reference sensor 122 can comprise a reference conduit 118 comprising a reference conduit cavity 120 (see, e.g., FIG. 1B). The reference conduit cavity 120 can have first and second openings at opposite ends of the reference conduit cavity 120. The reference conduit 118 can be an elongate channel or passageway configured to extend into the chamber cavity 108 of the sample container 104.

The reference sensor 122 can also comprise a reference electrode material 149 and a wicking component 150 in fluid communication with the chamber cavity 108. The reference conduit cavity 120 can house the wicking component 150. At least some of the sample can be drawn up by the wicking component 150 in a direction of the reference electrode material 149.

The reference conduit 118 can be tapered such that a volume of the reference conduit cavity 120 tapers or narrows from a reference conduit proximal end 126 to a reference conduit distal end 128 (see, e.g., FIG. 1B). The shape of the wicking component 150 can match or accommodate the shape of the reference conduit cavity 120. The wicking component 150 can be configured such that the shape of the wicking component 150 tapers or narrows from a wick proximal end 152 to a wick distal end 154.

The wicking component 150 can extend through a length of the reference conduit cavity 120. In some embodiments, the wicking component 150 can fill up or occupy all of the space within the reference conduit cavity 120. In other embodiments, the wicking component 150 can partially fill up or partially occupy the space within the reference conduit cavity 120.

At least part of the wicking component 150 can be in fluid communication with the chamber cavity 108 of the sample container 104 such that when the sample container 104 is filled with the sample, at least some of the sample in the sample container 104 is drawn up, absorbed, or otherwise wicked by at least a portion of the wick distal end 154 in a direction of the wick proximal end 152. The wicking component 150 can be made of a polymeric material that draws up the fluid sample towards the reference electrode material 149 by capillary action.

In some embodiments, at least part of the wick distal end 154 can extend past the reference conduit second opening such that the wick distal end 154 protrudes or extends into the chamber cavity 108 of the sample container 104. In these embodiments, the wick distal end 154 can extend or protrude into the sample when the sample container 104 is filled by the sample.

In other embodiments, the wick distal end 154 is positioned proximal or above the reference conduit second opening such that the wick distal end 154 does not protrude or extend into the chamber cavity 108 of the sample container 104. In these embodiments, the wick distal end 154 can still be in fluid communication with the sample container 104 and the fluid sample can still reach or contact the wick distal end 154 by being drawn up into the reference conduit 118 by capillary action or by perturbing or shaking the sample container 104.

As previously discussed, the wicking component 150 can be made in part of a porous material. The wicking component 150 can be made in part of a material comprising pores sized between 15 µm to about 150 µm (e.g., about 50 µm). In some embodiments, the wicking component 150 can be made in part of a polymeric material. As a more specific example, the wicking component 150 can be made in part of a porous polymeric material comprising pores sized between 15 µm to about 150 µm. In one embodiment, the wicking component 150 can be made in part of high-density polyethylene (HDPE). For example, the wicking component 150 can be made in part of HDPE having pores sized about 50 µm. In other embodiments, the wicking component 150 can be made in part of natural fibers. For example, the wicking component 150 can be made in part of cellulose fibers, pulp, paper, cotton, or a combination thereof.

The wicking component 150 can also be treated by a surfactant such that at least a surface of the wicking component 150 is covered by the surfactant. In some embodiments, the wicking component 150 can be saturated by the surfactant or immersed in a solution comprising the surfactant prior to being introduced into the reference conduit cavity 120. The surfactant can be configured to increase a hydrophilicity of the wicking component 150 (i.e., to make a substantially hydrophobic surface of the wicking component 150 more hydrophilic). In some embodiments, the surfactant can be a fluorosurfactant. In other embodiments, the surfactant can be a non-ionic surfactant such as one or more Poloxamers. As a more specific example, the surfactant can comprise Pluronic® F-68.

In one embodiment, the reference conduit 118 can be substantially shaped as a conic or frustoconic having a reference conduit cavity 120 also substantially shaped as a conic or frustoconic. In other embodiments, the reference conduit 118 can be substantially shaped as an elongate pyramid having a polygonal-shaped base. For example, the reference conduit 118 can be substantially shaped as an elongate triangular pyramid, square pyramid, or a pentagonal pyramid. In additional embodiments, the reference conduit 118 can be substantially shaped as a cylinder having a substantially cylindrical-shaped reference conduit cavity 120. In these embodiments, the reference conduit 118 can have a tapered reference conduit distal end 128 (see, e.g., FIG. 1B).

As shown in FIG. 1D, at least part of the wicking component 150 can be in fluid contact with the sample in the sample container 104. At least some of the sample can be drawn up by the wicking component 150 in a direction of the wick proximal end 152. The reference electrode material 149 can be disposed at the wick proximal end 152. FIG. 1D also illustrates that at least part of the active electrode layer 132 can be in fluid contact with the sample in the sample container 104. When the wicking component 150 draws or wicks up the sample, the sample can reach the reference electrode material 149 and charge carriers within the sample can establish an electrical connection between the reference electrode material 149 of the reference sensor 122 and the active electrode layer 132 of the active sensor 106. When both the reference sensor 122 and the active sensor 106 are electrically coupled to a reader apparatus 190, the reader apparatus 190 can be used to measure a solution characteristic of the sample.

The solution characteristic of the sample can be determined based on a potential difference measured between the active sensor 106 and the reference sensor 122 when the reference sensor 122 and the active sensor 106 are electrically coupled to the reader apparatus 190. For example, the reference sensor 122 can provide a stable half-cell potential compared to the active sensor 106 when both the reference electrode material 149 and the active electrode layer 132 are in fluid contact with the sample within the sample container 104.

In some embodiments, the reference electrode material 149 can be an electrically-conductive ink applied or dispensed on the wick proximal end 152. The electrically-conductive ink applied or dispensed on the wick proximal end 152 can be hardened by curing. More specifically, the electrically-conductive ink can be a silver-silver chloride (Ag—AgCl) ink.

At least part of the reference electrode material 149 can be coupled to the wicking component 150. For example, the reference electrode material 149 can be a cured and hardened mass positioned at the wick proximal end 152. In certain embodiments, the reference electrode material 149 can be positioned in the middle of the container cap 116. In some embodiments, at least part of the reference electrode material 149 can protrude or extend beyond the container cap 116.

One advantage of the wicking component 150 disclosed herein is that the wicking component 150 can draw up the sample and the sample can advance by capillary action through the pores of the wicking component 150 toward the reference electrode material 149. For example, the liquid sample can be wicked to the wick proximal end 152 where it makes fluid contact with the reference electrode material 149. When the reference electrode material 149 is made of a material such as silver-silver chloride (Ag—AgCl), the wicking component 150 can act as a barrier or hindrance to silver ions ($Ag^+$) that would otherwise diffuse freely into the sample within the sample container 104. Such silver ions can be harmful to or otherwise affect the growth of the microorganisms or infectious agents in the sample. The wicking component 150 can act as a barrier or hindrance to the harmful silver ions by slowing down or stalling the diffusion of such ions into the sample. The wicking component 150 having the dimensions and shape disclosed herein can be effective in slowing down or stalling the diffusion of such harmful ions.

When the reference sensor 122 is implemented as a container cap 116, the container cap 116 can have dimensions as defined by a cap width (or diameter) and a cap height. In some embodiments, the cap width can be between about 10.0 mm to about 20.0 mm. For example, the cap width can be about 15.7 mm. In some embodiments, the cap height can be between about 5.0 mm to about 20.0 mm. For example, the cap height can be about 10.5 mm. When the container cap 116 is fastened, affixed, or otherwise coupled to the sample container 104, the sensor apparatus 100 can have an apparatus height as measured from a bottom of the sample container 104 to a cap top 130 of the container cap 116.

The wicking component 150 can have a wick height as measured from the wick proximal end 152 to the wick distal end. In some embodiments, the wick height can be between about 10.0 mm to about 20.0 mm More specifically, the wick height can be between about 14.0 mm to about 15.0 mm. For example, the wick height can be about 14.8 mm.

As illustrated in FIG. 1D, the reference electrode material 149 can be positioned or disposed, at least partially, within a divot, depression, or concave region in a center of the container cap 116 above the wicking component 150. When the reference sensor 122 is a cured or hardened electrically-conductive ink or solution (e.g., Ag—AgCl ink), the divot, depression, or concave region can act as a receiving space for the liquid ink or solution to be cured.

In some embodiments, the reference electrode material 149 can have a reference electrode height and a reference electrode width. The reference electrode height can be between about 0.2 mm and 1.0 mm. For example, the reference electrode height can be about 0.4 mm. The reference electrode width can be between about 2.0 mm to about 5.0 mm. For example, the reference electrode width can be about 3.0 mm One advantage of the reference sensor 122 disclosed herein is that the reference sensor 122 can act as a stable reference electrode or provide a stable reference potential for up to 10-hours of testing or operation.

FIG. 1D also illustrates that the sensor apparatus 100 can comprise an aeration port 160 defined along a bottom side of the sample container 104. In other embodiments not shown in the figures, the aeration port 160 can be defined along the chamber lateral wall 112 of the sample container 104.

The aeration port 160 can be covered by a first air-permeable membrane. The aeration port 160 and the first air-permeable membrane can be configured to allow a gas 162 to enter the sample container 104.

In some embodiments, the gas 162 can be ambient air (e.g., the air in a laboratory, clinical setting, or testing facility). In other embodiments, the gas 162 can comprise a combination of pressurized oxygen, carbon dioxide, nitrogen, and argon. Aerating the sample can accelerate the growth of a microbial population within the sample by providing an oxygen rich environment within the sample container 104.

In alternative embodiments not shown in the figures, the aeration port 160 can be defined along a cap top 130 of the container cap 116 and the gas 162 can be pumped into the sample container 104 from the top of the sample container 104.

The gas 162 (e.g., ambient air) can be pumped into the sample container 104 by a micropump or another pump-type device integrated within the reader apparatus 190. The gas 162 (e.g., ambient air) can be pumped or otherwise directed into the sample container 104 through the aeration port 160 and the first air-permeable membrane at a constant flow rate of between about 1.0 and 10.0 mL/min. In other embodiments, the gas 162 (e.g., ambient air) can be pumped or otherwise directed into the sample container 104 through the aeration port 160 and the first air-permeable membrane at specific duty cycles or intervals.

In certain embodiments, a second air-permeable membrane can cover at least part of an underside of the container cap 116. The second air-permeable membrane can allow any gas 162 pumped or otherwise introduced into the sample container 104 to exit the sample container 104 while also preventing any liquid within the sample container 104 from spilling out of the sample container 104.

In some embodiments, the first air-permeable membrane and the second air-permeable membrane can be made of the same material. The first air-permeable membrane and the second air-permeable membrane can be made of a hydrophobic air-permeable film or thin-sheet. For example, the first air-permeable membrane and the second air-permeable membrane can both be made of or comprise polytetrafluoroethylene (PTFE).

As shown in FIG. 1D, the container cap 116 can be removably or detachably coupled or fastened to the sample container 104 by being screwed on to a proximal portion of the sample container 104 via a threaded connection 164. When the container cap 116 (serving as part of the reference sensor 122) is fastened or coupled to the sample container 104 by the threaded connection 164, an airflow pathway 166 can be created as air enters the aeration port 160 through the first air-permeable membrane into the sample container 104. The air then exits the sample container 104 through the second air-permeable membrane and air gaps 168 defined in between the threads of the container cap 116 and the sample container 104.

The container cap 116 can be made in part of a transparent or clear material or a transparent or clear non-conducting material. In other embodiments, the container cap 116 can be made in part of a translucent or see-through material. For example, at least part of the wicking component 150 can be visible through the sides of the container cap 116. This can allow a user or operator of the sensor apparatus 100 to observe the wicking of the fluid sample from the wick distal end 154 to the wick proximal end 152 when the container cap 116 is fastened to the sample container 104 and ensure that at least some of the sample is able to reach the reference electrode material 149 at the wick proximal end 152. In some embodiments, the container cap 116 can be made in part of a clear or transparent polymeric material, glass, or a combination thereof.

In some embodiments, the sample container 104, the container cap 116, or a combination thereof can be made in part of an inert polymeric material. For example, the sample container 104, the container cap 116, or a combination thereof can be made in part of at least one of polycarbonate, polyoxymethylene, polyamide, polyethylene, acrylonitrile butadiene styrene, polypropylene, or co-polymers or composites thereof. In other embodiments, the sample container 104, the container cap 116, or a combination thereof can be made in part a glass material such as borosilicate glass or a ceramic material.

In additional embodiments, the container cap 116 can be any of the reference electrode container caps disclosed in U.S. Patent Publication No. US2021/0131993 published on May 6, 2021, the content of which is hereby incorporated by reference in its entirety.

Figure 2:
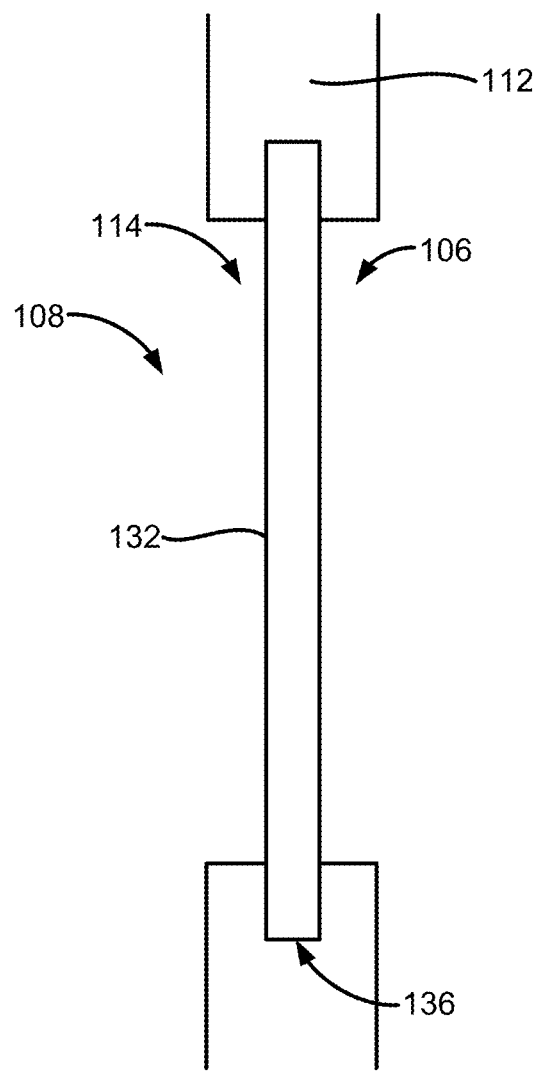
FIG. 2 illustrates an embodiment of an active sensor of the sensor apparatus insert molded into a chamber lateral wall of the sensor apparatus.

FIG. 2 illustrates that the active sensor 106 can also be insert molded into part of the chamber lateral wall 112 when the sample container 104 is made of a polymeric material. For example, the active sensor 106 can be insert-molded into the chamber lateral wall 112 while the sample container 104 is being formed by injection molding.

When the active sensor 106 is inserted molded into part of the chamber lateral wall 112 of the sample container 104, the active sensor 106 can have its lateral sides 136 encapsulated by the polymeric material used to make the chamber lateral wall 112.

In the embodiment shown in FIG. 2, the active sensor 106 can be insert molded such that the active electrode layer 132 faces the chamber cavity 108 to allow the sample within the chamber cavity 108 to be in fluid contact with the active electrode layer 132 through at least part of the chamber lateral wall 112 surrounding the window opening 114.

Figure 3A:
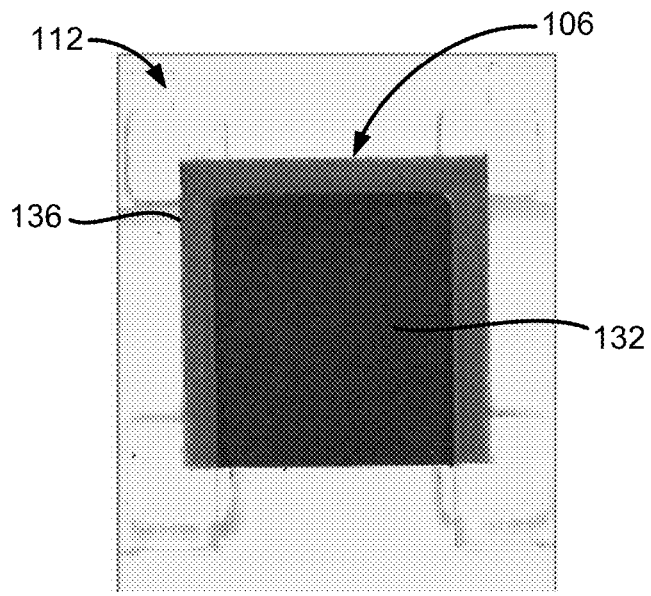
FIG. 3A is a black-and-white image of a top plan view of a side of the active sensor covered by an active electrode layer. The active sensor is molded into part of the chamber lateral wall in this image.
Figure 3B:
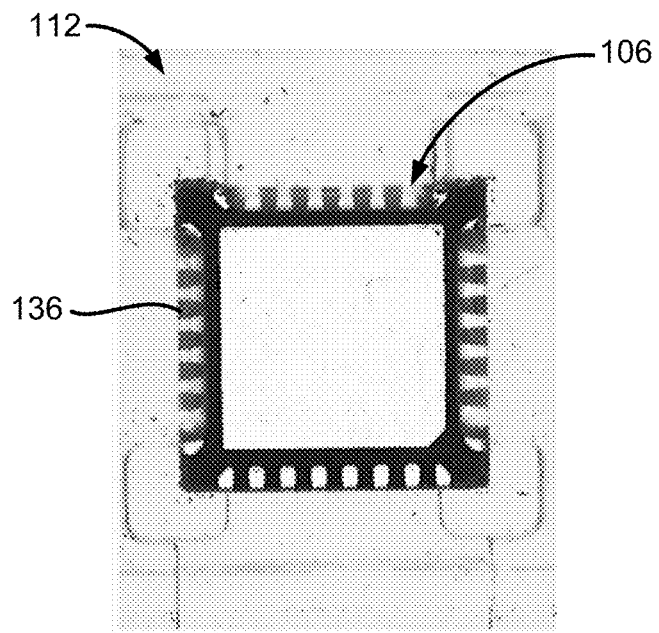
FIG. 3B is a black-and-white image of the opposite side of the active sensor shown in FIG. 3A. The active sensor is molded into part of the chamber lateral wall in this image.

FIGS. 3A and 3B are black-and-white images of an active sensor 106 insert molded into a polymeric material representing the material used to construct the chamber lateral wall 112 of the sample container 104 (see, e.g., FIGS. 1A-1D). In some embodiments, the sample container 104 can be made in part of an inert polymeric material such as polycarbonate, polyoxymethylene, polyamide, polyethylene, acrylonitrile butadiene styrene, or polypropylene.

FIG. 3A shows a top plan view of the side of the active sensor 106 covered by the active electrode layer 132. As previously discussed, the active sensor 106 can be insert molded such that the active electrode layer 132 faces the chamber cavity 108 to allow the sample within the chamber cavity 108 (see, e.g., FIG. 1D) to be in fluid contact with an exposed region of the active electrode layer 132.

FIG. 3B shows a top plan view of a side of the active sensor 106 opposite the active electrode layer 132. The side of the active sensor 106 shown in FIG. 3B can be used to contact the conductive connections of the reader apparatus 190 (see, e.g., FIGS. 14 and 15). As will be discussed in more detail in the following sections, this side of the active sensor 106 can be referred to as a conductive layer.

As shown in FIGS. 3A and 3B, the lateral sides 136 of the active sensor 106 can be encapsulated by the polymeric material. This can ensure that only the exposed portion of the active electrode layer 132 contacts the fluid sample within the sample container 104, resulting in more accurate measurements of the solution characteristics of the fluid sample.

Although not shown in the figures, it is contemplated by this disclosure that the active sensor 106 can be affixed or otherwise coupled to the chamber lateral wall 112 by focally melting (e.g., by ultrasonic welding) a portion of the chamber lateral wall 112 surrounding the window opening 114 (see, e.g., FIGS. 1B-1D for the location of the window opening 114) and pressing the active sensor 106 onto the melted portion of the chamber lateral wall 112. Once the melted portion of the chamber lateral wall 112 cools, the active sensor 106 is now affixed or coupled to the chamber lateral wall 112.

Figure 4A:
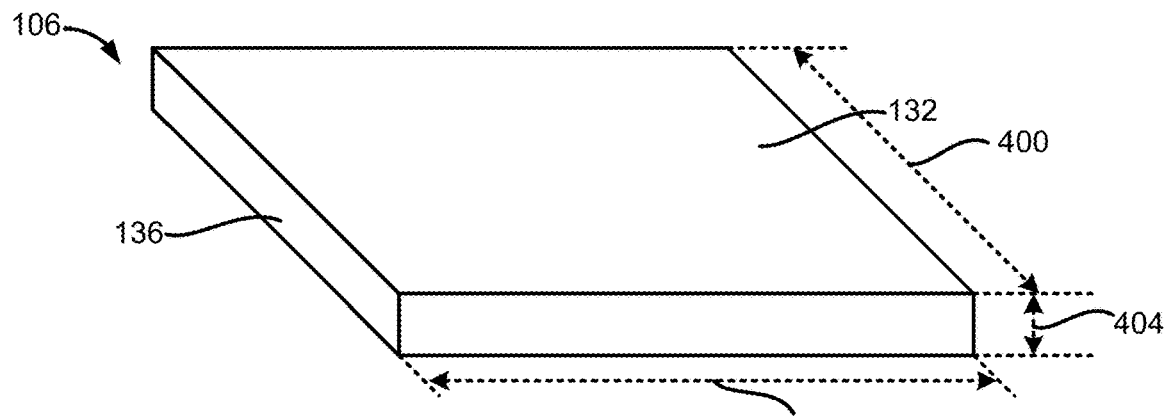
FIG. 4A illustrates a perspective view of one embodiment of an active sensor.

FIG. 4A illustrates a perspective view of one embodiment of an active sensor 106 with two of its lateral sides 136 visible. As shown in FIG. 4A, the active sensor 106 can be substantially shaped as a flattened or truncated rectangular prism. In other embodiments, the active sensor 106 can be substantially disk-shaped or shaped as a flattened or truncated polygonal prism (e.g., a flattened or truncated pentagonal prism or hexagonal prism).

FIG. 4A also illustrates that when the active sensor 106 is substantially shaped as a rectangular prism, the active sensor 106 can have a sensor length dimension 400, a sensor width dimension 402, and a sensor height dimension 404. In some embodiments, the sensor length dimension 400 can be between about 100 µm and 6.0 mm, the sensor width dimension 402 can be between about 100 µm and 6.0 mm, and the sensor height dimension 404 can be between about 10 µm and 0.70 mm. For example, when the active sensor 106 is substantially shaped as a rectangular prism, the active sensor 106 can have a sensor length dimension 400 of about 6.0 mm, a sensor width dimension 402 of about 6.0 mm, and a sensor height dimension 404 of about 0.61 mm.

Figure 4B:
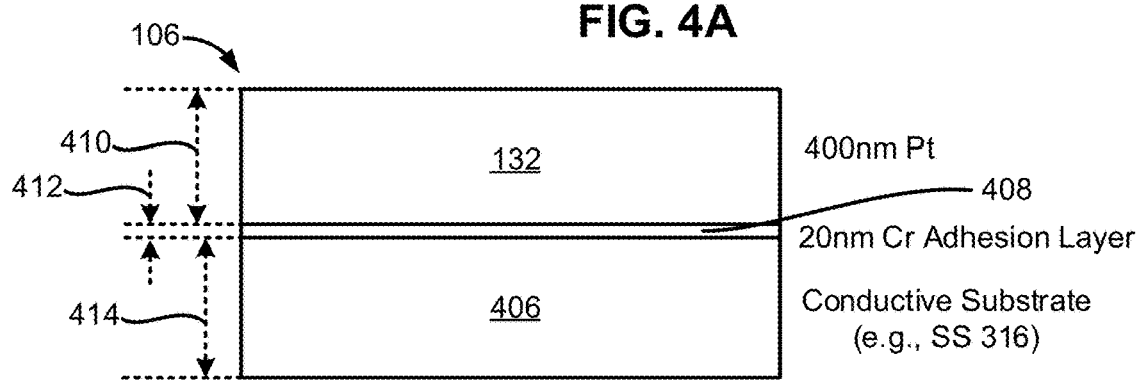
FIG. 4B illustrates a side view of one embodiment of an active sensor used for measuring ORP.

FIG. 4B illustrates a side view of one embodiment of an active sensor 106 used for measuring an oxidation reduction potential (ORP) of a sample. In this embodiment, the active sensor 106 can have an active electrode layer 132 made of a noble metal. For example, the active electrode layer 132 can be made of platinum, gold, or a combination or composite thereof.

The active electrode layer 132 can be adhered to one side of a conductive substrate 406 via an adhesion layer 408. The conductive substrate 406 can be made of a conductive material such as stainless steel (SS). For example, the conductive substrate 406 can be SS 316. In other embodiments, the conductive substrate 406 can be made of aluminum, copper, or any combination or composite of aluminum, copper, or stainless steel.

In some embodiments, the adhesion layer 408 can be a thin layer of chromium (Cr). Alternatively, the adhesion layer 408 can be a thin layer of gold, nickel, titanium or tantalum. The adhesion layer 408 can be disposed in between the conductive substrate 406 and the active electrode layer 132.

In alternative embodiments, the active electrode layer 132 can be deposited directly onto one side of the conductive substrate 406 without an adhesion layer 408.

The active electrode layer 132 can have an active electrode layer thickness 410 of between about 50 nm and 500 nm (e.g., about 400 nm). The adhesion layer 408 can have an adhesion layer thickness 412 of between about 5 nm and 50 nm (e.g., about 20 nm). A ratio of the adhesion layer thickness 412 to the active electrode layer thickness 410 can be between about 1:10 and 1:20.

The conductive substrate 406 can have a substrate layer thickness 414. The substrate layer thickness can be between about 10 µm and 0.70 mm (e.g., about 0.61 mm).

Figure 4C:
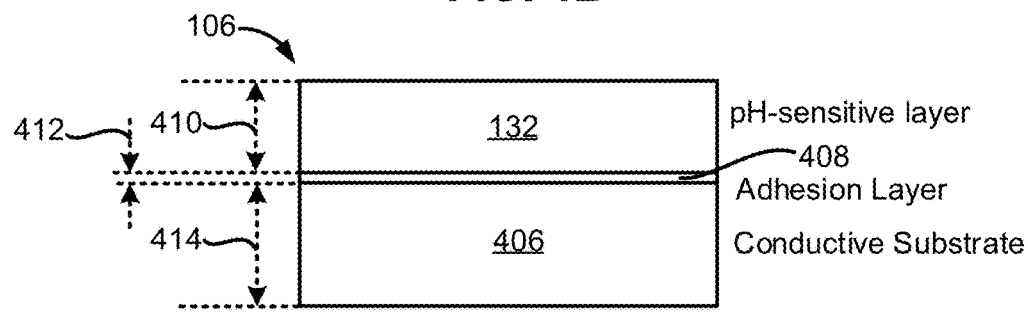
FIG. 4C illustrates a side view of another embodiment of an active sensor used for measuring pH.

FIG. 4C illustrates a side view of another embodiment of an active sensor 106 used for measuring a pH of a sample. In this embodiment, the active sensor 106 can have an active electrode layer 132 made of a pH-sensitive material. The pH-sensitive material can be deposited as a layer directly onto the conductive substrate 406 or via an adhesion layer 408.

For example, the active electrode layer 132 can be made of a metal oxide. For example, the active electrode layer 132 can be made of tantalum pentoxide ($Ta_2O_5$). In other embodiments, the active electrode layer 132 can be made of silicon dioxide ($SiO_2$), silicon nitride ($Si_3N_4$), aluminum oxide ($Al_2O_3$), titanium dioxide ($TiO_2$), hafnium dioxide (HfO$_2$), iridium dioxide (IrO$_2$), ruthenium dioxide (RuO$_2$), zirconium dioxide (ZrO$_2$), or a combination or composite thereof.

The conductive substrate 406 can be made of a conductive material such as stainless steel (SS). For example, the conductive material can be SS 316. In other embodiments, the conductive substrate 406 can be made of aluminum, copper, or any combination or composite of aluminum, copper, or stainless steel.

In some embodiments, the adhesion layer 408 can be a thin layer of chromium (Cr). Alternatively, the adhesion layer 408 can be a thin layer of gold, nickel, titanium or tantalum. The adhesion layer 408 can be disposed in between the conductive substrate 406 and the active electrode layer 132.

As previously discussed, the active electrode layer 132 can be deposited directly onto the conductive substrate 406 without an adhesion layer 408.

The active electrode layer 132 can have an active electrode layer thickness 410 of between about 50 nm and 500 nm (e.g., about 400 nm). The adhesion layer 408 can have an adhesion layer thickness 412 of between about 5 nm and 50 nm (e.g., about 20 nm). A ratio of the adhesion layer thickness 412 to the active electrode layer thickness 410 can be between about 1:10 and 1:20.

The conductive substrate 406 can have a substrate layer thickness 414. The substrate layer thickness can be between about 10 μm and 0.70 mm (e.g., about 0.61 mm).

Figure 4D:
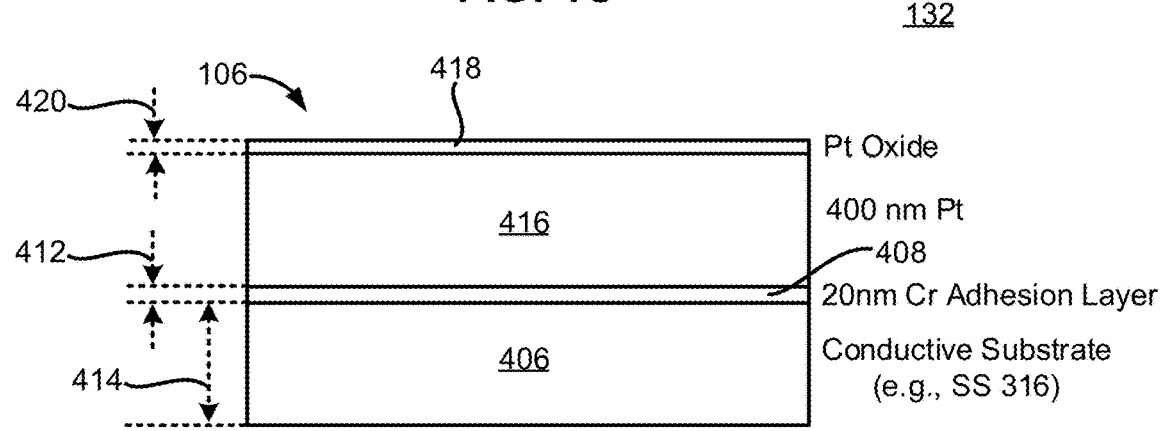
FIG. 4D illustrates a side view of another embodiment of an active sensor used for measuring pH.

FIG. 4D illustrates a side view of another embodiment of an active sensor 106 used for measuring a pH of a sample. In this embodiment, a surface modification technique can be used to modify a platinum layer 416. For example, an oxygen plasma treatment can be used to oxidize the platinum layer 416 to create a platinum oxide/dioxide (PtO$_2$) layer 418. The platinum oxide layer 418 thus formed can respond to hydrogen ions and be used as a pH-sensitive layer. In this manner, the platinum oxide layer 418 can act as the active electrode layer 132.

The platinum layer 416 can be adhered to a conductive substrate 406 via an adhesion layer 408. The conductive substrate 406 can be made of a conductive material such as stainless steel (SS). For example, the conductive substrate can be SS 316. In other embodiments, the conductive substrate 406 can be made of aluminum, copper, or any combination or composite of aluminum, copper, or stainless steel.

In some embodiments, the adhesion layer 408 can be a thin layer of chromium (Cr). Alternatively, the adhesion layer 408 can be a thin layer of gold, nickel, titanium, or tantalum. The adhesion layer 408 can be disposed in between the conductive substrate 406 and the active electrode layer 132.

In alternative embodiments, the platinum layer 416 can be deposited directly onto one side of the conductive substrate 406 without an adhesion layer 408.

The platinum layer 416 can have a layer thickness of between about 50 nm and 500 nm (e.g., about 400 nm). The adhesion layer 408 can have an adhesion layer thickness 412 of between about 5 nm and 50 nm (e.g., about 20 nm).

The conductive substrate 406 can have a substrate layer thickness 414. The substrate layer thickness can be between about 10 μm and 0.70 mm (e.g., about 0.61 mm).

The platinum oxide layer 418 can have an oxide layer thickness 420. The oxide layer thickness 420 can be between about 10 nm and 100 nm.

As previously discussed, the deposited layers can be selected to achieve a certain desired sensitivity or specificity towards a particular analyte. Other surface modification techniques such as self-assembled monolayers (SAMs), bio-functionalization with antibodies, binding antibody fragments, binding aptamers, binding DNA, and plasma treatments can also be employed to alter the surface properties of the deposited layers and thereby tune their specificity and sensitivity.

Figure 5A:
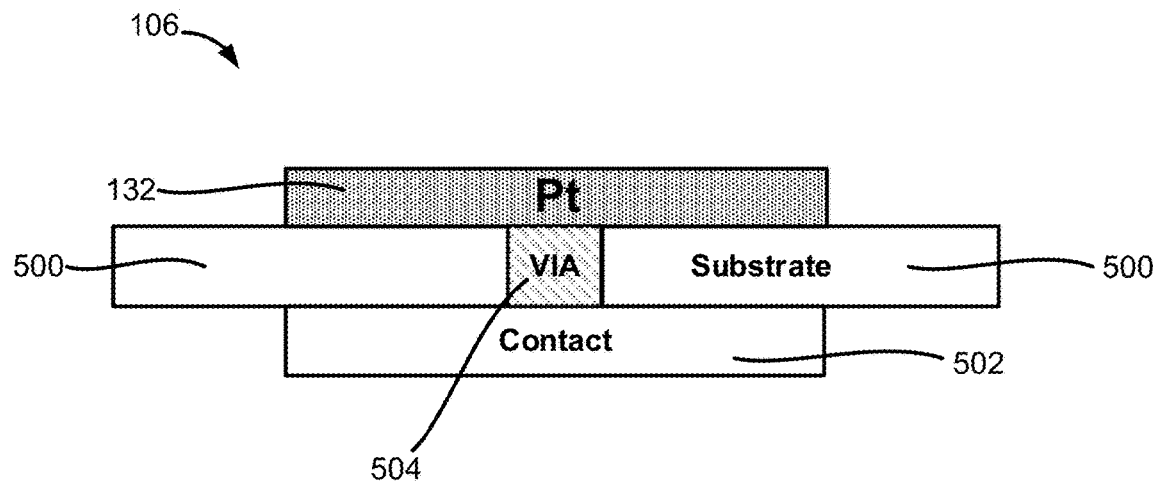
FIG. 5A illustrates a side view of another embodiment of an active sensor made using a PCB substrate.

FIG. 5A illustrates a side view of yet another embodiment of an active sensor 106. This embodiment of the active sensor 106 leverages the scale and efficiency of printed circuit board (PCB) manufacturing techniques.

The active sensor 106 can be made of a non-conductive PCB substrate 500 covered in part by an active electrode layer 132. In some embodiments, the non-conductive PCB substrate 500 can be made of polyimide. In other embodiments, the non-conductive PCB substrate 500 can be made of a glass-reinforced epoxy laminate material such as an FR-4 composite material. In certain embodiments, the PCB substrate 500 can be a flexible PCB material.

In some embodiments, the active electrode layer 132 can be made of a noble metal. For example, the active electrode layer 132 can be made of platinum (see, e.g., FIGS. 5A, 5B, and 6A-6C), gold (see, e.g., FIGS. 6A-6C), or a combination or composite thereof. The platinum or gold can be electrodeposited or sputter deposited on the PCB substrate 500.

The active electrode layer 132 can have an active electrode layer thickness of at least 50 nm. In certain embodiments, the active electrode layer 132 can have an active electrode layer thickness of at least 400 nm. When the active electrode layer 132 is made of platinum, the active sensor 106 can be used for measuring or monitoring the ORP of a sample.

In an alternative embodiment, a platinum layer deposited on the non-conductive PCB substrate 500 can be modified with a surface modification technique to turn the platinum layer into a pH-sensitive layer (see, e.g., FIG. 4D). For example, an oxygen plasma treatment can be used to oxidize the platinum layer to create a platinum oxide (PtO$_2$) layer. The platinum oxide layer thus formed can respond to hydrogen ions and be used as a pH-sensitive layer. In this embodiment, the active sensor 106 can be used to measure or monitor the pH of a sample.

The PCB substrate 500 can be patterned with conductive contacts or a conductive contact layer 502 on a side of the substrate opposite the active electrode layer 132. In some embodiments, the conductive contact layer 502 can be a gold layer. In other embodiments, the conductive contact layer 502 can be made of another type of conductive metal such as platinum, nickel, copper, or alloys or composites thereof.

As shown in FIG. 5A, the active electrode layer 132 can be electrically coupled to the conductive contacts or conductive contact layer 502 by one or more conductive vias 504. In one embodiment, the conductive vias 504 can be made in part of copper or a copper alloy. In other embodiments, the conductive vias 504 can be made of another type of conductive metal such as gold.

In some embodiments, each active sensor 106 can have at least one conductive via 504 positioned in a center of the sensor package. In other embodiments, the conductive via 504 can be positioned near a periphery or edge of the sensor package.

The conductive vias 504 can be formed by electroplating, deposition, or a combination thereof. Moreover, additional features or patterns can be formed on the PCB substrate 500 using standard PCB etching processes.

Figure 5B:
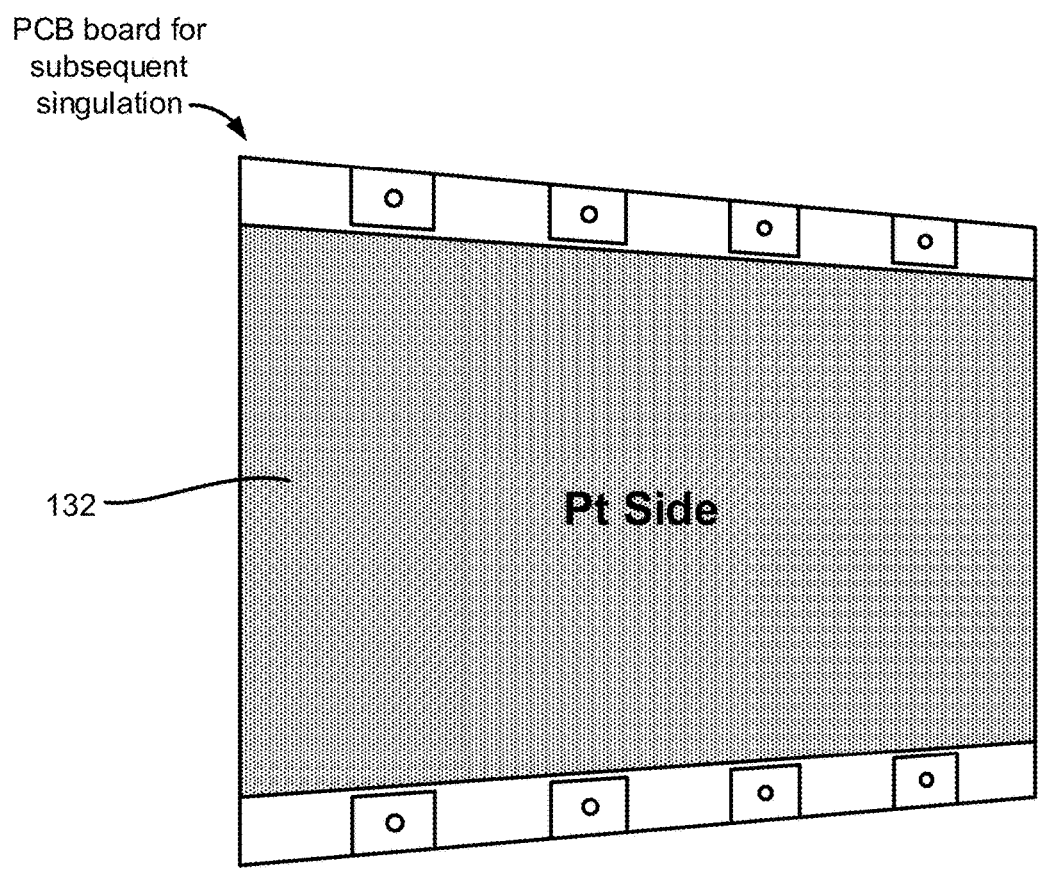
FIG. 5B illustrates a single PCB board covered by an active electrode layer that can be singulated into numerous individual active sensors.

FIG. 5B illustrates a single PCB board covered by an active electrode layer 132 (e.g., platinum) that can be singulated into numerous individual active sensors 106. For example, one PCB board can be singulated to produce between 400 and 500 active sensors 106.

Figure 6A:
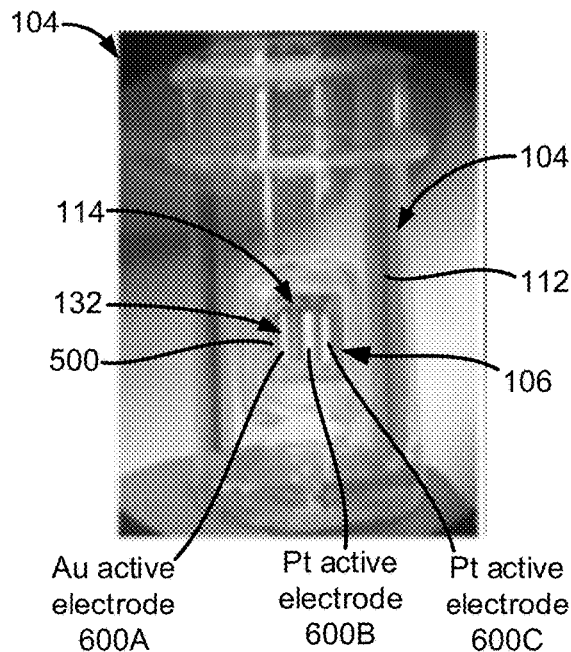
FIG. 6A is a black-and-white image showing an active sensor comprising three individual active electrodes.

FIG. 6A is a black-and-white image showing an active sensor 106 comprising three individual active electrodes including a gold (Au) active electrode 600A, a first platinum (Pt) active electrode 600B, and a second Pt active electrode 600C. The active sensor 106 can be produced using the PCB manufacturing techniques previously discussed. The only difference being that different active electrode materials (e.g., Au and Pt) were electroplated or deposited on the same non-conductive PCB substrate 500. For example, one section or strip of the non-conductive PCB substrate 500 can be covered by a first active electrode material or layer (e.g., Au) and other sections or strips of the same non-conductive PCB substrate 500 can be covered by a second active electrode material or layer (e.g., Pt).

As shown in FIG. 6A, the active sensor 106 can be coupled (e.g., adhered or insert molded) to a part of the lateral chamber wall 112 of the sample container 104. Since the sample container 104 shown in FIG. 6A is fabricated as a clear container, the active electrode side of the active sensor 106 is visible through the clear walls of the sample container 104. When the sample container 104 is filled with a fluid sample (not shown in FIG. 6A), the fluid sample can contact the gold active electrode 600A, the first platinum active electrode 600B, and the second platinum active electrode 600C through the window opening 114 defined along the chamber lateral wall 112.

One advantage of an active sensor 106 comprising multiple active electrodes is that each electrode can report a unique potential with respect to the same reference electrode or reference sensor (e.g., the reference sensor 122). Moreover, the active electrodes can be made of different materials such that different solution characteristics (e.g., ORP and pH) of the sample can be measured or monitored at the same time.

Although not shown in the figures, it is contemplated by this disclosure that an active sensor 106 made of numerous active electrodes arranged as an active electrode array (e.g., a 96 electrode array) can be integrated into a single sensor apparatus 100 to measure multiple solution characteristics of a sample at the same time. The multiple active electrodes can be patterned on the non-conductive PCB substrate 500 using techniques common in the PCB industry including selective etching, photoresist layers, shadow masking, or a combination thereof.

Figure 6B:
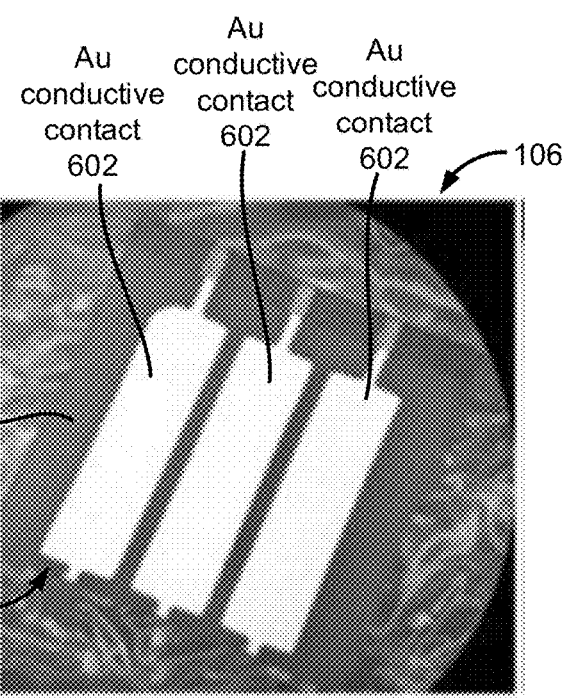
FIG. 6B is a black-and-white image showing a close-up view of a contact side of the active sensor shown in FIG. 6A.

FIG. 6B is a black-and-white image showing a close-up view of a contact side of the active sensor 106 shown in FIG. 6A. For example, as shown in FIG. 6B, each of the active electrodes can have its own conductive contact strip 602 or section deposited or plated on an opposite side of the non-conductive PCB substrate 500. For example, the conductive contact strips 602 or sections can be made of gold. The conductive contact strips 602 or sections can be segmented instances of the conducive contact layer 502 (see, e.g., FIG. 5A). The active electrodes can be electrically coupled to the conductive contacts by conductive vias (not shown in FIG. 6B) extending through the non-conductive PCB substrate 500.

Figure 6C:
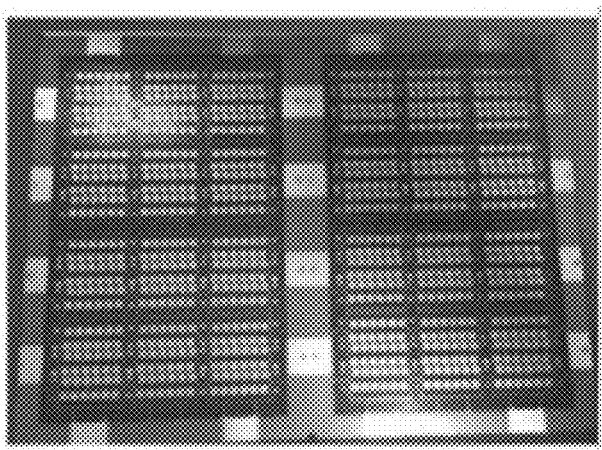
FIG. 6C is a black-and-white image showing a single PCB board that can be singulated into numerous individual active sensors.

FIG. 6C is a black-and-white image showing a single PCB board that can be singulated into individual active sensors 106 (see, e.g., FIGS. 6A and 6B). As previously discussed, a non-conductive PCB board can be covered on one side by an active electrode layer 132 using electroplating or sputter deposition. The other side of the PCB board can be covered in part by a conductive contact layer 502 (also via electroplating or a deposition technique). The active electrode layer 132 can be electrically coupled to the conductive contact layer 502 by conductive vias 504 extending through the non-conductive PCB board. As previously discussed, one PCB board processed in this manner can be singulated to produce between 400 and 500 active sensors 106.

Figure 7:
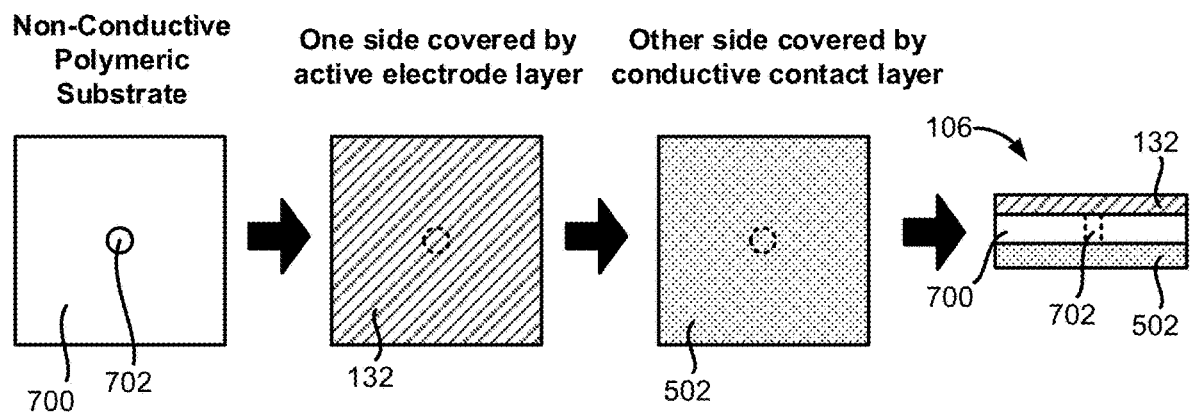
FIG. 7 illustrates yet another embodiment of an active sensor made by covering a non-conductive polymeric substrate comprising a through-hole with an active electrode layer and a conductive contact layer.

FIG. 7 illustrates yet another embodiment of an active sensor 106 made by covering a non-conductive polymeric substrate 700 comprising a through-hole 702 with an active electrode layer 132 and a conductive contact layer 502.

The non-conductive polymeric substrate 700 can be a substrate made of any type of injection-molded plastic such as polyamide, polycarbonate, polyoxymethylene, polystyrene, acrylonitrile butadiene styrene, polypropylene, polyethylene, or copolymers or blends thereof.

In some embodiments, the active electrode layer 132 is a noble metal layer. For example, the active electrode layer 132 can be a layer of platinum, a layer of gold, or a combination or composite thereof. The platinum or gold layer can be deposited or otherwise applied to the conductive polymeric substrate 700 via sputter deposition (e.g., physical vapor deposition (PVD) sputter deposition), evaporation deposition, or electrodeposition. In some embodiments, the platinum or gold layer can be printed using screen printing.

The active electrode layer 132 can have an active electrode layer thickness of at least 50 nm. In certain embodiments, the active electrode layer 132 can have an active electrode layer thickness of at least 400 nm. When the active electrode layer 132 is made of platinum or gold, the active sensor 106 can be used for measuring or monitoring the ORP of a sample.

In an alternative embodiment, a platinum layer deposited on the non-conductive polymeric substrate 700 can be modified with a surface modification technique to turn the platinum layer into a pH-sensitive layer (see, e.g., FIG. 4D). For example, an oxygen plasma treatment can be used to oxidize the platinum layer to create a platinum oxide ($PtO_2$) layer. The platinum oxide layer thus formed can respond to hydrogen ions and be used as a pH-sensitive layer. In this embodiment, the active sensor 106 can be used to measure or monitor the pH of a sample.

In some embodiments, the conductive contact layer 502 can be a gold layer. In other embodiments, the conductive contact layer 502 can be made of another type of conductive metal such as platinum, nickel, copper, or alloys or composites thereof.

The through-hole 702 can have a diameter between about 10 μm to 100 μm. In some embodiments, the active sensor 106 can have a width dimension of between about 100 μm and 6.0 mm and a length dimension of between about 100 μm and 6.0 mm. For example, the active sensor 106 can have a width dimension of about 100 μm and a length dimension of about 100 μm.

Figure 8A:
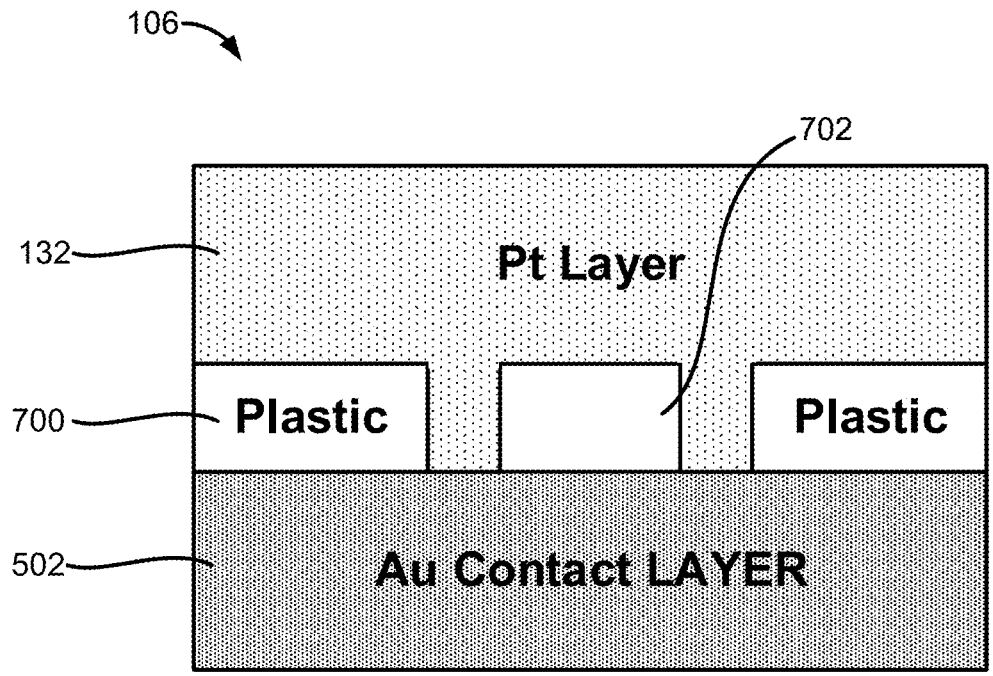
FIGS. 8A and 8B are side cross-sectional views illustrating two different embodiments of the active sensor.
Figure 8B:
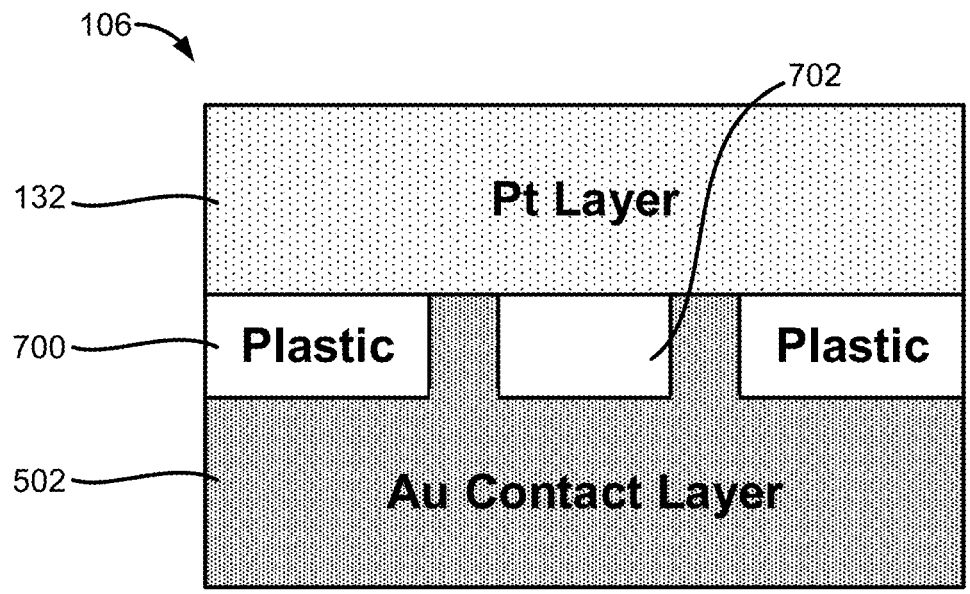

FIGS. 8A and 8B are side cross-sectional views illustrating two different embodiments of the active sensor 106. In both embodiments, the ends of the through-hole 702 are covered by the active electrode layer 132 and the conductive contact layer 502. As shown in FIGS. 8A and 8B, a conductive coating can cover the lateral sides of the through-hole 702.

In the embodiment shown in FIG. 8A, the conductive coating is comprised of the same material as the active electrode layer 132. In the embodiment shown in FIG. 8B, the conductive coating is comprised of the same material as the conductive contact layer 502. Whether the lateral sides of the through-hole 702 are covered by the active electrode material or the conductive coating material can be determined by which layer is first deposited on the non-conductive polymeric substrate 700.

As a more specific example, the conductive coating covering the lateral sides of the through-hole can be a coating of platinum when the active electrode layer 132 is a layer of platinum and the layer of platinum is first deposited on the non-conductive polymeric substrate 700. Alternatively, the conductive coating covering the lateral sides of the through-hole can be a coating of gold when the conductive contact layer 502 is a layer of gold and the layer of gold is first deposited on the non-conductive polymeric substrate 700.

In some embodiments (for example, as shown in FIGS. 8A and 8B), the entire through-hole 702 does not need to be filled as long as the lateral sides of the through-hole 702 are covered by the conductive coating. The conductive coating can serve as an electrical connection or conductive path between the two sides of the active sensor 106. Alternatively, at least part of the through-hole 702 can be filled with the conductive coating.

In some embodiments, the non-conductive polymeric substrate 700 can start off as a sheet of plastic having an array of small through-holes 702 defined throughout the sheet of plastic. The sheet of plastic can then be covered first with the active electrode layer 132 or the conductive contact layer 502. The lateral sides of the through-holes 702 and at least one of the ends of the through-holes 702 can then be coated by the material used to initially cover the sheet of plastic. The other side of the sheet of plastic including the remaining open ends of the through-holes 702 can then be covered by the conductive contact layer 502 or the active electrode layer 132, depending on which layer went first. Once the sheet of plastic is covered on both sides, the sheet of plastic can be singulated to produce the individual active sensors 106. Active sensors 106 produced using this method can be made as small as 100 μm by 100 μm (W×L).

Figure 9:
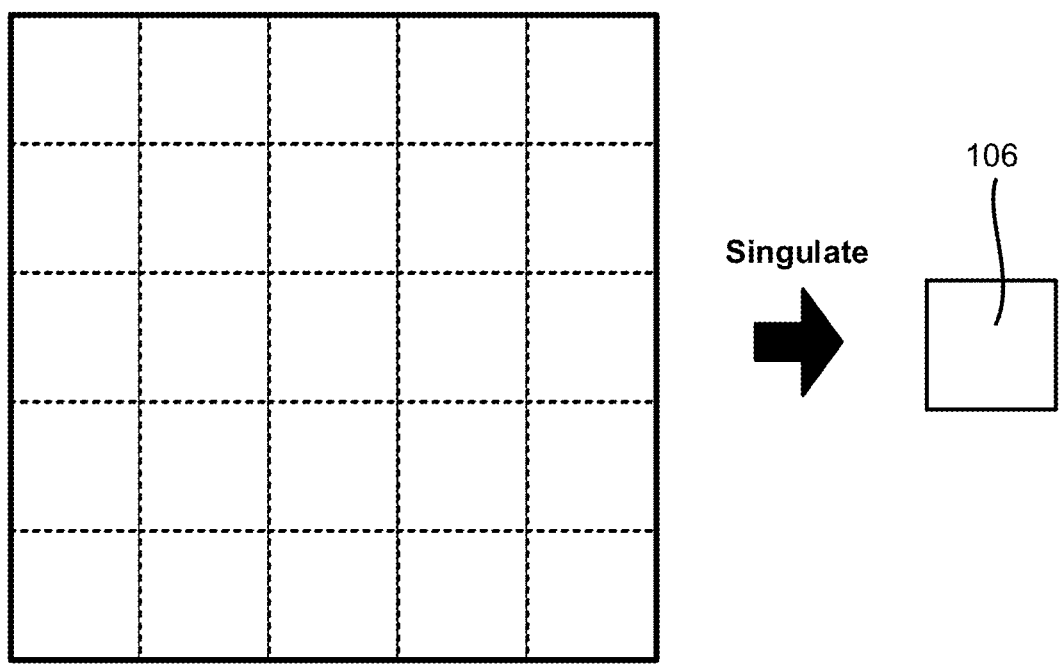
FIG. 9 illustrates that a large sheet of non-conductive plastic or a large PCB can be singulated into numerous active sensors.

FIG. 9 illustrates that a large sheet of non-conductive plastic or a large PCB can be processed using the methods disclosed herein (covered by an active electrode layer, an adhesion layer, a conductive layer, or a combination thereof) and then singulated into numerous active sensors 106. In some embodiments, the large sheet of non-conductive plastic or the large PCB can be singulated using sawing, laser cutting, metal shearing, hot wire cutting, dye cutting, stamping, or a combination thereof.

Figure 10:
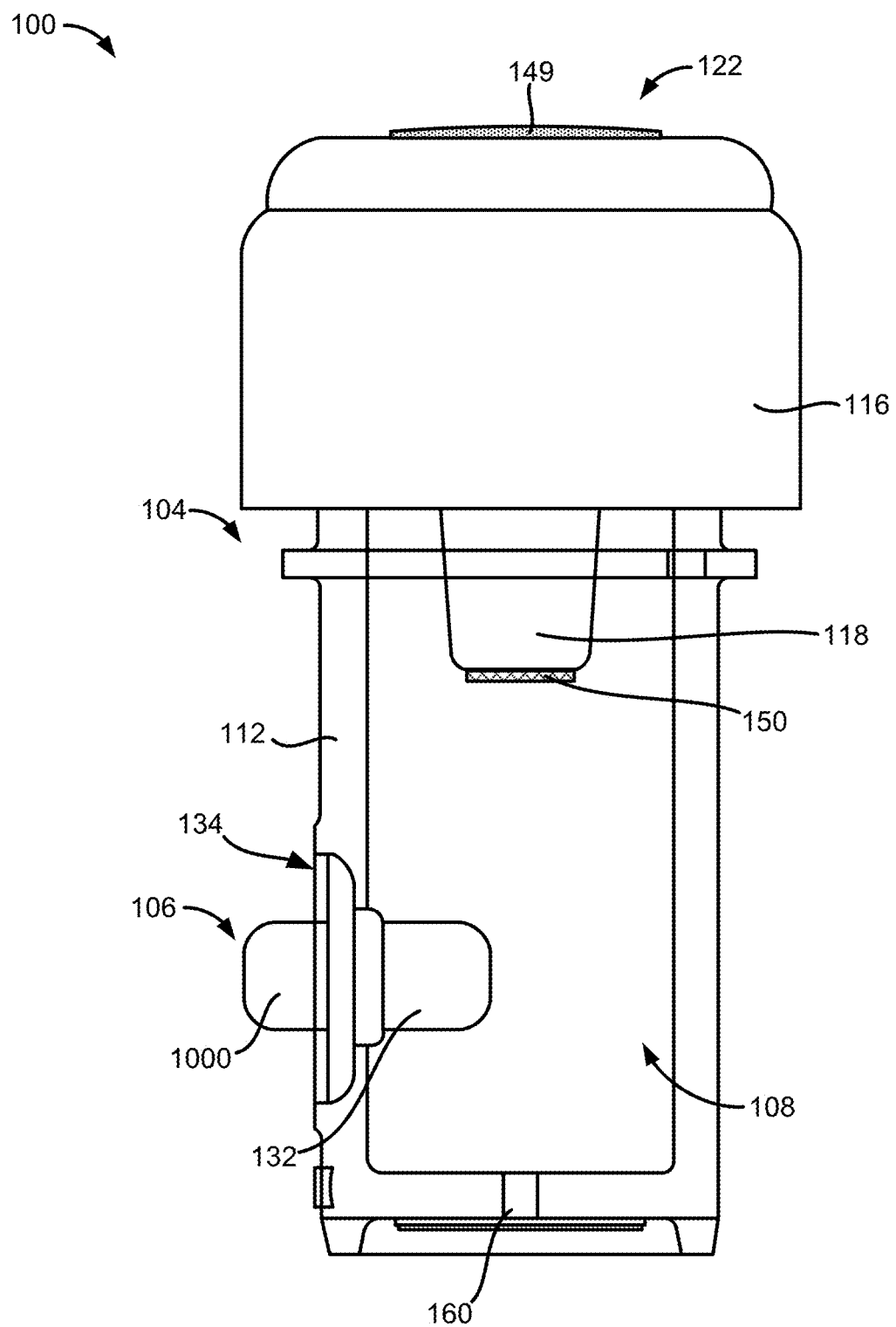
FIG. 10 illustrates a side view of another embodiment of a sensor apparatus comprising an active sensor made of a conductive dowel.

FIG. 10 illustrates a side view of another embodiment of a sensor apparatus 100 comprising an active sensor 106 made of a conductive dowel 1000. In some embodiments, the conductive dowel 1000 can be a stainless steel dowel. The conductive dowel 1000 can be covered in part by an active electrode layer 132 extending into the chamber cavity 108. The part of the conductive dowel 1000 covered by the active electrode layer 132 can extend into the chamber cavity 108 to allow the sample within the chamber cavity 108 to be in fluid contact with the active electrode layer 132.

The conductive dowel 1000 can be coupled to at least part of the chamber lateral wall 112 at a window opening defined along the chamber lateral wall 112. An opposite end of the conductive dowel 1000 (the end not covered by the active electrode layer 132) can extend out of the chamber lateral wall 112 to contact one or more conductive connections of a reader apparatus 190. The conductive dowel 1000 can be shaped substantially as a cylinder having rounded edges.

The conductive dowel 1000 can be insert molded or adhesive bonded to the chamber lateral wall 112.

In some embodiments, the active electrode layer 132 is a noble metal layer. For example, the active electrode layer 132 can be a layer of platinum, a layer of gold, or a combination or composite thereof. The platinum or gold layer can be deposited or otherwise applied to the conductive dowel 1000 via sputter deposition (e.g., physical vapor deposition (PVD) sputter deposition), evaporation deposition, or electrodeposition.

The active electrode layer 132 can have an active electrode layer thickness of at least 50 nm. In certain embodiments, the active electrode layer 132 can have an active electrode layer thickness of at least 400 nm. When the active electrode layer 132 is made of platinum or gold, the active sensor 106 can be used for measuring or monitoring the ORP of a sample.

In an alternative embodiment, a platinum layer deposited on the conductive dowel 1000 can be modified with a surface modification technique to turn the platinum layer into a pH-sensitive layer. For example, an oxygen plasma treatment can be used to oxidize the platinum layer to create a platinum oxide ($PtO_2$) layer. The platinum oxide layer thus formed can respond to hydrogen ions and be used as a pH-sensitive layer. In this embodiment, the active sensor 106 can be used to measure or monitor the pH of a sample.

Figure 11:
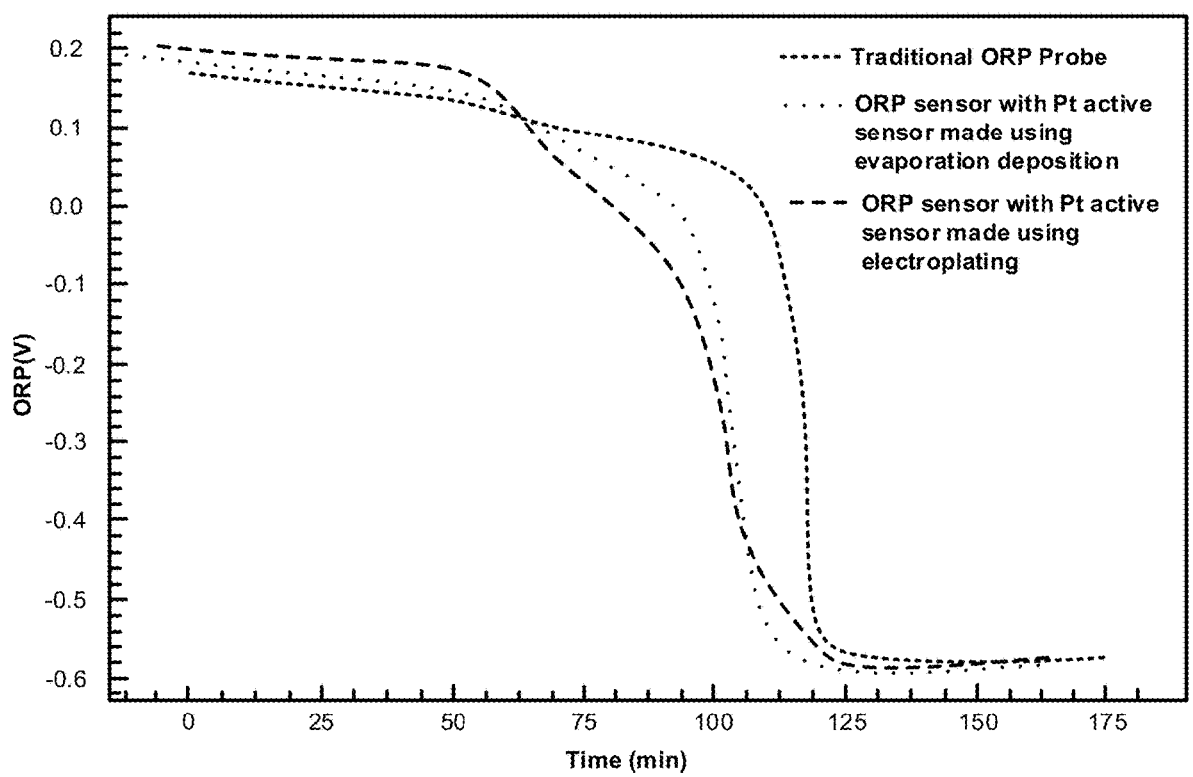
FIG. 11 is a graph illustrating a change in the oxidation reduction potential (ORP) of three samples containing *E. coli* measured over time using three different sensors.

FIG. 11 is a graph illustrating a change in the oxidation reduction potential (ORP) of three samples containing *E. coli* ATCC 25922 measured over time using three different sensors. As shown in FIG. 11, one sensor is a traditional ORP probe that is commonly used in diagnostic settings (for example, the commercially-available ORP probe distributed by Mettler-Toledo, LLC). The other two sensors are embodiments of the sensor apparatus 100 disclosed herein with one having an active sensor 106 comprising a platinum active electrode layer deposited by evaporation deposition and the other having an active sensor 106 comprising an electroplated platinum active electrode layer. The active sensors 106 in both embodiments are coupled to at least part of the chamber lateral wall 112 at a window opening 114 defined along the chamber lateral wall 112. In these embodiments, the active sensors 106 are positioned such that no part of the active sensors 106 extends into the chamber cavity 108 of the sample container 104. The change in ORP was measured by a reader apparatus 190 when each of the two sensor apparatus 100 was placed within the reader apparatus 190.

As shown by the three *E. coli* growth curves, the two sensor apparatus 100 performed similar to the commercially-available ORP probe. Any variations in the signal response were within acceptable ranges.

Figure 12:
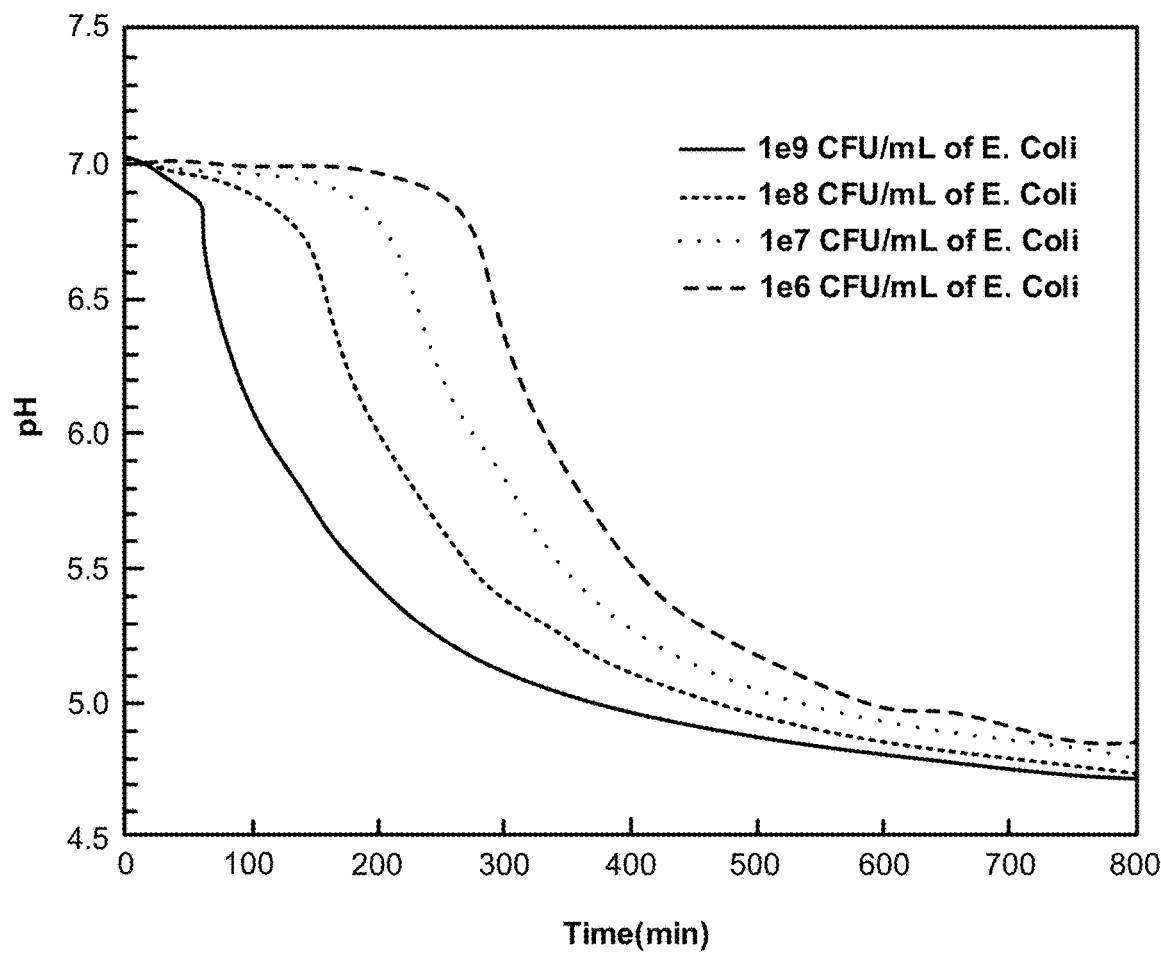
FIG. 12 is a graph illustrating a change in the pH of four samples containing different starting concentrations of *E. coli* measured over time using the sensor apparatus disclosed herein.

FIG. 12 is a graph illustrating a change in the pH of four samples containing different starting concentrations of *E. coli* ATCC 25922 measured over time using the sensor apparatus 100 disclosed herein having an active sensor 106 comprising a tantalum oxide/pentoxide ($Ta_2O_5$) active electrode layer.

As shown in FIG. 12, the *E. coli* growth curves measured followed the classical growth pattern of bacteria having a lag phase at the outset, following by an exponential phase, and ending in a stationary phase. The pattern or shape of the curves can be attributed to cellular activity undertaken by the active *E. coli* within the samples.

Figure 13A:
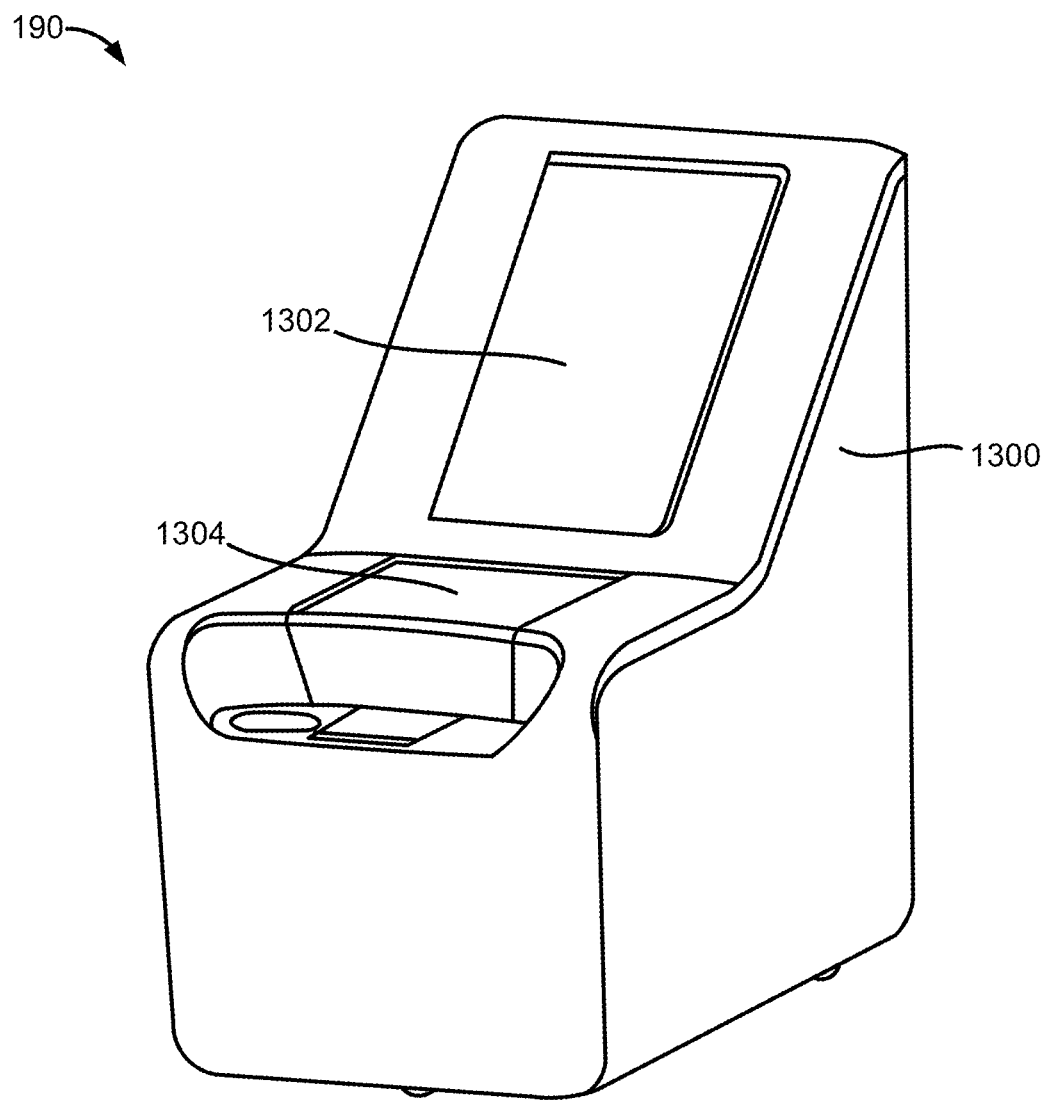
FIG. 13A illustrates a perspective view of a reader apparatus designed to receive the sensor apparatus and determine a solution characteristic of a sample within the sensor apparatus.

FIG. 13A illustrates a perspective view of a reader apparatus 190 configured to determine a solution characteristic of the sample within the sample container 104 of the sensor apparatus 100. The reader apparatus 190 can determine the solution characteristic of the sample based on a potential difference measured between the active sensor 106 (more specifically, the active electrode layer 132) and the reference sensor 122 (more specifically, the reference electrode material 149) when the active sensor 106 and the reference sensor 122 are electrically coupled via conductive connections or interfaces within the reader apparatus 190. The reader apparatus 190 can act as a voltmeter or another type of high-impedance amplifier or sourcemeter to measure relative changes in an equilibrium potential at an interface between the electrode layers in fluid contact with a sample containing electro-active redox species or charged ions.

The solution characteristic of the sample can change as the amount of electro-active redox species or the amount of $H^+$ ions changes due to the growth or metabolism (or lack thereof) of infectious agents within the sample. For example, the amount of electro-active redox species in the sample can change as a result of cellular activity undertaken by the infectious agents. As a more specific example, the amount of oxygen and the amount of electron donors can change as the amount of energy carriers, such as nicotinamide adenine dinucleotide (NADH) and flavin adenine dinucleotide ($FADH_2$), changes due to the growth or metabolism (or lack thereof) of infectious agents within the sample.

The reader apparatus 190 can measure the oxidation reduction potential (ORP) of a sample when the active electrode layer 132 of the sensor apparatus 100 is made of a redox-sensitive material such as platinum (Pt) or gold (Au). Moreover, the reader apparatus 190 can also measure the pH of a sample when the active electrode layer 132 of the sensor apparatus 100 is made of a pH-sensitive material such as a metal-oxide layer.

Figure 13B:
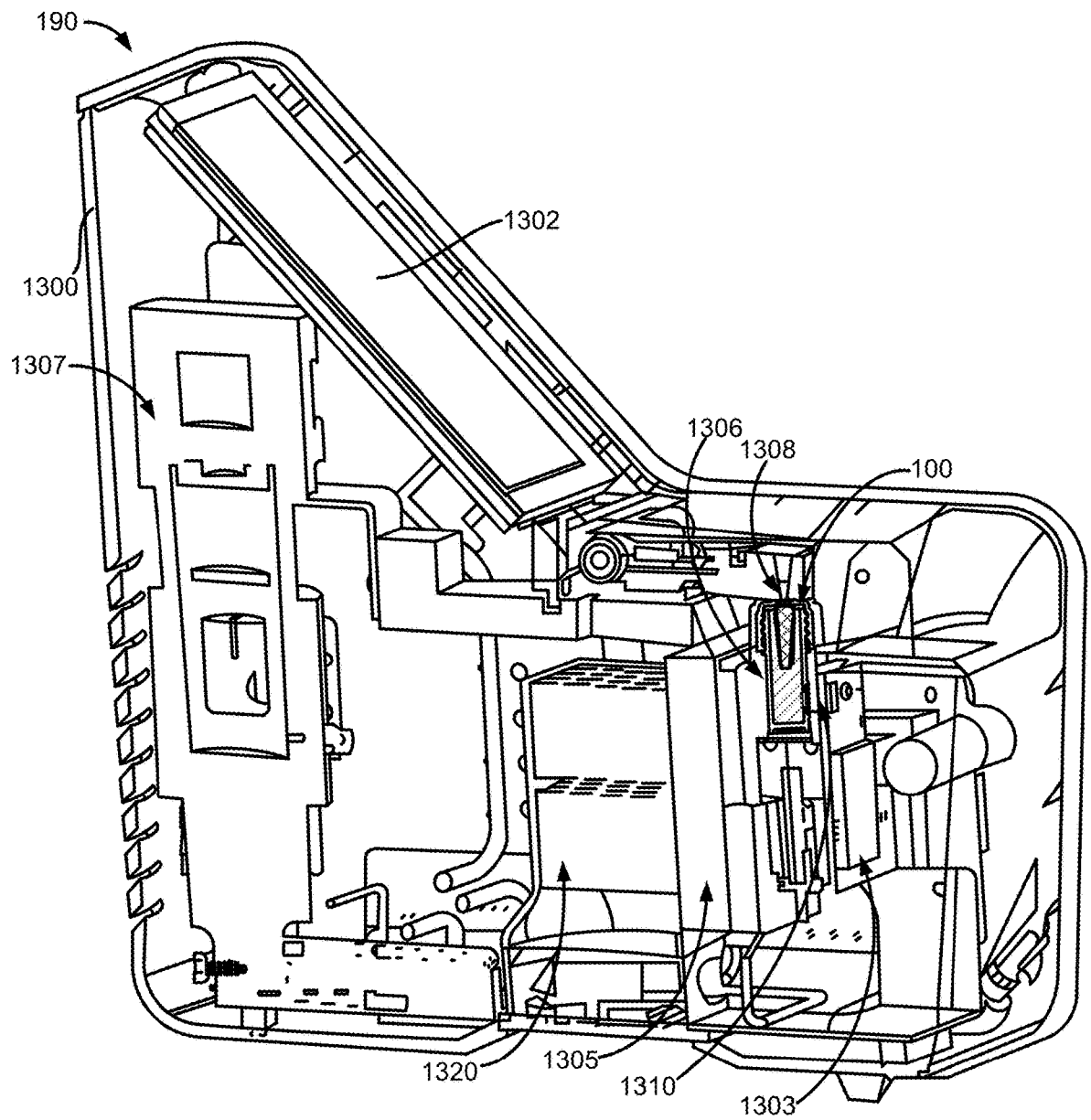
FIG. 13B illustrates a partial cutaway view of the reader apparatus with a sample-filled sensor apparatus positioned within the reader apparatus.
Figure 13C:
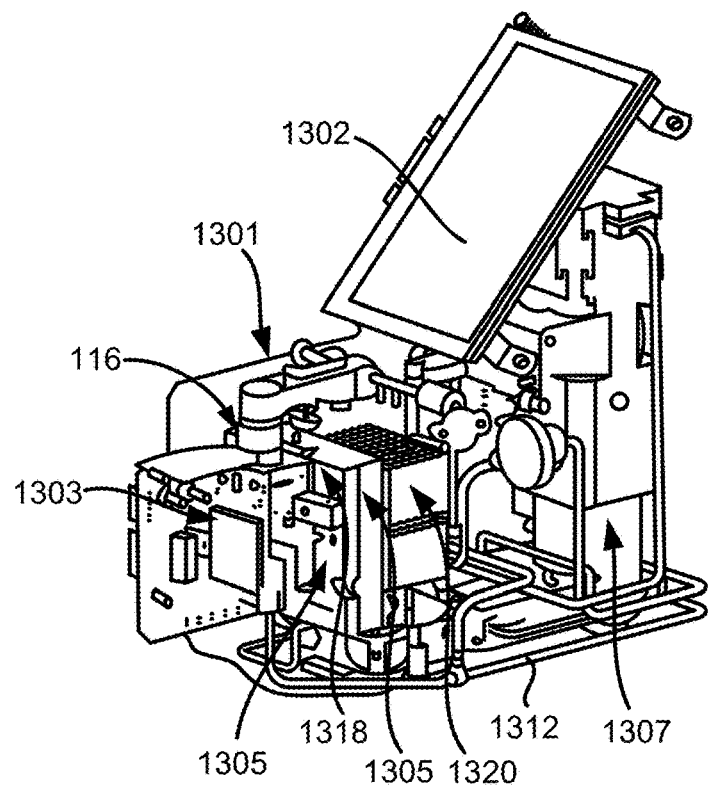
FIG. 13C illustrates a perspective view of a portion of the reader apparatus with the reader housing removed.

FIG. 13A illustrates that the reader apparatus 190 can comprise a reader housing 1300 configured to house certain functional components of the reader apparatus 190 including a main controller 1301 (see, e.g., FIG. 13C), a signal readout control unit 1303 (see, FIG. 13C), a thermal control module 1305 (see, e.g., FIGS. 13B, 13C, and 13D), and an aeration control module 1307 (see, e.g., FIGS. 13B and 13C). The reader housing 1300 can also expose a touchscreen display 1302 configured to display measurement results and allow a user to input commands to the reader apparatus 190.

A lid 1304 or cover of the reader apparatus 190 can be opened or lifted up to reveal a container receiving space 1306 (see, e.g., FIG. 13B) configured to accommodate or receive the sensor apparatus 100 for analysis or investigation by the reader apparatus 190.

FIG. 13B illustrates a partial cutaway view of the reader apparatus 190 with a sample-filled sensor apparatus 100 loaded within the reader apparatus 190. When the sensor apparatus 100 is positioned within the container receiving space 1306, a reference electrode contact 1308 of the reader apparatus 190 can be placed or moved into contact with the reference electrode material 149 positioned on the container cap 116 (see, e.g., FIG. 1D) of the sensor apparatus 100. Moreover, when the sensor apparatus 100 is positioned within the container receiving space 1306, an active electrode contact 1310 of the reader apparatus 190 can be placed or moved into contact with a conductive substrate layer or conductive contact (e.g., any of the conductive substrate 406 of FIGS. 4B-4D or the conductive contact layer 502 of FIG. 5A) of the active sensor 106.

In some embodiments, the reference electrode contact 1308 and the active electrode contact 1310 can comprise one or more conductive pogo or spring-loaded pins, conductive leaf contacts, or a combination thereof. More specifically, the conductive pogo pins or leaf contacts can be made of copper, nickel, stainless steel, or alloys thereof.

The reference electrode contact 1308 and the active electrode contact 1310 can be electrically coupled to a signal readout control unit 1303. The signal readout control unit 1303 can comprise one or more processors, chipsets, or chip modules programmed to convert and read signals obtained from the active sensor 106 and the reference sensor 122 of the sensor apparatus 100.

FIG. 13B also illustrates that the reader apparatus 190 can comprise a thermal control module 1305 and an aeration control module 1307. The thermal control module 1305 can be configured to incubate the sample-filled sensor apparatus 100. The thermal control module 1305 can incubate the sensor apparatus 100 by heating at least part of the sensor apparatus 100 via a heating block 1318 (see, e.g., FIG. 13D). In some embodiments, the heating block 1318 can heat a lateral side of the sample container 104 opposite the active sensor 106. In certain embodiments, the heating block 1318 can partially surround or cradle the sample container 104 to heat the sensor apparatus 100.

In some embodiments, the heating block 1318 can be made in part of aluminum. In other embodiments, the heating block 1318 can be made in part of another type of heat conducting metallic material. The heating block 1318 can be a dry heating block.

The sensor apparatus 100 can be heated to an incubation temperature of between about 30° C. and 40° C. (e.g., about 35° C.±2° C.). The sensor apparatus 100 can be incubated for an incubation period. The incubation period can range from 15 minutes to over 48 hours. The incubation period can be adjusted based on the type of infectious agent suspected in the sample.

In some embodiments, the thermal control module 1305 can be controlled by the main controller 1301 (see, e.g., FIG. 13C) of the reader apparatus 190. In other embodiments, the thermal control module 1305 can be controlled by another controller or module within the reader apparatus 190 or by the signal readout control unit 1303.

The reader apparatus 190 can also comprise a cooling component 1320. The cooling component 1320 can cool an output sample or a standardized inoculum 1726 (see, e.g., FIG. 17) prepared within the sensor apparatus 100 to a cooling temperature. The cooling temperature can be between about 15° C. and 20° C. (e.g., about 15° C.±2° C.).

In some embodiments, the cooling component 1320 and the heating block 1318 can refer to different parts of the same internal temperature control mechanism within the reader apparatus 190. For example, the cooling component 1320 can be controlled by a temperature control module similar to the thermal control module 1305.

In further embodiments, one metallic (e.g., aluminum) block or holder in contact with or in proximity to the sensor apparatus 100 can be used as both the cooling component 1320 (e.g., a cooling block) and the heating block 1318.

In some embodiments, a nutrient solution or stimulus solution can be introduced into the sample container 104 before the sensor apparatus 100 is incubated. For example, the nutrient solution can be a solution containing bacto-tryptone, yeast extract, beef extract, cation-adjusted Mueller Hinton Broth (CAMHB), starch, an acid hydrolysate of casein, calcium chloride, magnesium chloride, sodium chloride, blood or lysed blood including lysed horse blood (LHB), a CAMHB-LHB mixture, glucose, or a combination thereof. The nutrient solution can be used to counteract the buffering effects of ions or substances present in the sample when the sample is composed of a bodily fluid.

The aeration control module 1307 can be configured to aerate the sample within the sample container 104 by pumping a gas 162 (see, e.g., FIG. 1D) into the chamber cavity 108 containing the sample. The gas 162 can be pumped into the sample container 104 through an aeration port 160 defined along the bottom of the sample container 104 (see, e.g., FIG. 1D).

Aerating the sample can enhance a growth rate of infectious agents within the sample by increasing the supply of oxygen to such infectious agents. Moreover, aerating the sample can also enable detachment of the infectious agents from the interior walls of the sample container 104 so as to inhibit biofilm formation.

FIG. 13C illustrates a perspective view of a portion of the reader apparatus 190 with the reader housing 1300 removed. As shown in FIG. 13C, the aeration control module 1307 can delivery gas 162 via a gas delivery conduit 1312 connecting the aeration control module 1307 to the sensor apparatus 100. In some embodiments, at least a segment of the gas delivery conduit 1312 can be positioned along or wound around a base or bottom portion of the reader apparatus 190.

Figure 13D:
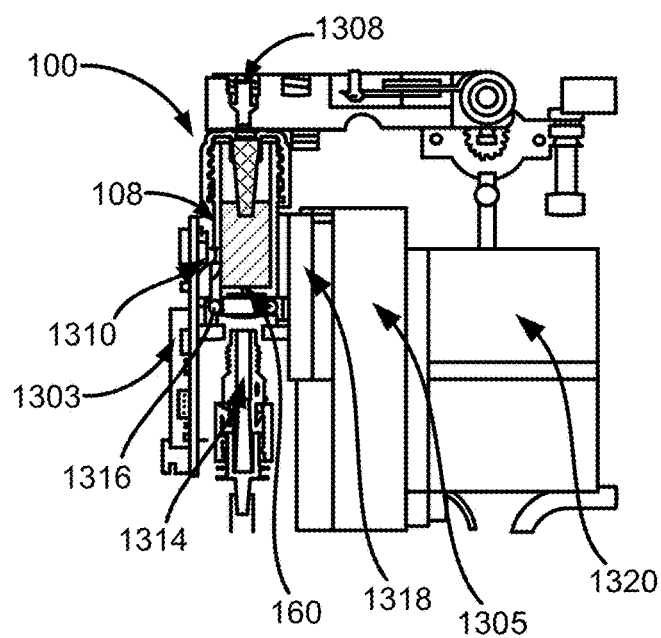
FIG. 13D illustrates a close-up view of a gas nozzle of the reader apparatus being connected to the bottom of the sensor apparatus to aerate the sample within the sensor apparatus.

FIG. 13D illustrates a close-up view of a gas nozzle 1314 being connected to the bottom of the sensor apparatus 100 to aerate the sample within the sample container 104. The gas nozzle 1314 can be disposed at a terminal or distal end of the gas delivery conduit 1312.

As shown in FIG. 13D, the gas nozzle 1314 can connect to the aeration port 160 at the bottom of the sample container 104 via a nozzle interface 1316. In some embodiments, the nozzle interface 1316 can be an O-ring. In other embodiments, the nozzle interface 1316 can be another type of gasket or fluid-sealing interface.

In some embodiments, the gas 162 can be ambient air (e.g., the air in a laboratory, clinical setting, or testing facility). In other embodiments, the gas 162 can comprise a combination of pressurized oxygen, carbon dioxide, nitrogen, and argon. Aerating the sample can accelerate the growth of a microbial population within the sample by providing an oxygen rich environment within the sample container 104.

The aeration control module 1307 can pump gas 162 into the sample container 104 at a constant flow rate of between about 1.0 mL/min and 10.0 mL/min.

In some embodiments, the aeration control module 1307 can be controlled by the main controller 1301 (see, e.g., FIG. 13C). In other embodiments, the aeration control module 1307 can be controlled by another controller or module within the reader apparatus 190 or by the signal readout control unit 1303. For example, the amount of gas 162 (e.g., ambient air) pumped or otherwise directed into the sample container 104 can be dictated by a change in a solution characteristic of the sample detected by the reader apparatus 190 or a lack of any such change.

Figure 14:
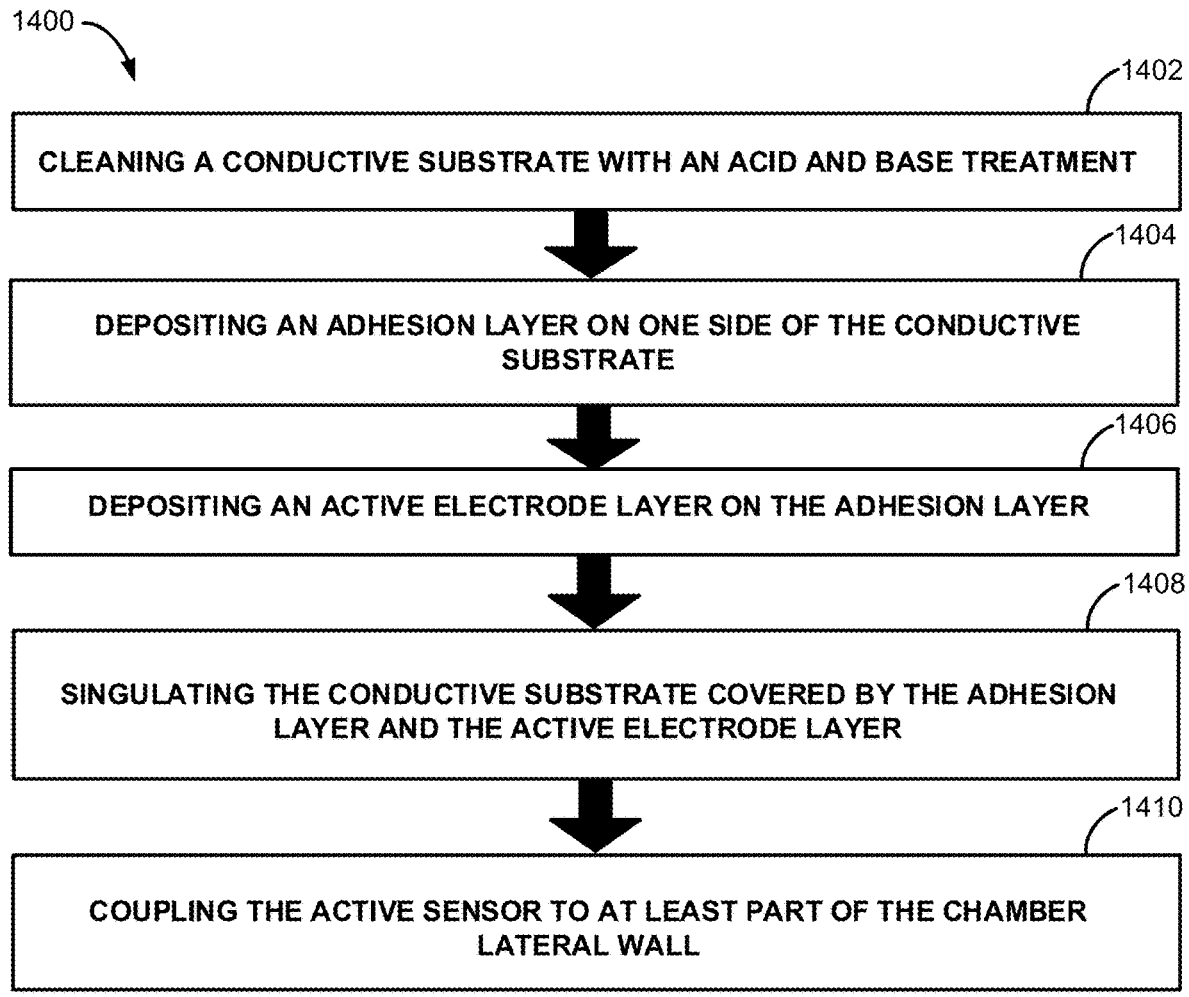
FIG. 14 illustrates one embodiment of a method of making a sensor apparatus for measuring a solution characteristic of a sample.

FIG. 14 illustrates a method 1400 of making a sensor apparatus 100 for measuring a solution characteristic of a sample. The method 1400 can comprise cleaning a conductive substrate 406 (e.g., a sheet of stainless steel such as 316 SS) with an acid and base treatment in step 1402.

The conductive substrate 406 can first be cleaned with a series of acid and base treatments to remove any impurities or surface contaminants (e.g., free iron). Such treatments can be performed with nitric acid (10%) followed by ammonium hydroxide (175 mM), isopropyl alcohol (99%), or acetone. In other embodiments, the conductive substrate 406 can be cleaned and descaled using other acids, bases, alcohols, solvents, or other chemicals.

The method 1400 can also comprise depositing an adhesion material on one side of the cleaned conductive substrate 406 until an adhesion layer 408 forms on the cleaned conductive substrate 406 in step 1404. In some embodiments, the adhesion layer 408 can be deposited by a sputter deposition technique such as physical vapor deposition (PVD). In some embodiments, the adhesion layer 408 can be a layer of chromium (Cr). Chromium can be selected because it creates a bond to the chromium in the stainless steel of the conductive substrate 406. In other embodiments, the adhesion layer 408 can also be a layer of gold (Au) or nickel (Ni).

Step 1404 can also comprise depositing an adhesion material (e.g., Cr, Au, or Ni) until the adhesion layer 408 is at least 20 nm thick.

The method 1400 can further comprise depositing an active electrode material on the adhesion layer 408 until an active electrode layer 132 forms on the adhesion layer 408 in step 1406. The active electrode layer 132 can be a noble metal layer such as a platinum or gold layer when the sensor apparatus 100 is to be used as an ORP sensor. Depositing the active electrode layer 132 can comprise depositing an active electrode material (e.g., Pt) using sputter deposition (e.g., PVD), evaporation deposition, or electrodeposition. For certain processes, such as the evaporation deposition, the conductive substrate 406 can be precleaned in vacuum with argon (Ar) plasma etching. In other embodiments, the active electrode material can be applied using ink screen-printing.

Step 1406 can also comprise depositing an active electrode material until the active electrode layer 132 is at least 50 nm thick. Step 1406 can further comprise depositing the active electrode material until the active electrode layer 132 is at least 400 nm thick. The applicants discovered that this minimum thickness is needed to prevent nano-sized holes from forming in the active electrode layer 132 that would allow fluid (e.g., the fluid sample) to make its way through the active electrode layer 132 and into contact with other layers of the active sensor 106 (thereby adversely affecting the measurement). Moreover, when an antimicrobial material (e.g., copper or nickel) is used as the conductive substrate 406, the active electrode layer 132 having a minimum thickness of 400 nm can act as a barrier to protect the microbes in the fluid sample.

In certain embodiments, the adhesion layer 408 can be deposited in a vacuum chamber and the active electrode layer 132 can be deposited subsequent to the adhesion layer 408 in the same vacuum chamber.

Alternatively, step 1406 can comprise depositing a metal layer and surface modifying the metal layer to create a metal oxide layer. For example, step 1406 can comprise depositing a platinum layer and oxidizing the platinum layer to create a platinum oxide ($PtO_2$) layer serving as the active electrode layer 132. The active electrode layer 132 can be a metal oxide layer (e.g., platinum oxide or tantalum oxide) when the sensor apparatus 100 is to be used as a pH sensor.

The method 1400 can also comprise singulating the conductive substrate 406 covered by the adhesion layer 408 and the active electrode layer 132 in step 1408. The conductive substrate 406 covered by the adhesion layer 408 and the active electrode layer 132 can be singulated by laser cutting, metal shearing, hot wire cutting, dye cutting, stamping, or sawing. The conductive substrate 406 covered by the adhesion layer 408 and the active electrode layer 132 can be singulated to yield an active sensor 106 sized to cover a window opening 114 defined along the chamber lateral wall 112 of the sample container 104 (see, e.g., FIGS. 1B-1D and 2).

The method 1400 can further comprise coupling the active sensor 106 to at least part of the chamber lateral wall 112 in step 1410. The active sensor 106 can be coupled to at least part of the chamber lateral wall 112 such that no part of the active sensor 106 extends into a chamber cavity 108 within the sample container 104 and the active electrode layer 132 faces the chamber cavity 108 to allow any sample within the chamber cavity 108 to be in fluid contact with the active electrode layer 132 through at least part of the chamber lateral wall 112 surrounding the window opening 114. The active sensor 106 can be coupled to at least part of the chamber lateral wall 112 such that the active sensor 106 (including the active electrode layer 132) is positioned radially outward from an interior-facing or cavity-facing side of the chamber lateral wall 112 and the lateral sides 136 of the active sensor 106 are not in fluid communication with the chamber cavity 108.

In some embodiments, coupling the active sensor to at least part of the chamber lateral wall 112 of the sample container 104 can further comprise applying a bead of adhesive 138 to a part of the chamber lateral wall 112 within a recessed portion 134 defined along the chamber lateral wall 112 surrounding the window opening 114, pressing or placing the active sensor 106 onto the bead of adhesive 138 within the recessed portion 134, and curing the adhesive 138.

In alternative embodiments, coupling the active sensor to at least part of the chamber lateral wall 112 of the sample container 104 can comprise insert-molding the active sensor 106 into the chamber lateral wall 112 while the sample container 104 is formed by injection molding.

In further alternative embodiments, coupling the active sensor to at least part of the chamber lateral wall 112 of the sample container 104 can comprise focally melting (e.g., by ultrasonic welding) a part of the chamber lateral wall 112 surrounding the window opening 114, pressing or placing the active sensor 106 onto the melted part of the chamber lateral wall 112, and allowing the melted part of the chamber lateral wall 112 to cool to affix the active sensor 106 to the chamber lateral wall 112.

Figure 15:
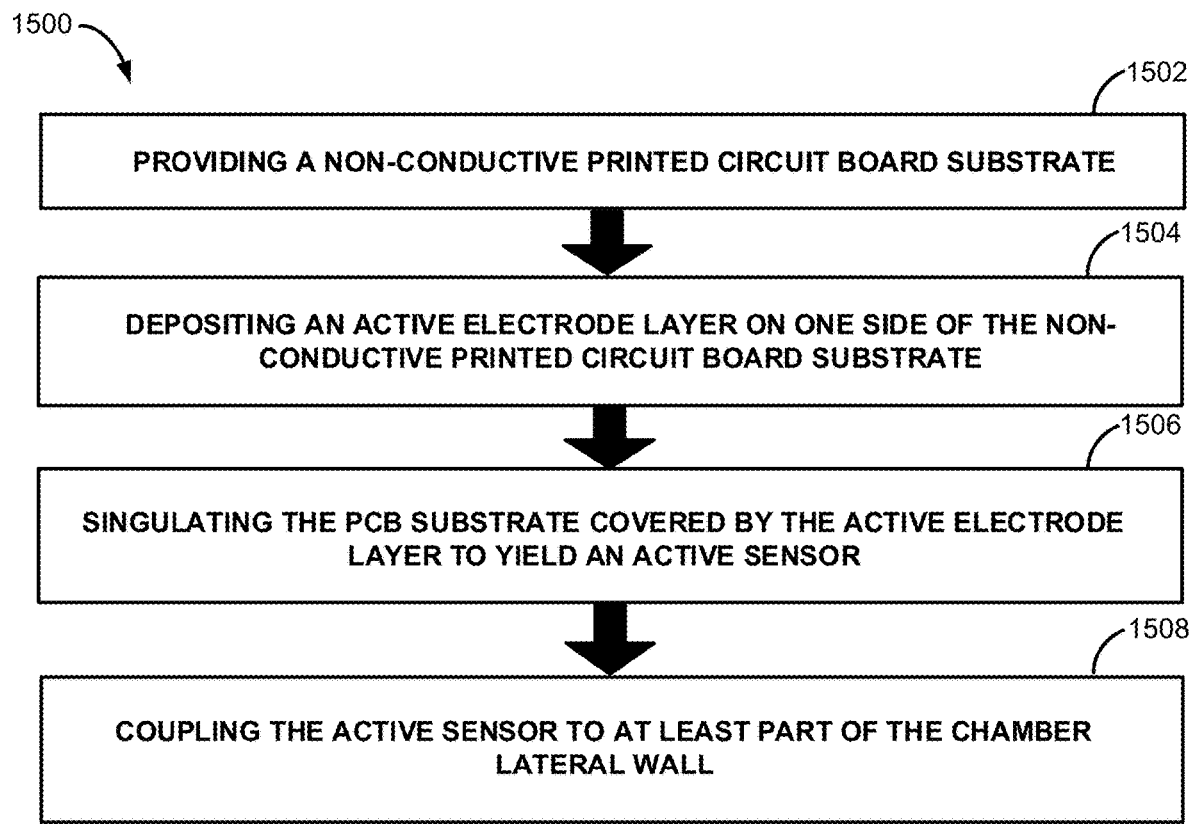
FIG. 15 illustrates another embodiment of a method of making a sensor apparatus for measuring a solution characteristic of a sample.

FIG. 15 illustrates yet another method 1500 of making a sensor apparatus 100 for measuring a solution characteristic of a sample. The method 1500 can comprise providing a non-conductive printed circuit board (PCB) substrate 500 (see, e.g., FIG. 5A) in step 1502.

The method 1500 can also comprise depositing an active electrode material on one side of the non-conductive PCB substrate 500 until an active electrode layer 132 forms on the non-conductive PCB substrate 500 in step 1504. Step 1504 can also comprise depositing an active electrode material until the active electrode layer 132 is at least 50 nm thick. Step 1504 can further comprise depositing an active electrode material until the active electrode layer 132 is at least 400 nm thick. After the deposition step, the active electrode layer 132 can be electrically coupled to conductive contacts or a conductive contact layer 502 of the non-conductive PCB substrate 500 by conductive vias 504 extending through the non-conductive PCB substrate 500.

The active electrode layer 132 can be a noble metal layer such as a platinum or gold layer when the sensor apparatus 100 is to be used as an ORP sensor. Depositing the active electrode layer 132 can comprise depositing an active electrode material (e.g., Pt) using sputter deposition (e.g., PVD), evaporation deposition, or electrodeposition.

The method 1500 can also comprise singulating the non-conductive PCB substrate 500 covered by the active electrode layer 132 to yield an active sensor 106 sized to cover a window opening 114 defined along a chamber lateral wall 112 of a sample container 104 in step 1506. The non-conductive PCB substrate 500 covered by the active electrode layer 132 can be singulated by laser cutting, metal shearing, hot wire cutting, dye cutting, stamping, or sawing.

The active sensor 106 can comprise at least one conductive via 504 extending through the PCB substrate 500.

The method 1500 can further comprise coupling the active sensor 106 to at least part of the chamber lateral wall 112 in step 1508. The active sensor 106 can be coupled to at least part of the chamber lateral wall 112 such that no part of the active sensor 106 extends into a chamber cavity 108 within the sample container 104 and the active electrode layer 132 faces the chamber cavity 108 to allow any sample within the chamber cavity 108 to be in fluid contact with the active electrode layer 132 through at least part of the chamber lateral wall 112 surrounding the window opening 114. The active sensor 106 can be coupled to at least part of the chamber lateral wall 112 such that the active sensor 106 (including the active electrode layer 132) is positioned radially outward from an interior-facing or cavity-facing side of the chamber lateral wall 112 and the lateral sides 136 of the active sensor 106 are not in fluid communication with the chamber cavity 108.

In some embodiments, coupling the active sensor to at least part of the chamber lateral wall 112 of the sample container 104 can further comprise applying a bead of adhesive 138 to a part of the chamber lateral wall 112 within a recessed portion 134 defined along the chamber lateral wall 112 surrounding the window opening 114, pressing or placing the active sensor 106 onto the bead of adhesive 138 within the recessed portion 134, and curing the adhesive 138.

In alternative embodiments, coupling the active sensor to at least part of the chamber lateral wall 112 of the sample container 104 can comprise insert-molding the active sensor 106 into the chamber lateral wall 112 while the sample container 104 is formed by injection molding.

In further alternative embodiments, coupling the active sensor to at least part of the chamber lateral wall 112 of the sample container 104 can comprise focally melting (e.g., by ultrasonic welding) a part of the chamber lateral wall 112 surrounding the window opening 114, pressing or placing the active sensor 106 onto the melted part of the chamber lateral wall 112, and allowing the melted part of the chamber lateral wall 112 to cool to affix the active sensor 106 to the chamber lateral wall 112.

Figure 16:
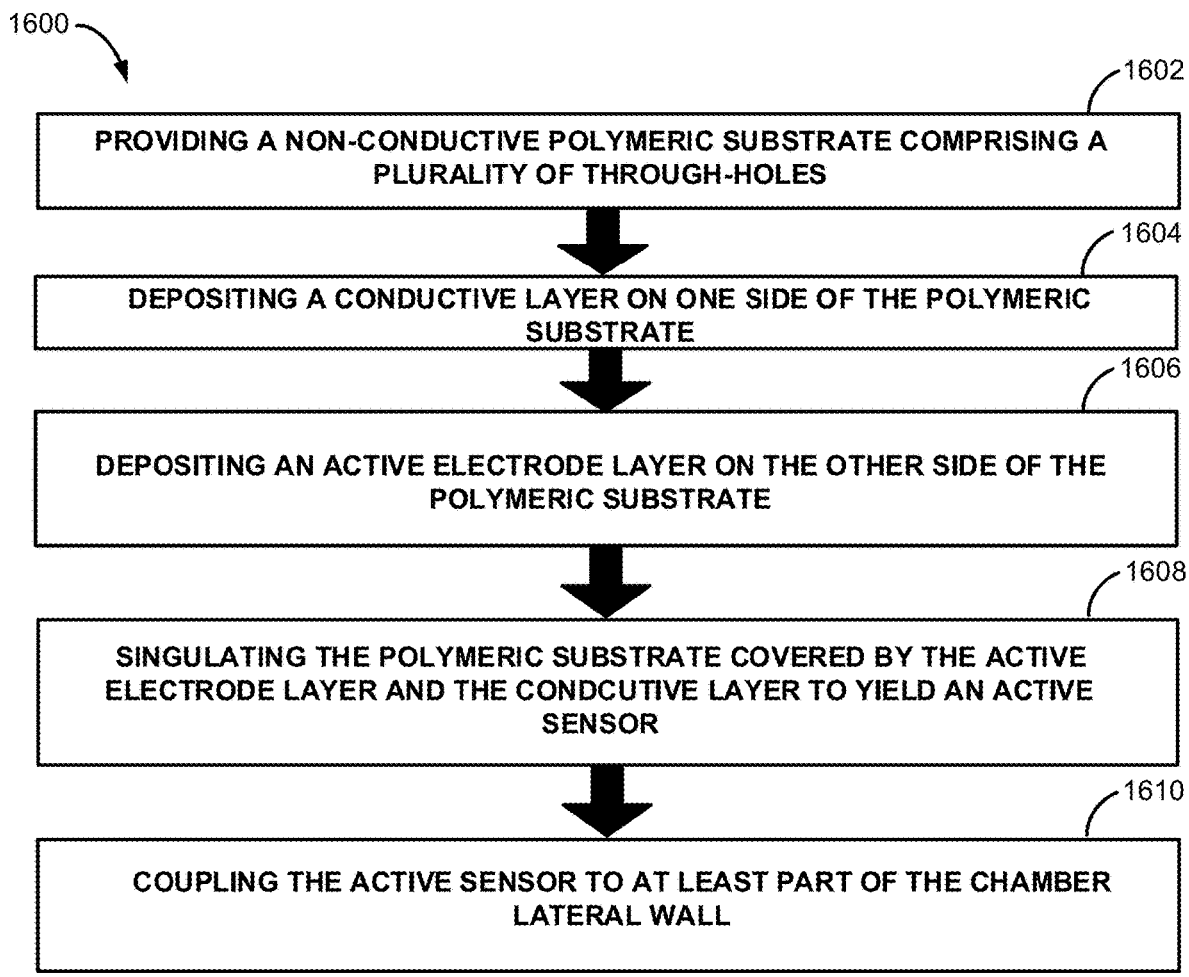
FIG. 16 illustrates yet another embodiment of a method of making a sensor apparatus for measuring a solution characteristic of a sample.

FIG. 16 illustrates yet another method 1600 of making a sensor apparatus 100 for measuring a solution characteristic of a sample. The method 1600 can comprise providing a non-conductive polymeric substrate 700 comprising a plurality of through-holes 702 in step 1602. The method 1600 can also comprise depositing a conductive contact layer 502 on one side of the polymeric substrate 700 in step 1604. Depositing the conductive contact layer 502 can comprise depositing an electrically conductive material (e.g., Au) on the polymeric substrate 700 using sputter deposition (e.g., PVD), evaporation deposition, or electrodeposition.

The method 1600 can further comprise depositing an active electrode layer 132 on another side of the polymeric substrate 700 in step 1606. Depositing the active electrode layer 132 can comprise depositing an active electrode material (e.g., Pt) on the polymeric substrate 700 using sputter deposition (e.g., PVD), evaporation deposition, or electrodeposition.

One end of each of the through-holes 702 can be covered by the active electrode layer 132 and the other end of each of the through-holes 702 can be covered by the conductive contact layer 502. The active electrode layer 132, after the deposition steps, can be electrically coupled to the conductive contact layer 502 via a conductive coating covering lateral sides of the through-holes 702.

The method 1600 can also comprise singulating the non-conductive polymeric substrate 700 covered by the active electrode layer 132 and the conductive contact layer 502 to yield an active sensor 106 sized to cover a window opening 114 defined along a chamber lateral wall 112 of a sample container 104 in step 1608. The non-conductive polymeric substrate 700 covered by the active electrode layer 132 and the conductive contact layer 502 can be singulated by laser cutting, metal shearing, hot wire cutting, dye cutting, stamping, or sawing. The active sensor 106 can comprise at least one through-hole 702 extending through the non-conductive polymeric substrate 700.

The method 1600 can further comprise coupling the active sensor 106 to at least part of the chamber lateral wall 112 in step 1610. The active sensor 106 can be coupled to at least part of the chamber lateral wall 112 such that no part of the active sensor 106 extends into a chamber cavity 108 within the sample container 104 and the active electrode layer 132 faces the chamber cavity 108 to allow any sample within the chamber cavity 108 to be in fluid contact with the active electrode layer 132 through at least part of the chamber lateral wall 112 surrounding the window opening 114. The active sensor 106 can be coupled to at least part of the chamber lateral wall 112 such that the active sensor 106 (including the active electrode layer 132) is positioned radially outward from an interior-facing or cavity-facing side of the chamber lateral wall 112 and the lateral sides 136 of the active sensor 106 are not in fluid communication with the chamber cavity 108.

In some embodiments, coupling the active sensor to at least part of the chamber lateral wall 112 of the sample container 104 can further comprise applying a bead of adhesive 138 to a part of the chamber lateral wall 112 within a recessed portion 134 defined along the chamber lateral wall 112 surrounding the window opening 114, pressing or placing the active sensor 106 onto the bead of adhesive 138 within the recessed portion 134, and curing the adhesive 138.

In alternative embodiments, coupling the active sensor to at least part of the chamber lateral wall 112 of the sample container 104 can comprise insert-molding the active sensor 106 into the chamber lateral wall 112 while the sample container 104 is formed by injection molding.

In further alternative embodiments, coupling the active sensor to at least part of the chamber lateral wall 112 of the sample container 104 can comprise focally melting (e.g., by ultrasonic welding) a part of the chamber lateral wall 112 surrounding the window opening 114, pressing or placing the active sensor 106 onto the melted part of the chamber lateral wall 112, and allowing the melted part of the chamber lateral wall 112 to cool to affix the active sensor 106 to the chamber lateral wall 112.

Figure 17:
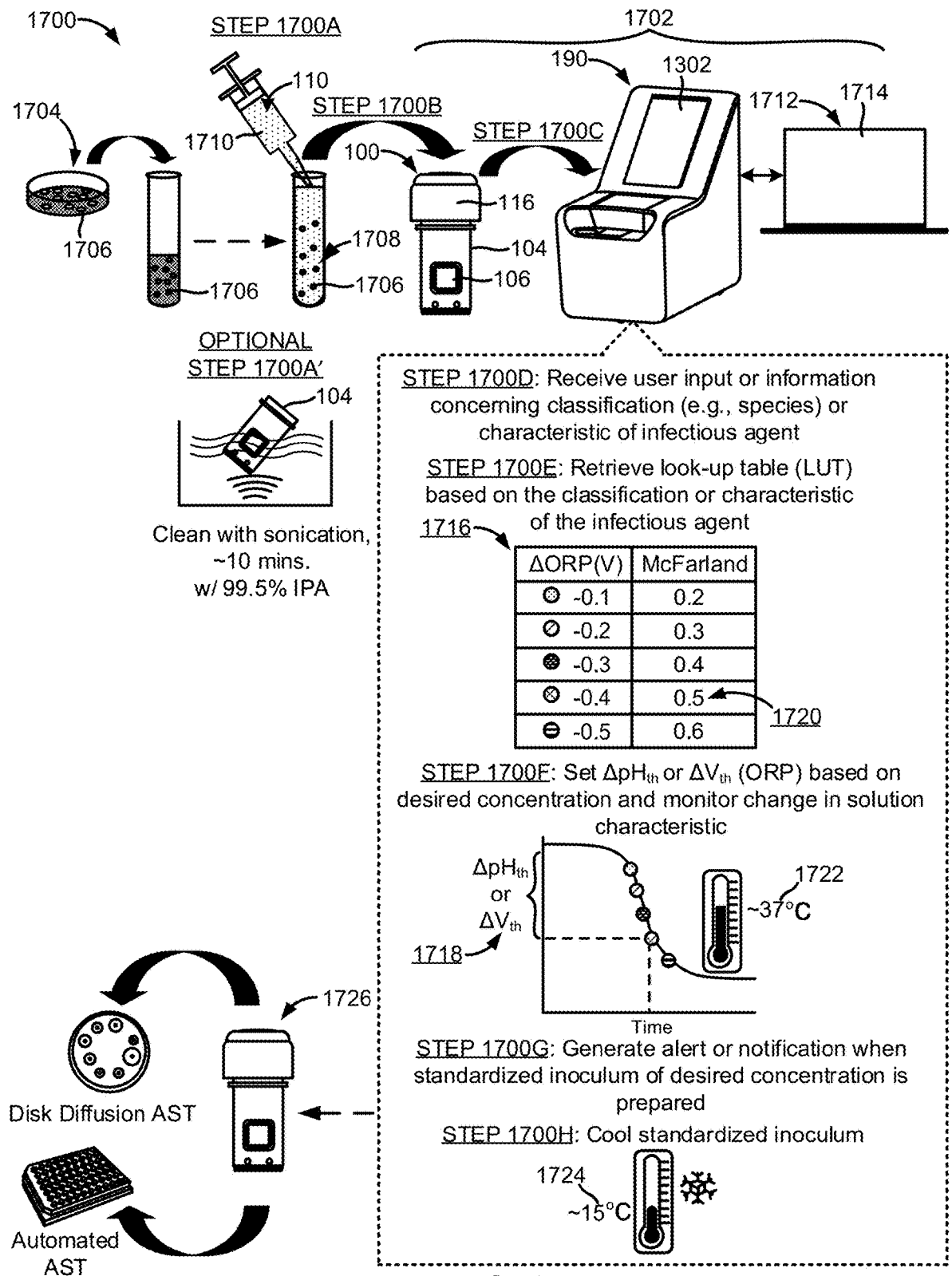
FIG. 17 illustrates one embodiment of a method and system for preparing a standardized inoculum for downstream AST testing.

FIG. 17 illustrates a method 1700 and system 1702 of preparing a standardized inoculum 1726 from a source sample 1704 comprising an infectious agent 1706 for downstream testing. In some embodiments, the method 1700 and system 1702 can be used to prepare a standardized inoculum 1726 for antimicrobial susceptibility testing (AST).

In some embodiments, the infectious agent 1706 can be bacteria from the order Enterobacterales. In certain embodiments, the infectious agent 1706 can be bacteria selected from the genus *Acinetobacter, Acetobacter, Actinomyces, Aerococcus, Aeromonas, Agrobacterium, Anaplasma, Azorhizobium, Azotobacter, Bacillus, Bacteroides, Bartonella, Bordetella, Borrelia, Brucella, Burkholderia, Calymmatobacterium, Campylobacter, Chlamydia, Chlamydophila, Citrobacter, Clostridium, Corynebacterium, Coxiella, Ehrlichia, Enterobacter, Enterococcus, Escherichia, Francisella, Fusobacterium, Gardnerella, Haemophilus, Helicobacter, Klebsiella, Lactobacillus, Legionella, Listeria, Methanobacterium, Microbacterium, Micrococcus, Morganella, Moraxella, Mycobacterium, Mycoplasma, Neisseria, Pandoraea, Pasteurella, Peptostreptococcus, Porphyromonas, Prevotella, Proteus, Providencia, Pseudomonas, Ralstonia, Raoultella, Rhizobium, Rickettsia, Rochalimaea, Rothia, Salmonella, Serratia, Shewanella, Shigella, Spirillum, Staphylococcus, Strenotrophomonas, Streptococcus, Streptomyces, Treponema, Vibrio, Wolbachia,* or *Yersinia*.

More specifically, the infectious agent 1706 can be bacteria selected from the group consisting of *Staphylococcus aureus, Staphylococcus lugdunensis,* coagulase-negative *Staphylococcus* species (including but not limited to *Staphylococcus epidermidis, Staphylococcus haemolyticus, Staphylococcus hominis, Staphylococcus capitis,* not differentiated), *Enterococcus faecalis, Enterococcus faecium* (including but not limited to *Enterococcus faecium* and other *Enterococcus* spp., not differentiated, excluding *Enterococcus faecalis*), *Streptococcus pneumoniae, Streptococcus pyogenes, Streptococcus agalactiae, Streptococcus* spp., (including but not limited to *Streptococcus mitis, Streptococcus pyogenes, Streptococcus gallolyticus, Streptococcus agalactiae, Streptococcus pneumoniae,* not differentiated), *Pseudomonas aeruginosa, Acinetobacter baumannii, Klebsiella* spp. (including but not limited to *Klebsiella pneumoniae, Klebsiella oxytoca,* not differentiated), *Escherichia coli, Enterobacter* spp. (including but not limited to *Enterobacter cloacae, Enterobacter aerogenes,* not differentiated), *Proteus* spp. (including but not limited to *Proteus mirabilis, Proteus vulgaris,* not differentiated), *Citrobacter* spp. (including but not limited to *Citrobacter freundii, Citrobacter koseri,* not differentiated), *Serratia marcescens, Candida albicans, Candida glabrata,* and *Candida tropicalis*.

The infectious agent 1706 can also be bacteria selected from the group consisting of *Acinetobacter baumannii, Actinobacillus* spp., Actinomycetes, *Actinomyces* spp. (including but not limited to *Actinomyces israelii* and *Actinomyces naeslundii*), *Aeromonas* spp. (including but not limited to *Aeromonas hydrophila, Aeromonas veronii* biovar *sobria* (*Aeromonas sobria*), and *Aeromonas caviae*), *Anaplasma phagocytophilum, Alcaligenes xylosoxidans, Actinobacillus actinomycetemcomitans, Bacillus* spp. (including but not limited to *Bacillus anthracis, Bacillus cereus, Bacillus subtilis, Bacillus thuringiensis,* and *Bacillus stearothermophilus*), *Bacteroides* spp. (including but not limited to *Bacteroides fragilis*), *Bartonella* spp. (including but not limited to *Bartonella bacilliformis* and *Bartonella henselae, Bifidobacterium* spp., *Bordetella* spp. (including but not limited to *Bordetella pertussis, Bordetella parapertussis,* and *Bordetella bronchiseptica*), *Borrelia* spp. (including but not limited to *Borrelia recurrentis,* and *Borrelia burgdorferi*), *Brucella* spp. (including but not limited to *Brucella abortus, Brucella canis, Brucella* melintensis and *Brucella suis*), *Burkholderia* spp. (including but not limited to *Burkholderia pseudomallei* and *Burkholderia cepacia*), *Campylobacter* spp. (including but not limited to *Campylobacter jejuni, Campylobacter coli, Campylobacter lari* and *Campylobacter fetus*), *Capnocytophaga* spp., *Cardiobacterium hominis, Chlamydia trachomatis, Chlamydophila pneumoniae, Chlamydophila psittaci, Citrobacter* spp., *Coxiella burnetii, Corynebacterium* spp. (including but not limited to, *Corynebacterium diphtheriae, Corynebacterium jeikeum* and *Corynebacterium*), *Clostridium* spp. (including but not limited to *Clostridium perfringens, Clostridium difficile, Clostridium botulinum* and *Clostridium tetani*),

*Eikenella corrodens*, *Enterobacter* spp. (including but not limited to *Enterobacter aerogenes*, *Enterobacter agglomerans*, *Enterobacter cloacae* and *Escherichia coli*, including opportunistic *Escherichia coli*, including but not limited to enterotoxigenic *E. coli*, enteroinvasive *E. coli*, enteropathogenic *E. coli*, enterohemorrhagic *E. coli*, enteroaggregative *E. coli* and uropathogenic *E. coli*), *Enterococcus* spp. (including but not limited to *Enterococcus faecalis* and *Enterococcus faecium*), *Ehrlichia* spp. (including but not limited to *Ehrlichia chafeensia* and *Ehrlichia canis*), *Erysipelothrix rhusiopathiae*, *Eubacterium* spp., *Francisella tularensis*, *Fusobacterium nucleatum*, *Gardnerella vaginalis*, *Gemella morbillorum*, *Haemophilus* spp. (including but not limited to *Haemophilus influenzae*, *Haemophilus ducreyi*, *Haemophilus aegyptius*, *Haemophilus parainfluenzae*, *Haemophilus haemolyticus* and *Haemophilus parahaemolyticus*, *Helicobacter* spp. (including but not limited to *Helicobacter pylori*, *Helicobacter cinaedi* and *Helicobacter fennelliae*), *Kingella kingii*, *Klebsiella* spp. (including but not limited to *Klebsiella pneumoniae*, *Klebsiella granulomatis* and *Klebsiella oxytoca*), *Lactobacillus* spp., *Listeria monocytogenes*, *Leptospira interrogans*, *Legionella pneumophila*, *Leptospira interrogans*, *Peptostreptococcus* spp., *Moraxella catarrhalis*, *Morganella* spp., *Mobiluncus* spp., *Micrococcus* spp., *Mycobacterium* spp. (including but not limited to *Mycobacterium leprae*, *Mycobacterium tuberculosis*, *Mycobacterium intracellulare*, *Mycobacterium avium*, *Mycobacterium bovis*, and *Mycobacterium marinum*), *Mycoplasm* spp. (including but not limited to *Mycoplasma pneumoniae*, *Mycoplasma hominis*, and *Mycoplasma genitalium*), *Nocardia* spp. (including but not limited to *Nocardia asteroides*, *Nocardia cyriacigeorgica* and *Nocardia brasiliensis*), *Neisseria* spp. (including but not limited to *Neisseria gonorrhoeae* and *Neisseria meningitidis*), *Pasteurella multocida*, *Plesiomonas shigelloides*, *Prevotella* spp., *Porphyromonas* spp., *Prevotella melaninogenica*, *Proteus* spp. (including but not limited to *Proteus vulgaris* and *Proteus mirabilis*), *Providencia* spp. (including but not limited to *Providencia alcalifaciens*, *Providencia rettgeri* and *Providencia stuartii*), *Pseudomonas aeruginosa*, *Propionibacterium acnes*, *Rhodococcus equi*, *Rickettsia* spp. (including but not limited to *Rickettsia rickettsii*, *Rickettsia akari* and *Rickettsia prowazekii*, *Orientia tsutsugamushi* (formerly: *Rickettsia tsutsugamushi*) and *Rickettsia typhi*), *Rhodococcus* spp., *Stenotrophomonas maltophilia*, *Salmonella* spp. (including but not limited to *Salmonella enterica*, *Salmonella typhi*, *Salmonella paratyphi*, *Salmonella enteritidis*, *Salmonella cholerasuis* and *Salmonella typhimurium*), *Serratia* spp. (including but not limited to *Serratia marcesans* and *Serratia liquifaciens*), *Shigella* spp. (including but not limited to *Shigella dysenteriae*, *Shigella flexneri*, *Shigella boydii* and *Shigella sonnei*), *Staphylococcus* spp. (including but not limited to *Staphylococcus aureus*, *Staphylococcus epidermidis*, *Staphylococcus hemolyticus*, *Staphylococcus saprophyticus*), *Streptococcus* spp. (including but not limited to *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae*, *Streptococcus mutans*, *Streptococcus pyogenes*, Group A Streptococci, *Streptococcus pyogenes*, Group B Streptococci, *Streptococcus agalactiae*, Group C Streptococci, *Streptococcus anginosus*, *Streptococcus* equismilis, Group D Streptococci, *Streptococcus bovis*, Group F Streptococci, *Streptococcus anginosus*, and Group G Streptococci), *Spirillum minus*, *Streptobacillus moniliformis*, *Treponema* spp. (including but not limited to *Treponema carateum*, *Treponema petenue*, *Treponema pallidum* and *Treponema endemicum*, *Tropheryma whippelii*, *Ureaplasma urealyticum*, *Veillonella* spp., *Vibrio* spp. (including but not limited to *Vibrio cholerae*, *Vibrio parahemolyticus*, *Vibrio vulnificus*, *Vibrio parahaemolyticus*, *Vibrio vulnificus*, *Vibrio alginolyticus*, *Vibrio mimicus*, *Vibrio hollisae*, *Vibrio fluvialis*, *Vibrio metchnikovii*, *Vibrio damsela* and *Vibrio* furnisii), *Yersinia* spp. (including but not limited to *Yersinia enterocolitica*, *Yersinia pestis*, and *Yersinia pseudotuberculosis*) and *Xanthomonas maltophilia*.

In other embodiments, the infectious agent 1706 can be fungi selected from the genera *Candida* or *Cryptococcus*. For example, the infectious agent 1706 can be fungi or mold selected from the group consisting of *Candida* spp. (including but not limited to *Candida albicans*, *Candida glabrata*, *Candida tropicalis*, *Candida parapsilosis*, and *Candida krusei*), *Aspergillus* spp. (including but not limited to *Aspergillus fumigatous*, *Aspergillus flavus*, *Aspergillus clavatus*), *Cryptococcous* spp. (including but not limited to *Cryptococcus neoformans*, *Cryptococcus gattii*, *Cryptococcus laurentii*, and *Cryptococcus albidus*), *Fusarium* spp. (including but not limited to *Fusarium oxysporum*, *Fusarium solani*, *Fusarium verticillioides*, and *Fusarium proliferatum*), *Rhizopus oryzae*, *Penicillium marneffei*, *Coccidiodes immitis*, and *Blastomyces dermatitidis*.

In some embodiments, the source sample 1704 can comprise or refer to a bacterial culture or a re-suspended bacterial culture derived from a bodily fluid or swab obtained from a patient or subject. For example, the source sample 1704 can comprise or refer to a bacterial culture or a re-suspended bacterial culture derived from a bodily fluid or swab obtained from a patient or subject that has tested positive for bacterial growth between 1 hour and 12 hours prior.

As a more specific example, the source sample 1704 can comprise or refer to a bacterial culture or a re-suspended bacterial culture derived from the blood of a patient or subject that has tested positive for bacterial growth between 1 hour and 12 hours prior. In this example, the source sample 1704 (e.g., re-suspended bacterial culture) can comprise red blood cells. In this case, the source sample 1704 can be referred to as a positive blood culture.

In most cases, positive blood cultures are prepared from the blood of a patient that show symptoms of sepsis. In these cases, blood (e.g., 5 mL to 10 mL) drawn from the patient is transferred into a commercial blood culturing container or vessel that contain bacterial growth media (e.g., 30 mL to 40 mL of growth media). The blood culturing container or vessel can then be incubated at 35° C.±2° C. to allow the bacteria to proliferate. If the patient's blood is contaminated with bacteria, the bacteria will replicate within the container or vessel. A blood culturing system or apparatus can then be used to monitor for bacterial growth (such as by monitoring bacterial $CO_2$ production within the container or vessel). The blood culture tests "positive" for bacterial growth when a critical $CO_2$ threshold has been met. Depending on the pathogen type and growth rate, the blood culture can turn positive between several hours and several days.

In these and other embodiments, the source sample 1704 can comprise or refer to a bacterial culture or a re-suspended bacterial culture derived from another type of bodily fluid such as urine, serum, plasma, saliva, sputum, semen, breast milk, joint fluid, spinal fluid such as cerebrospinal fluid, wound material, mucus, fluid accompanying stool, vaginal secretions, synovial fluid, pleural fluid, peritoneal fluid, pericardial fluid, amniotic fluid, or a combination thereof (with or without blood).

Moreover, the swab obtained from the patient or subject can comprise a wound swab, a rectal swab, a vaginal swab, re-suspended instances of the aforementioned swabs, or a combination thereof.

In some embodiments, the patient or subject can be a human patient or subject. In other embodiments, the patient or subject can be a non-human animal patient or subject.

In additional embodiments, the source sample 1704 can comprise an environmental sample obtained from a stream, river, lake, ocean, contamination site, quarantine zone, an emergency area, or a combination thereof. In other embodiments, the source sample 1704 can comprise a food sample obtained from a food preparation facility, a dining establishment, a waste facility, or a combination thereof.

In certain embodiments, the source sample 1704 can comprise between about $3.6*10^7$ to about $4.7*10^9$ colony forming units per milliliters (CFU/mL) of bacteria. For example, the source sample 1704 can be a positive blood culture comprising between about $3.6*10^7$ to about $4.7*10^9$ CFU/mL of bacteria.

The method 1700 can comprise diluting an aliquot of the source sample 1704 in step 1700A. The aliquot of the source sample 1704 can be diluted by a dilution factor or ratio to yield a diluted sample 1708. The dilution factor can be between about 1:1 to about 1:10. The dilution factor can also be between about 1:10 to about 1:100. For example, the dilution factor can be about 1:30.

The aliquot of the source sample 1704 can be diluted using a dilutive solution 1710. In some embodiments, the dilutive solution 1710 can comprise growth media or a growth inducer. In these and other embodiments, the dilutive solution 1710 can be a solution containing bacto-tryptone, tryptic soy digest, yeast extract, beef extract, cation-adjusted Mueller Hinton Broth (CAMHB), glucose supplemented Mueller Hinton broth (MHG), starch, acid hydrolysate of casein, calcium chloride, magnesium chloride, sodium chloride, blood or lysed blood including lysed horse blood (LHB), CAMHB-LHB, glucose or other carbohydrates, or a combination thereof. The growth inducer can comprise a carbon-based inducer, a nitrogen-based inducer, a mineral, a trace element, a biological growth factor, or any combination thereof. For example, the growth inducer can include but is not limited to a carbohydrate such as glucose or starches, ammonia, magnesium, amino acids, casamino acids, vitamins, peptides, blood, or a combination thereof. In one example embodiment, the dilutive solution 1710 can comprise tryptone, yeast extract, sodium chloride, starch, water, and glucose.

The method 1700 can further comprise detaching the container cap 116 of the sensor apparatus 100 and introducing an aliquot (e.g., ~1 mL or several mLs) of the diluted sample 1708 into the chamber cavity 108 of the sample container 104 in step 1700B. As previously discussed with respect to FIGS. 1B-1D, the sample container 104 of the sensor apparatus 100 can have a chamber cavity 108 defined therein. The chamber cavity 108 can be surrounded by a chamber lateral wall 112.

The sample container 104 can comprise an active sensor 106 coupled to at least part of the chamber lateral wall 112 at a window opening 114 defined along the chamber lateral wall 112 (see, e.g., FIGS. 1B-1D). In certain embodiments, no part of the active sensor 106 extends into the chamber cavity 108. The sample container 104 can be configured to allow the diluted sample 1708 within the chamber cavity 108 to be in fluid contact with the active sensor 106 through at least part of the chamber lateral wall 112 surrounding the window opening 114 (see, e.g., FIGS. 1B-1D).

As previously discussed, the active sensor 106 can be hermetically sealed using film assisted molding (FAM) except for a portion of the active electrode layer 132 (see, e.g., FIGS. 1C, 1D, 2, 3A, 4A-4C, 5A, 6A, 7, and 8A-8B) of the active electrode layer 132 left exposed. The portion of the active electrode layer 132 left exposed by the FAM can be configured or positioned to face the chamber cavity 108 to allow the diluted sample 1708 within the chamber cavity 108 to be in fluid contact with the portion of the active electrode layer 132 left exposed.

The method 1700 can also comprise an optional step 1700A' of cleaning the sensor apparatus 100 including at least the sample container 104 using an alcohol-based disinfectant solution prior to introducing the diluted sample 1708 into the sample container 104. In some embodiments, the alcohol-based disinfectant solution can be an isopropyl alcohol (IPA) solution. The sample container 104 can also be cleaned with IPA in an ultrasonic cleaner using sonication. For example, the sample container 104 can be cleaned with 99.5% IPA with sonication for about 10 minutes (or at least 10 minutes) to prevent environmental contamination.

Alternatively, steps 1700A and 1700B can comprise introducing the dilutive solution 1710 into the chamber cavity 108 of the sample container 104 first and then introducing an aliquot (e.g., ~1 mL) of the source sample 1704 into the chamber cavity 108 filled with the dilutive solution 1710. In this case, the source sample 1704 can be diluted directly in the sample container 104 of the sensor apparatus 100 to yield the diluted sample 1708.

As previously discussed with respect to FIG. 1D, at least part of the container cap 116 can serve as a reference sensor 122. For example, the reference sensor 122 can comprise a reference electrode material 149 and a wicking component 110 extending through the container cap 116 and into the chamber cavity 108 of the sample container 104. When the chamber cavity 108 is filled with the diluted sample 1708, at least some of the diluted sample 1708 can be drawn up by the wicking component 110 in the direction of the reference electrode material 149.

In certain embodiments, the reference electrode material 149 can be deposited or otherwise positioned on the wick proximal end 152 of the wicking component 110. For example, the reference electrode material 149 can be a cured or hardened silver-silver chloride ink deposited or otherwise positioned on the wick proximal end 152 of the wicking component 110. The reference electrode material 149 can protrude beyond the container cap 116 such that at least a portion of the reference electrode material 149 can be accessed by the reference electrode contact 1308 of the reader apparatus 190.

The method 1700 can also comprise coupling the container cap 116 to the sample container 104 once the chamber cavity 108 of the sample container 104 is at least partially filled with the diluted sample 1708 and placing the sensor apparatus 100 into the reader apparatus 190 in step 1700C.

As previously discussed with respect to FIGS. 13A-13D, the reader apparatus 190 can be in electrical contact with both the active sensor 106 and the reference sensor 122 when the sensor apparatus 100 is placed within the reader apparatus 190. For example, when the sensor apparatus 100 is positioned within the container receiving space 1306 (see, e.g., FIG. 13B), the active electrode contact 1310 of the reader apparatus 190 can be placed or moved into contact with a conductive contact or conductive substrate layer of the active sensor 106 and the reference electrode contact 1308 of the reader apparatus 190 can be placed or moved into contact with the reference electrode material 149 positioned on the container cap 116 (see, e.g., FIG. 1D). In some embodiments, the reference electrode contact 1308 and the active electrode contact 1310 can comprise one or more conductive pogo or spring-loaded pins, conductive leaf contacts, or a combination thereof. More specifically, the conductive pogo pins or leaf contacts can be made of copper, nickel, stainless steel, or alloys thereof.

The reference electrode contact 1308 and the active electrode contact 1310 can electrically couple the reference sensor 122 and the active sensor 106, respectively, with the signal readout control unit 1303 and/or certain other readout electronic components within the reader apparatus 190. For example, the readout electronic components can comprise one or more high input impedance op-amps and analog-to-digital converters (ADCs). One or more processors of the signal readout control unit 1303 can read or process signals obtained from the sensor apparatus 100 in real-time.

In certain embodiments, the signal obtained from the sensor apparatus 100 can be a voltage difference (V) between the reference electrode material 149 and the active electrode layer 132 or active electrode material of the sensor apparatus 100. The signal can change in real-time as the solution characteristic of the diluted sample 1708 within the sample container 104 changes. In this manner, the reader apparatus 190 can monitor the change in the solution characteristic of the diluted sample 1708 within the sample container 104 over time.

FIG. 17 also illustrates that the system 1702 for preparing the standardized inoculum 1726 can comprise the sensor apparatus 100 and the reader apparatus 190. In some embodiments, the system 1702 can also comprise a computing device 1712 configured to connect to and communicate with the reader apparatus 190. For example, the computing device 1712 can be a laptop or desktop computer, a tablet device, a mobile device, or a handheld device.

In some embodiments, the computing device 1712 can display data or information generated by the reader apparatus 190. In addition, the reader apparatus 190 can offload certain processing tasks (e.g., signal processing tasks) to the computing device 1712.

The reader apparatus 190, the computing device 1712, or a combination thereof can receive a user input from a user of the system 1702 (e.g., a laboratory technician or clinician) concerning the source sample 1704, the infectious agent 1706, a desired concentration of the standardized inoculum 1726, or a combination thereof.

For example, the reader apparatus 190 can comprise a touchscreen display 1302 (see also, FIGS. 13A-13C). A user of the system 1702 can apply a user input in the form of a touch input to the touchscreen display 1302 to make a selection or answer a query concerning the source sample 1704, the infectious agent 1706, the desired concentration of the standardized inoculum 1726, or a combination thereof. Similarly, the computing device 1712 can also comprise a touchscreen display 1714 and a user of the system 1702 can apply a user input in the form of a touch input to the touchscreen display 1714 of the computing device 1712 to make a selection or answer a query concerning the source sample 1704, the infectious agent 1706, the desired concentration of the standardized inoculum 1726, or a combination thereof.

The method 1700 can further comprise receiving a user input at the reader apparatus 190 (or the computing device 1712 when the computing device 1712 is connected to or in wireless communication with the reader apparatus 190) concerning an identity of the species of the infectious agent 1706 within the source sample 1704 in step 1700D. For example, the user can apply a touch input to the touchscreen display 1302 of the reader apparatus 190 (or the touchscreen display 1714 of the computing device 1712) to select the species of the infectious agent 1706 from a graphical user interface (GUI) (e.g., a prepopulated dropdown menu) comprising a plurality of species names. The reader apparatus 190 can also receive the identity of the species of the infectious agent 1706 from the computing device 1712 or another device connected to or in wireless communication with the reader apparatus 190.

Step 1700D can also comprise receiving a user input at the reader apparatus 190 (or the computing device 1712) concerning another classification type or a characteristic of the infectious agent 1706 within the source sample 1704. The other classification type can include a genus, a family, an order, a class, a phylum, a kingdom, and/or a domain of the infectious agent 1706 in the source sample 1704.

In some embodiments, the characteristic of the infectious agent 1706 can be a response of the infectious agent 1706 to a Gram stain test. For example, step 1700D can comprise performing a Gram stain test and identifying the infectious agent 1706 as Gram-positive or Gram-negative bacteria.

The infectious agent 1706 can be identified using at least one of a biochemical test (e.g., a test for metabolism or a test for specific enzymes), mass spectrometry, genotyping, proteomic techniques, phenotypic analysis from culture plates, and test kits comprising phages. More specifically, the infectious agent 1706 can be identified using a rapid ID technique such as matrix-assisted laser desorption ionization time-of-flight (MALDI-TOF) mass spectrometry directly from a positive blood culture. In certain embodiments, the species of the infectious agent 1706 can be identified within an hour of a blood culture flagging positive. In these and other embodiments, the species of the infectious agent 1706 can be identified but the particular strain of the infectious agent 1706 can be left unidentified.

The method 1700 can also comprise one or more processors of the reader apparatus 190 retrieving a look-up table (LUT) stored in a memory or storage unit of the reader apparatus 190 based on the classification or characteristic of the infectious agent 1706 in step 1700E. The LUT can be retrieved from a database stored in the memory or storage unit of the reader apparatus 190.

The LUTs can be tables or matrices that associate solution characteristic change amounts (or thresholds amounts 1718) with desired concentrations 1720. For example, the reader apparatus 190 can retrieve a species-specific LUT 1716 based on the species of the infectious agent 1706 identified by the user. As a more specific example, the species of the infectious agent 1706 within a source sample 1704 can be identified as the bacteria *Escherichia coli* (ECo). In this example, the reader apparatus 190 can retrieve the species-specific LUT 1716 for ECo from a database of LUTs.

As previously discussed, besides species, the LUTs can be organized by genus, family, order, class, phylum, kingdom, and/or domain. The LUTs can also be organized by microbial characteristics (such as Gram-type) or functional capabilities (such as the ability to hydrolyze certain proteins or molecules). The LUTs can be updated and new LUTs can be added by updating the software or firmware of the reader apparatus 190.

In alternative embodiments, a universal LUT can be selected and retrieved when the species of the infectious agent 1706 in the source sample 1704 is not known or has not been ascertained.

As will be discussed in more detail in the following sections, the species-specific LUT 1716, the universal LUT, and other LUTs (e.g., LUTs organized by other classifications or microbial characteristics) can be generated from multiple strain-specific LUTs 1900 (see FIG. 19) representing data measured from multiple reference samples monitored over time. When the LUT is a species-specific LUT 1716, each of the multiple reference samples can comprise a reference infectious agent of the same species as the infectious agent 1706 in the source sample 1704. When the LUT is a universal LUT or another type of inter-species LUT, at least one of the multiple reference samples can comprise a reference infectious agent of a different species from the infectious agent 1706 in the source sample 1704.

The method 1700 can further comprise the reader apparatus 190 setting a threshold amount 1718 using the LUT (e.g., the species-specific LUT 1716) based on a desired concentration 1720 of the standardized inoculum 1726 in step 1700F. The threshold amount 1718 can represent a target amount by which a solution characteristic of the diluted sample 1708 is required to change in order for the concentration of the infectious agent 1706 in the diluted sample 1708 to reach the desired concentration 1720. The threshold amount 1718 can also represent a limit or maximum amount by which a solution characteristic of the diluted sample 1708 is permitted to change (e.g., a $\Delta V$ of approximately −0.40 or a $\Delta pH$ of approximately −0.20) before the concentration of the infectious agent 1706 in the diluted sample 1708 exceeds the desired concentration 1720.

In some embodiments, the threshold amount 1718 can be a threshold range (e.g., a $\Delta V$ of between approximately −0.40 and −0.50 or a $\Delta pH$ of between approximately −0.15 and −0.25). The threshold amount 1718 can be automatically set by the reader apparatus 190 based on the retrieved LUT (e.g., the species-specific LUT 1716) in response to an input (e.g., a user input) received by the reader apparatus 190 concerning the desired concentration 1720. For example, a user of the system 1702 can input the desired concentration 1720 by selecting the desired concentration 1720 (e.g., 0.5 McFarland sample) from a prepopulated list of concentrations. In other embodiments, the desired concentration 1720 can be transmitted to the reader apparatus 190 by the computing device 1712 or another device connected to or in communication with the reader apparatus 190. The desired concentration 1720 can also be set in advance according to certain laboratory or diagnostic protocols.

Besides look-up tables, the method 1700 can also comprise determining the concentration of the infectious agent 1706 in the diluted sample 1708 using the algorithms, equations, and mathematical expressions disclosed in International Patent Publication No. WO2020/117650, published on Jun. 11, 202, the content of which is hereby incorporated by reference in its entirety.

Step 1700F can further comprise using the reader apparatus 190 to monitor a change in a solution characteristic of the diluted sample 1708 in step 1700G. As previously discussed, the reader apparatus 190 can monitor the solution characteristic of the diluted sample 1708 by obtaining a signal from the sensor apparatus 100. The signal can be a voltage difference (V) between the reference electrode material 149 and the active electrode layer 132 or active electrode material of the sensor apparatus 100 filled with the diluted sample 1708. The signal can change in real-time as the solution characteristic of the diluted sample 1708 within the sample container 104 changes.

In some embodiments, the solution characteristic monitored is the oxidation reduction potential (ORP) of the diluted sample 1708. In these embodiments, the sensor apparatus 100 used has an active sensor 106 covered in part by a redox-sensitive active electrode layer 132 (e.g., platinum or gold).

In other embodiments, the solution characteristic monitored is the pH of the diluted sample 1708. In these embodiments, the sensor apparatus 100 used has an active sensor 106 covered in part by a pH-sensitive layer (e.g., a platinum oxide layer 418, see FIG. 4D).

The solution characteristic of the diluted sample 1708 can change as the amount of ions or the amount of electro-active redox species in solution change due to the energy use, oxygen uptake or release, growth, or metabolism of the infectious agent 1706 in the diluted sample 1708. For example, the amount of electro-active redox species in the diluted sample 1708 can change as a result of cellular activity (e.g., microbial aerobic or anaerobic respiration) undertaken by the infectious agents 1706 in the diluted sample 1708.

The solution characteristic of the diluted sample 1708 can be monitored in the absence of any exogenous reporter molecules added to the diluted sample 1708.

The amount of electron donors (e.g., the amount of energy carriers such as nicotinamide adenine dinucleotide (NADH) and flavin adenine dinucleotide ($FADH_2$)) in the diluted sample 1708 can change due to the growth of the infectious agent 1706 in the diluted sample 1708. Moreover, the amount of oxygen depleted in the diluted sample 1708 due to aerobic respiration can change due to the growth of the infectious agent 1706 in the diluted sample 1708.

As a more specific example, during bacterial metabolism, very reduced molecules can be produced that readily give up electrons ($e^-$) to the redox-sensitive active electrode layer 132 exposed to the diluted sample 1708. While the reference electrode material 149 of the reference sensor 122 maintains a fixed voltage, the bacteria within the diluted sample 1708 change the solution ORP of the diluted sample 1708 as electrons accumulate on the surface of the redox-sensitive active electrode layer 132. Consequently, the overall voltage becomes more negative.

As another example, the amount of $H^+$ ions in the diluted sample 1708 can change as a result of cellular activity undertaken by the infectious agents 1706 in the diluted sample 1708.

Step 1700F can also comprise incubating the diluted sample 1708 within the sample container 104 of the sensor apparatus 100 to an incubation temperature 1722 using a heating block 1318 of the reader apparatus 190. The diluted sample 1708 can be incubated within the sample container 104 of the sensor apparatus 100 while the solution characteristic of the diluted sample 1708 is being monitored. The diluted sample 1708 can be incubated when the diluted sample 1708 is in fluid contact with the active sensor 106 through at least part of the chamber lateral wall 112.

The incubation temperature 1722 can be between approximately 30° C. and 40° C. In some embodiments, the incubation temperature 1722 can be between approximately 33° C. and 37° C. (or about 35° C.±2° C.).

The method 1700 can further comprise generating an alert or notification when the solution characteristic of the diluted sample 1708 within the sensor apparatus 100 changes by the threshold amount 1718 in step 1700G. The alert or notification can indicate the successful preparation of the standardized inoculum 1726 of the desired concentration 1720 from the diluted sample 1708.

In some embodiments, the alert or notification can be generated by the reader apparatus 190 and displayed on the touchscreen display 1302 of the reader apparatus 190. In other embodiments, the alert or notification can be displayed on the touchscreen display 1714 of the computing device 1712. The alert or notification can be a message informing the user that the solution characteristic of the diluted sample 1708 has changed by the threshold amount 1718 or that the infectious agents 1706 within the sample container 104 of the sensor apparatus 100 have reached the desired concentration 1720. The alert or notification can also comprise an audible alert, a visual/graphic alert, a haptic alert, or a combination thereof.

In some embodiments, the amount of time elapsed between the dilution step (step 1700A) and the alert generation step (step 1700G) can be between about 60 minutes and about 120 minutes. For example, the dilution step can occur as soon as a blood culture is flagged positive for microbial growth.

In other embodiments, the amount of time elapsed between the dilution step and the alert generation step can be between about 120 minutes and 180 minutes.

The method 1700 can further comprise using a cooling component 1320 within the reader apparatus 190 to cool the standardized inoculum 1726 within the sensor apparatus 100 to a cooling temperature 1724 in step 1700H. In some embodiments, the cooling temperature can be between about 15° C. and 20° C. (e.g., about 15° C.±2° C.).

In alternative embodiments, the sensor apparatus 100 containing the standardized inoculum 1726 of the desired concentration 1720 can be cooled by being taken out of the reader apparatus 190 and being placed in an ice bath. The sensor apparatus 100 containing the standardized inoculum 1726 of the desired concentration 1720 can be cooled by being placed in a refrigerator or freezer or a standalone cooling device.

In some embodiments, the standardized inoculum 1726 can be a 0.5 McFarland inoculum comprising between about $1*10^8$ to about $2*10^8$ colony forming units per milliliters (CFU/mL) of bacteria. More specifically, the standardized inoculum 1726 can be a 0.5 McFarland inoculum comprising about $1.5*10^8$ CFU/mL of bacteria.

The standardized inoculum 1726 (e.g., the 0.5 McFarland inoculum) can then be used directly for antimicrobial susceptibility testing using manual disk diffusion or diluted further for automated AST platforms. For example, the standardized inoculum 1726 prepared using the method 1700 and system 1702 disclosed herein can be subjected to manual Kirby-Bauer disk diffusion AST or an automated AST platform such as the VITEK®2 platform.

Tables 1 and 2 below show the results of experiments conducted to evaluate the performance of the method 1700 disclosed herein compared against traditional inoculum preparation workflows using microbial subcultures.

Both the present method 1700 and traditional microbial subculturing techniques were used to prepare standardized 0.5 McFarland inocula for AST using Kirby-Bauer disk diffusion (see Table 1) and the automated VITEK2 GN81 AST platform (see Table 2).

Two sets of standardized 0.5 McFarland inocula were prepared from 23 different positive blood culture (PBC) samples comprising seven different species of bacteria. The 23 PBC samples included six samples of *Escherichia coli* (ECo), two samples of *Enterobacter cloacae* (ECl), three samples of *Klebsiella pneumoniae* (KPn), four samples of *Klebsiella oxytoca* (KOx), two samples of *Citrobacter freundii* (CFr), four samples of *Serratia marcescens* (SMa), and two samples of *Klebsiella aerogenes* (KAe).

The first set was prepared using the presently disclosed method 1700 (sample preparation time: between 60 minutes and 180 minutes) and the second set was prepared using traditional microbial subculturing techniques (sample preparation time: between 18 hours to 24 hours). Both sets of inocula were subjected to susceptibility testing using the antibiotics listed in Tables 1 and 2. The testing was conducted using the automated VITEK®2 GN81 AST platform (see Table 1) and manual Kirby-Bauer disk diffusion (see Table 2).

In total, 296 minimum inhibitory concentrations (MICs) from the VITEK®2 GN81 platform and 224 zone sizes on disk diffusion were evaluated. The total number of isolates tested for each antimicrobial along with the number of isolates deemed resistant (R), susceptible (S), and intermediate (I) are shown.

Overall performance of the method 1700 and system 1702 disclosed herein with respect to AST showed essential agreement (EA) and categorical agreement (CA) of 96.6% and 95.3%, respectively, for the automated VITEK®2 GN81 platform (see Table 1) and CA of 94.6% for Kirby-Bauer disk diffusion (see Table 2).

The minor error (mE) rate was 4.4% for the automated VITEK®2 GN81 platform (see Table 1) and 4.9% for Kirby-Bauer disk diffusion (see Table 2). The major error (ME) rate was 0.5% for the automated VITEK®2 GN81 platform (see Table 1) and 0.7% for Kirby-Bauer disk diffusion (see Table 2). There were no very major errors (VME) observed using either AST method.

TABLE 1

VITEK ® C GN81 AST results for standardized inocula prepared using the presently disclosed method and traditional culturing methods.

| Antibiotic | # isolates | # R | # S | # I | # in EA | # in CA | # mE | # ME | # VME | % EA | % CA |
|---|---|---|---|---|---|---|---|---|---|---|---|
| Ampicillin | 6 | 5 | 1 | 0 | 6 | 6 | 0 | 0 | 0 | 100% | 100% |
| Cefazolin | 10 | 10 | 0 | 0 | 9 | 10 | 0 | 0 | 0 | 90% | 100% |
| Cefoxitin | 13 | 6 | 7 | 0 | 13 | 13 | 0 | 0 | 0 | 100% | 100% |
| Ceftriaxone | 23 | 11 | 12 | 0 | 21 | 22 | 0 | 1 | 0 | 91.3% | 95.7% |

TABLE 1-continued

VITEK ® C GN81 AST results for standardized inocula prepared using the presently disclosed method and traditional culturing methods.

| Antibiotic | # isolates | # R | # S | # I | # in EA | # in CA | # mE | # ME | # VME | % EA | % CA |
|---|---|---|---|---|---|---|---|---|---|---|---|
| Ceftazidime | 23 | 9 | 14 | 0 | 22 | 23 | 0 | 0 | 0 | 95.7% | 100% |
| Cefepime | 23 | 5 | 16 | 2 | 20 | 18 | 5 | 0 | 0 | 87% | 78.3% |
| Amoxicillin-Clavulanic acid | 13 | 6 | 6 | 1 | 13 | 13 | 0 | 0 | 0 | 100% | 100% |
| Piperacillin-tazobactam | 9 | 3 | 5 | 1 | 8 | 8 | 1 | 0 | 0 | 88.9% | 88.9% |
| Meropenem | 21 | 6 | 15 | 0 | 20 | 21 | 0 | 0 | 0 | 95.2% | 100% |
| Gentamicin | 23 | 2 | 20 | 1 | 23 | 20 | 3 | 0 | 0 | 100% | 87% |
| Tobramycin | 23 | 3 | 18 | 2 | 23 | 22 | 1 | 0 | 0 | 100% | 95.7% |
| Amikacin | 23 | 1 | 22 | 0 | 23 | 22 | 1 | 0 | 0 | 95.7% | 100% |
| Ciprofloxacin | 23 | 10 | 13 | 0 | 23 | 22 | 1 | 0 | 0 | 100% | 95.7% |
| Levofloxacin | 23 | 10 | 12 | 1 | 23 | 22 | 1 | 0 | 0 | 100% | 95.7% |
| Tetracycline | 23 | 7 | 15 | 1 | 23 | 22 | 1 | 0 | 0 | 100% | 95.7% |
| Trimethoprim-sulfamethoxazole | 17 | 6 | 11 | 0 | 17 | 17 | 0 | 0 | 0 | 100% | 100% |
| TOTAL: | 296 | 100 | 187 | 9 | 286 | 282 | 13 (4.4%) | 1 (0.5%) | 0 (0%) | 96.6% | 95.3% |

TABLE 2

Disk diffusion AST results for standardized inocula prepared using the presently disclosed method and traditional culturing methods.

| Antibiotic | # isolates | # R | # S | # I | # in CA | # mE | # ME | # VME | % CA |
|---|---|---|---|---|---|---|---|---|---|
| Ampicillin | 6 | 5 | 1 | 0 | 6 | 0 | 0 | 0 | 100% |
| Cefazolin | 13 | 11 | 2 | 0 | 13 | 0 | 0 | 0 | 100% |
| Cefoxitin | 13 | 5 | 7 | 1 | 13 | 0 | 0 | 0 | 100% |
| Ceftriaxone | 23 | 11 | 11 | 1 | 22 | 1 | 0 | 0 | 95.7% |
| Cefepime | 23 | 7 | 13 | 3 | 21 | 2 | 0 | 0 | 91.3% |
| Amoxicillin-Clavulanic acid | 13 | 7 | 6 | 0 | 13 | 0 | 0 | 0 | 100% |
| Piperacillin-tazobactam | 18 | 3 | 14 | 1 | 18 | 0 | 0 | 0 | 100% |
| Meropenem | 23 | 5 | 16 | 2 | 21 | 1 | 1 | 0 | 91.3% |
| Ertapenem | 23 | 5 | 14 | 4 | 19 | 4 | 0 | 0 | 82.6% |
| Gentamicin | 23 | 2 | 20 | 1 | 22 | 1 | 0 | 0 | 95.7% |
| Tobramycin | 23 | 3 | 19 | 1 | 21 | 2 | 0 | 0 | 91.3% |
| Levofloxacin | 23 | 11 | 11 | 1 | 23 | 0 | 0 | 0 | 100% |
| TOTAL: | 224 | 75 | 134 | 15 | 212 | 11 (4.9%) | 1 (0.7%) | 0 (0%) | 94.6% |

Of the 13 mEs observed on the VITEK®2 GN81 platform (see Table 1), five occurred in cefepime, three in gentamicin, and one each in piperacillin-tazobactam, ciprofloxacin, levofloxacin, tetracycline, and tobramycin. The results of 16 antibiotics on the VITEK®2 GN81 were evaluated and all scored ≥90% in EA and CA, except for cefepime which scored 87% and 78%, respectively, and piperacillin-tazobactam which scored 88.9% for both EA and CA.

Of the 11 mEs in disk diffusion (see Table 2), four occurred in ertapenem, two each in cefepime and tobramycin, and one each in ceftriaxone, gentamicin, and meropenem. All 12 antibiotics tested by disk diffusion scored ≥90% in CA, except for ertapenem which scored 82.6%.

Both MEs encountered were confined to a single isolate—a KOx harboring the KPC-3 gene. The ME on the VITEK®2 GN81 platform occurred in ceftriaxone and the ME in disk diffusion occurred in meropenem. Ceftriaxone tested susceptible (MIC=1) with the control 0.5 McFarland inoculum (prepared using traditional techniques) and resistant (MIC=4) with the inoculum prepared using the present method 1700. Similarly, meropenem tested susceptible (zone size of 23 mm) using the control 0.5 McFarland inoculum and resistant (zone size of 19 mm) using the inoculum prepared using the present method 1700.

For the acceptable performance of an antimicrobial susceptibility test, the Food and Drug Administration (FDA) recommends the categorial agreement should be ≥90%, with mEs ≤10%, MEs ≤3%, and VMEs ≤1.5%. The combined results from the evaluations performed on the standardized inocula prepared using the method 1700 and system 1702 disclosed herein satisfy these recommended performance guidelines.

One technical problem faced by the applicants is how to prepare a 0.5 McFarland inoculum that could be used by clinics or laboratories that utilize different AST techniques or methodologies. Another technical challenge faced by the applicants is how to prepare a standardized inoculum that meets AST performance guidelines set by governmental agencies such as the FDA. One technical solution discovered and developed by the applicants is the method 1700 and system 1702 disclosed herein where a diluted sample is introduced into a sensor apparatus 100 fabricated as a container having both the active sensor 106 and the reference sensor 122 integrated as part of the container. The sensor apparatus 100 is then placed into a benchtop reader apparatus 190 that can be used to monitor the solution characteristic of the diluted sample over time and generate an alert or notification when the standardized inoculum is prepared.

Figure 18:
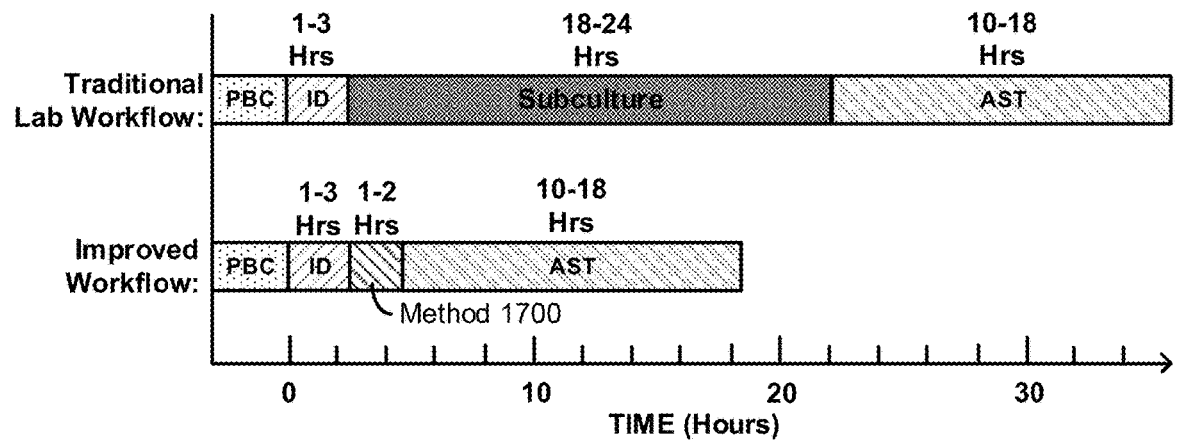
FIG. 18 illustrates the difference between a traditional AST laboratory workflow and the improved AST workflow disclosed herein.

FIG. 18 illustrates the amount of time saved when a laboratory or clinical AST workflow adopts the presently disclosed method 1700 for generating a standardized inoculum 1726 versus a traditional workflow involving microbial subcultures. The presently disclosed method 1700 replaces the time-consuming (e.g., between 18-24 hours) and labor-intensive subculture step with an automated and rapid (e.g., between 1-2 hours) inoculum generation procedure using the components of the system 1702 (e.g., the sensor apparatus 100 and the reader apparatus 190) disclosed herein.

As previously disclosed, a standardized inoculum 1726 can be generated from a diluted positive blood culture as soon as the microorganism (e.g., bacterial species) is identified using rapid identification techniques such as matrix-assisted laser desorption ionization time-of-flight (MALDI-TOF) mass spectrometry.

Figure 19:
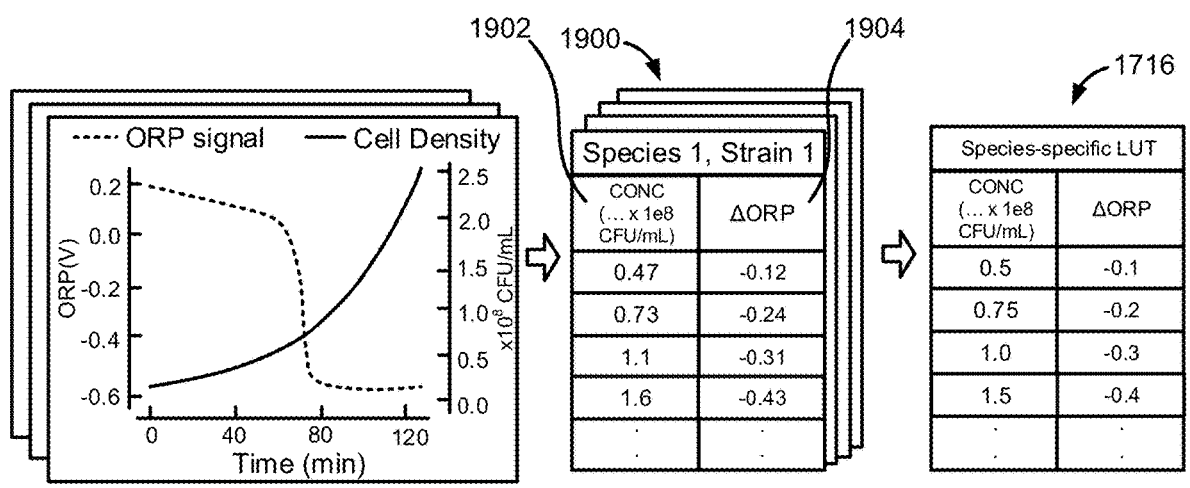
FIG. 19 illustrates a species-specific look-up table (LUT) generated from a plurality of strain-specific LUTs.

FIG. 19 illustrates that a species-specific LUT 1716 can be generated from multiple strain-specific LUTs 1900 representing data obtained from multiple reference samples monitored over time. The multiple reference samples can comprise reference infectious agents of different strains. The reference infectious agents can be of the same species as the infectious agent 1706 within the source sample 1704.

For example, a species-specific LUT 1716 can be generated for *Serratia marcescens* (SMa) from multiple strain-specific LUTs 1900 including LUTs representing the CDC-27 strain of SMa, the CDC-91 strain of SMa, the CDC-99 strain of SMa, the CDC-121 strain of SMa, the CDC-122 strain of SMa, the CDC-130 strain of SMa, or a combination thereof.

Also, as an example, a species-specific LUT 1716 can be generated for *Escherichia coli* (ECo) from multiple strain-specific LUTs 1900 including LUTs representing the PSC-26 strain of ECo, the PSC-18 strain of ECo, the PSC-66 strain of ECo, the PSC-72 strain of ECo, the CDC-13 strain of ECo, the CDC-19 strain of ECo, or a combination thereof.

The reference samples can be prepared by re-suspending infectious agent colonies from an infectious agent culture plate into growth media to reach an initial concentration. For example, the initial concentration of the reference infectious agents can be approximately $1*10^7$ CFU/mL.

Each of the strain-specific LUTs 1900 can associate reference sample concentrations 1902 with solution characteristic change amounts 1904. The solution characteristic change amounts 1904 can be obtained from monitoring the change in the solution characteristic of a reference sample comprising a particular strain of an infectious agent over a period of time. In some embodiments, the solution characteristic of each of the reference samples can be monitored using the reader apparatus 190 and the sensor apparatus 100 filled with the reference sample. In other embodiments, an ORP probe or pH probe can be used to monitor the solution characteristic of the reference samples over time. The reference samples can also be incubated to between approximately 33° C. and 37° C. (or about 35° C.±2° C.).

The reference sample concentrations 1902 can be determined by conducting sample enumeration assays of the reference sample over the same period of time that the solution characteristic of the reference sample is monitored.

A sample enumeration assay can be a test or measurement conducted in order to determine a concentration of a reference infectious agent in a reference sample at a particular point in time. The concentration of the reference infectious agent in the reference sample can increase over a period of time as the reference samples are incubated and the growth media provides nutrients for the reference infectious agent.

In some embodiments, the sample enumeration assay can refer to an optical density (O.D.) measurement, a plate count assay, or a flow cytometry assay. In other embodiments, the sample enumeration assay can be other tests or measurements for determining a concentration of a reference infectious agent in a reference sample. For example, the sample enumeration assay can be an O.D. measurement conducted at a wavelength of 600 nm (OD600 measurements) using a spectrophotometry device or system.

The sample enumeration assays can be conducted concurrently with the monitoring and recording of the changes in the solution characteristic of the reference samples. In some embodiments, the sample enumeration assays (e.g., O.D. measurements) can be conducted immediately before or immediately after changes in the solution characteristic of the reference samples are recorded.

In other embodiments, the sample enumeration assays (e.g., O.D. measurements) can be taken at the same time intervals as measurements of the changes in the solution characteristics of the reference samples. As a more specific example, an O.D. measurement can be conducted on the reference sample and a solution characteristic change of the same reference sample can be recorded every few minutes.

The results of the sample enumeration assays can also be converted to reference sample concentrations 1902 using a conversion factor. For example, the results of O.D. measurements can be converted to reference sample concentrations 1902 (expressed as CFU/mL) by multiplying the results of the O.D. measurements by a numerical conversion factor. The conversion factors are usually instrument-dependent and vary from instrument to instrument.

In some embodiments, the species-specific LUT 1716 can be generated by taking an average of all solution characteristic change amount 1904 across multiple strain-specific LUTs 1900 to yield an averaged solution characteristic change amount. Each of the solution characteristic change amounts can then be associated with a reference sample concentration 1902.

The species-specific LUT 1716 can also be generated by taking an average of all reference sample concentrations 1902 across multiple strain-specific LUTs 1900 to yield an averaged sample concentration. Each of the averaged sample concentrations can then be converted into McFarland standard values and each of those values can be associated with a solution characteristic change amount 1904 or an averaged solution characteristic change amount.

The species-specific LUT 1716 can also be generated using any of the methods disclosed in U.S. Patent Publication No. US2019/0293529 published on Sep. 26, 2019, the content of which is hereby incorporated by reference in its entirety.

Although FIG. 19 illustrates a species-specific LUT 1716 generated from multiple strain-specific LUTs 1900, it is contemplated by this disclosure that other types of LUTs based on classification-type or other microbial characteristics can also be generated from multiple underlying LUTs. For example, a Gram-positive or Gram-negative LUT can be generated from multiple LUTs representing data obtained from multiple reference samples comprising Gram-positive or Gram-negative bacteria of various species. Also, as an example, an order-specific LUT (e.g., an Enterobacterales LUT) can be generated from multiple species-specific LUTs representing data obtained from multiple reference samples comprising bacteria of different species from the order.

Figure 20A:
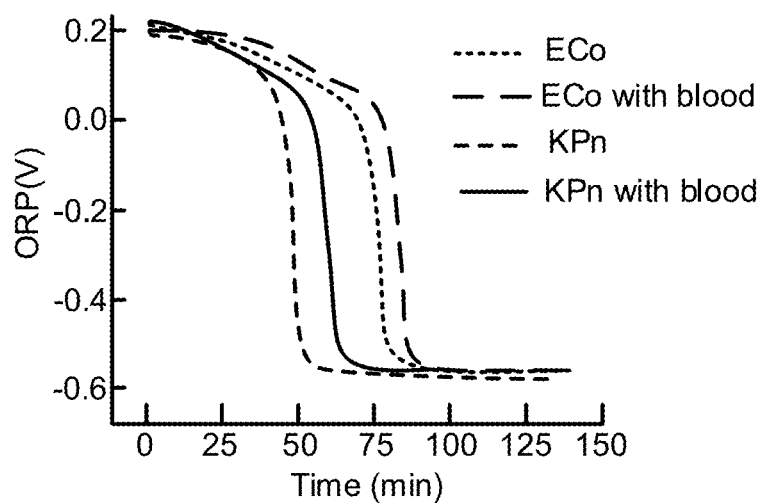
FIG. 20A illustrates ORP growth curves for two Gram-negative bacteria re-suspended in growth media with and without blood cells.

FIG. 20A illustrates ORP growth curves for two Gram-negative bacteria, *Escherichia coli* (ECo) and *Klebsiella pneumoniae* (KPn), re-suspended in growth media with and without blood cells including red blood cells. The Gram-negative bacteria re-suspended in growth media with blood cells were prepared to mimic a positive blood culture obtained from a patient comprising such bacteria.

The ORP growth curves represent the change in ORP of diluted samples comprising ECo (with and without blood) and KPn (with and without blood). Each diluted sample was introduced into a sensor apparatus 100 that was subsequently placed into the reader apparatus 190 for monitoring over time.

As shown in FIG. 20A, the presence of blood cells, including red blood cells, in the diluted samples did not interfere with the ORP measurements and all growth curves exhibited the expected lag phase at the outset followed by the exponential phase and ending in the stationary phase. Also, as expected, the voltage dropped due to cellular activity undertaken by the bacteria in solution.

Figure 20B:
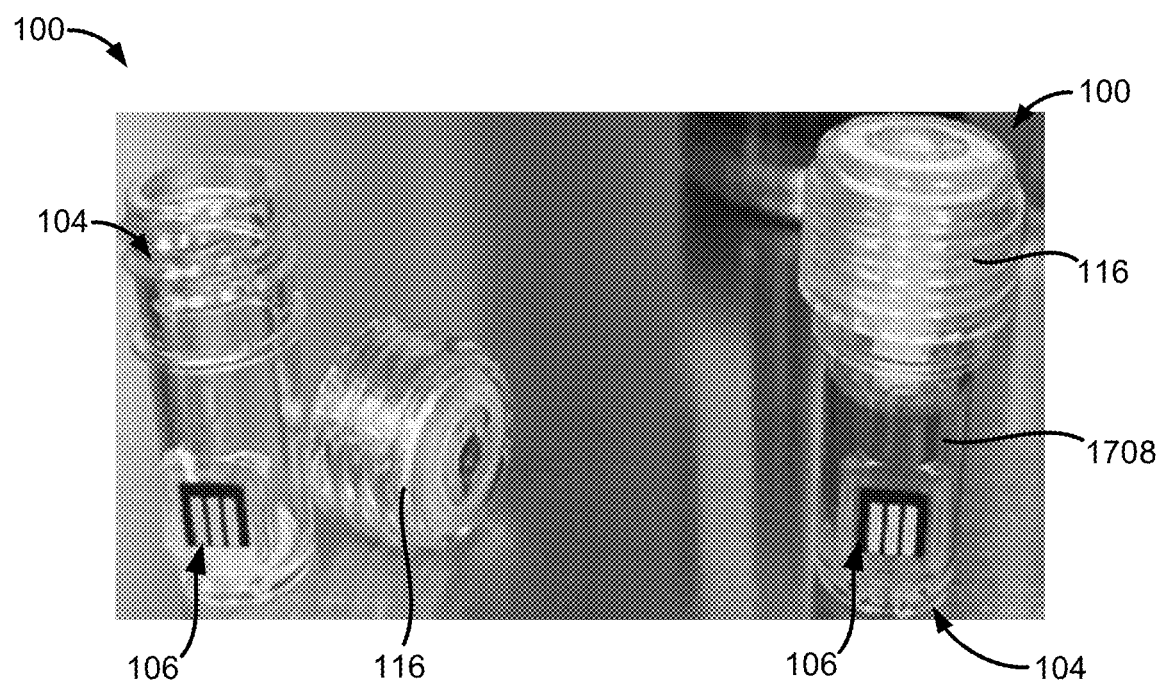
FIG. 20B is a black-and-white image showing an empty sensor apparatus with a container cap of the sensor apparatus detached from a sample container of the sensor apparatus. Also shown is an assembled sensor apparatus filled with a diluted sample comprising red blood cells.

FIG. 20B is a black-and-white image showing an empty sensor apparatus 100 with a container cap 116 of the sensor apparatus 100 detached from the sample container 104 and an assembled sensor apparatus 100 filled with a diluted sample 1708 comprising red blood cells.

One technical problem faced by the applicants is how to design an automated system for preparing a standardized inoculum from source samples that comprise cells (e.g., red blood cells) or molecules that normally would interfere with how such samples are assayed by traditional diagnostic equipment. One technical solution discovered and developed by the applicants is the system 1702 disclosed herein where the ORP or pH of a diluted source sample is monitored using the particular active sensor 106 and reference sensor 122 combination disclosed herein. Numerous PBC samples were used to generate standardized inocula that met desired concentration targets or target ranges.

Figure 21A:
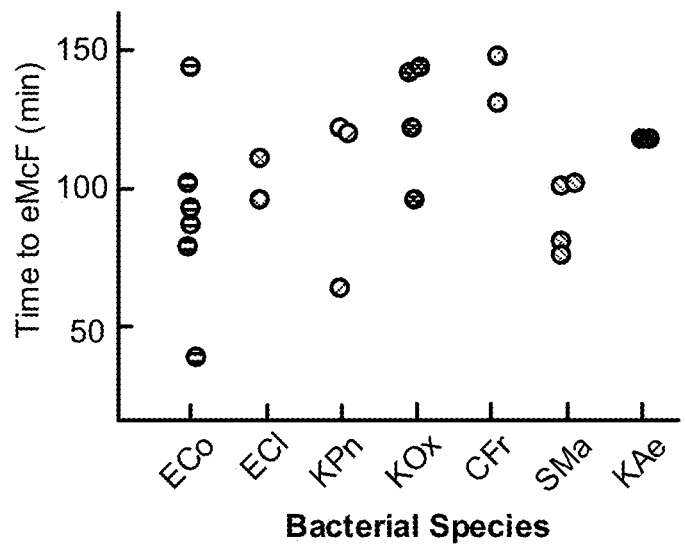
FIG. 21A is a dot plot showing the amount of time it took to generate standardized inocula from 23 different positive blood culture samples comprising seven different species of bacteria.

FIG. 21A is a dot plot showing the amount of time it took to prepare standardized inocula from 23 different positive blood culture (PBC) samples comprising seven different species of bacteria. Each of the standardized inocula was prepared using the method 1700 and system 1702 disclosed herein. The 23 PBC samples included six samples of *Escherichia coli* (ECo), two samples of *Enterobacter cloacae* (ECl), three samples of *Klebsiella pneumoniae* (KPn), four samples of *Klebsiella oxytoca* (KOx), two samples of *Citrobacter freundii* (CFr), four samples of *Serratia marcescens* (SMa), and two samples of *Klebsiella aerogenes* (KAe). The desired concentration of each of the standardized inocula was set at $1.5*10^8$ CFU/mL.

As shown in FIG. 21A, the inoculum preparation times ranged from 40 minutes to 149 minutes with an average time of 106 minutes±28 minutes.

Figure 21B:
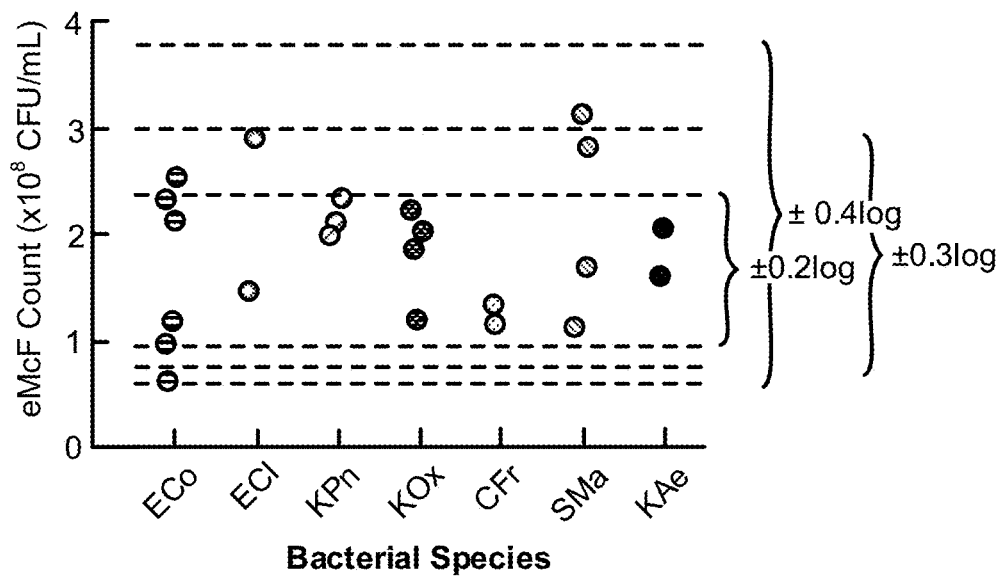
FIG. 21B is another dot plot showing the actual concentrations of the 23 standardized inocula determined using traditional bacterial quantification techniques by plating and counting bacterial colonies on agar.

FIG. 21B is another dot plot showing the actual concentrations of the 23 standardized inocula determined using traditional bacterial quantification techniques by plating and counting bacterial colonies on agar. As previously discussed, the 23 standardized inocula were prepared from 23 different PBC samples comprising seven different species of bacteria (ECo, ECl, KPn, KOx, CFr, SMa, and KAe) using the method 1700 and system 1702 disclosed herein.

The broken/dotted lines represent error ranges around the targeted concentration of $1.5*10^8$ CFU/mL. As shown in FIG. 21B, 18 out of the 23 samples fell within ±0.2 log of the target concentration ($1.5*10^8$ CFU/mL) 21 out of the 23 samples fell within ±0.3 log of the target concentration, and all 23 samples fell within ±0.4 log of the target concentration.

FIGS. 22A and 22B illustrate the results of periodic colony counts conducted on PBCs incubated at 20° C. and 37° C., respectively. The PBCs were prepared from aerobic and anaerobic blood cultures comprising nine clinically significant Gram-negative microorganisms including ECo, KPn, KOx, ECl, KAe, SMa, CFr, *Proteus mirabilis*, and *Proteus vulgaris*. These blood cultures were incubated to positivity and held at either room temperature (about 20° C.) or incubated to an incubation temperature of about 37° C. Aliquots of the PBCs were sampled at four different time points: one hour (T1), four hours (T4), eight hours (T8), and twelve hours (T12) post positivity flag time. Aliquots were then plated for colony counts at each of the time points (see, e.g., FIGS. 22A and 22B) and used to prepare 208 standardized 0.5 McFarland using the method 1700 and system 1702 disclosed herein. As expected, PBC bacterial concentrations were lowest when measured at T1 and rose significantly over time, reaching approximate saturation during T8 to T12.

As shown in FIGS. 22C and 22D, despite the extended incubation times (which allowed the bacterial concentrations to increase and vary widely), 96% of the standardized inocula prepared from such PBCs were within ±0.3 log of the target concentration of $1.5*10^8$ CFU/mL (as determined using traditional bacterial quantification techniques by plating and counting bacterial colonies on agar). The dotted/broken lines in FIGS. 22C and 22D represent various log 10 ranges (±0.3 log and ±0.4 log) around the target concentration of $1.5*10^8$ CFU/mL.

These results indicate that the method 1700 and system 1702 disclosed herein can be used to generate an accurate standardized inoculum (e.g., a 0.5 McFarland inoculum) from PBCs that have been incubated for up to 4 hours, 8 hours, and even 12 hours at either 20° C. or 37° C.

One of the technical unknowns was whether the method 1700 and system 1702 disclosed herein could be used to generate a standardized inoculum from PBC samples that have been kept or incubated for durations in excess of 4 hours, 8 hours, and even 12 hours. This is often the case when a sample is brought in from other/third-party labs or clinical settings. As discovered by the applicants, the method 1700 and system 1702 disclosed herein can be used to successfully generate a standardized inoculum from PBC samples that have been kept or incubated for durations in excess of 4 hours, 8 hours, and even 12 hours.

A number of embodiments have been described. Nevertheless, it will be understood by one of ordinary skill in the art that various changes and modifications can be made to this disclosure without departing from the spirit and scope of the embodiments. Elements of systems, devices, apparatus, and methods shown with any embodiment are exemplary for the specific embodiment and can be used in combination or otherwise on other embodiments within this disclosure. For example, the steps of any methods depicted in the figures or described in this disclosure do not require the particular order or sequential order shown or described to achieve the desired results. In addition, other steps operations may be provided, or steps or operations may be eliminated or omitted from the described methods or processes to achieve the desired results. Moreover, any components or parts of any apparatus or systems described in this disclosure or depicted in the figures may be removed, eliminated, or omitted to achieve the desired results. In addition, certain components or parts of the systems, devices, or apparatus shown or described herein have been omitted for the sake of succinctness and clarity.

Accordingly, other embodiments are within the scope of the following claims and the specification and/or drawings may be regarded in an illustrative rather than a restrictive sense.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein. For example, a description of a range from 1 to 5 should be considered to have disclosed subranges such as from 1 to 3, from 1 to 4, from 2 to 4, from 2 to 5, from 3 to 5, etc. as well as individual numbers within that range, for example 1.5, 2.5, etc. and any whole or partial increments therebetween.

All existing subject matter mentioned herein (e.g., publications, patents, patent applications) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

In understanding the scope of the present disclosure, the term "comprising" and its derivatives, as used herein, are intended to be open-ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" "element," or "component" when used in the singular can have the dual meaning of a single part or a plurality of parts. As used herein, the following directional terms "forward, rearward, above, downward, vertical, horizontal, below, transverse, laterally, and vertically" as well as any other similar directional terms refer to those positions of a device or piece of equipment or those directions of the device or piece of equipment being translated or moved. Finally, terms of degree such as "substantially", "about" and "approximately" as used herein mean a reasonable amount of deviation (e.g., a deviation of up to ±0.1%, ±1%, ±5%, or ±10%, as such variations are appropriate) from the specified value such that the end result is not significantly or materially changed.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

What is claimed is:

1. A system for preparing a standardized inoculum for downstream testing, the system comprising:
    a sensor apparatus comprising:
        a sample container comprising a chamber cavity configured to receive a diluted sample comprising an infectious agent, wherein the chamber cavity is surrounded by a chamber lateral wall, wherein the sample container comprises an active sensor coupled to at least part of the chamber lateral wall at a window opening defined along the chamber lateral wall and no part of the active sensor extends into the chamber cavity, and wherein the sample container is configured to allow the diluted sample within the chamber cavity to be in fluid contact with the active sensor through at least part of the chamber lateral wall surrounding the window opening, and
    a container cap configured to couple to the sample container when the chamber cavity is filled with the diluted sample, wherein at least part of the container cap serves as a reference sensor; and
    a reader configured to receive the sensor apparatus when the container cap is coupled to the filled sample container, wherein at least part of the reader is configured to be in electrical contact with the active sensor and the reference sensor when the sensor apparatus is placed within the reader, wherein the reader comprises one or more processors and a memory, and wherein the one or more processors are programmed to execute instructions stored in the memory to:
    monitor a change in a solution characteristic of the diluted sample, and
    generate an alert or notification, via a display of the reader or a computing device in communication with the reader, when the solution characteristic changes by a threshold amount to indicate successful preparation of the standardized inoculum from the diluted sample.

2. The system of claim 1, wherein the diluted sample is made by diluting a source sample, wherein the source sample is a bacterial culture or a re-suspended bacterial culture derived from a bodily fluid or swab obtained from a subject that has tested positive for bacterial growth.

3. The system of claim 2, wherein the bodily fluid is blood and the source sample comprises red blood cells.

4. The system of claim 2, wherein the bacterial culture or the re-suspended bacterial culture derived from the bodily fluid or the swab obtained from the subject tested positive for bacterial growth between 1 hour and 12 hours prior.

5. The system of claim 1, wherein the reader further comprises:
   a heating block configured to incubate the diluted sample while the solution characteristic of the diluted sample is being monitored; and
   a cooling component configured to cool the standardized inoculum within the sample container to a cooling temperature.

6. The system of claim 1, wherein the standardized inoculum is a 0.5 McFarland inoculum comprising between about $1*10^8$ to about $2*10^8$ colony forming units per milliliters (CFU/mL) of bacteria.

7. The system of claim 1, wherein the active sensor is hermetically sealed using film assisted molding except for a portion of an active electrode layer of the active sensor left exposed, and wherein the portion of the active electrode layer left exposed is positioned to face the chamber cavity to allow the diluted sample within the chamber cavity to be in fluid contact with the portion of the active electrode layer left exposed.

8. The system of claim 1, wherein the active sensor is covered in part by an active electrode layer, wherein the solution characteristic monitored is an oxidation reduction potential and wherein the active electrode layer is a platinum layer.

9. The system of claim 1, wherein the active sensor is covered in part by an active electrode layer, wherein the solution characteristic monitored is pH and wherein the active electrode layer is a pH-sensitive layer.

10. The system of claim 1, wherein the reference sensor comprises a reference electrode material and a wick extending through the container cap and into the chamber cavity, wherein at least some of the diluted sample is drawn by the wick in a direction of the reference electrode material.

11. The system of claim 1, wherein the one or more processors are programmed to execute further instructions stored in the memory to:
   receive a user input identifying a species of the infectious agent within the diluted sample;
   retrieve a species-specific look-up table from a database based on the species of the infectious agent in the source sample prior to monitoring the change in the solution characteristic of the diluted sample; and
   set the threshold amount using the species-specific look-up table based on a desired concentration of the standardized inoculum.

12. The system of claim 1, wherein the diluted sample is made by diluting an aliquot of a source sample using growth media by a dilution factor of between 1:10 to 1:30.

13. The system of claim 1, wherein the sample container is cleaned using an alcohol-based disinfectant solution with sonication prior to receiving the diluted sample.

* * * * *